United States Patent
Vera Rodriguez et al.

(10) Patent No.: US 12,209,260 B2
(45) Date of Patent: Jan. 28, 2025

(54) PROTEASE SPECIFIC FOR A NOVEL SUMO-DERIVED PROTEASE CLEAVAGE SITE

(71) Applicant: MAX-PLANCK-GESELLSCHAFT ZUR FÖRDERUNG DER WISSENSCHAFTEN E.V., Munich (DE)

(72) Inventors: Arturo Vera Rodriguez, Göttingen (DE); Dirk Görlich, Göttingen (DE); Steffen Frey, Göttingen (DE)

(73) Assignee: MAX-PLANCK-GESELLSCHAFT ZUR FORDERUNG DER WISSENSCHAFTEN E.V., Munich (DE)

( * ) Notice: Subject to any disclaimer, the term of this patent is extended or adjusted under 35 U.S.C. 154(b) by 194 days.

(21) Appl. No.: 17/251,266

(22) PCT Filed: Jun. 13, 2019

(86) PCT No.: PCT/EP2019/065516
§ 371 (c)(1),
(2) Date: Dec. 11, 2020

(87) PCT Pub. No.: WO2019/238828
PCT Pub. Date: Dec. 19, 2019

(65) Prior Publication Data
US 2021/0261937 A1 Aug. 26, 2021

(30) Foreign Application Priority Data
Jun. 14, 2018 (EP) .................................. 18177803

(51) Int. Cl.
*C12N 9/60* (2006.01)
*C07K 1/22* (2006.01)

(52) U.S. Cl.
CPC .................. *C12N 9/60* (2013.01); *C07K 1/22* (2013.01); *C07K 2319/50* (2013.01)

(58) Field of Classification Search
CPC .......... C12N 9/60; C12N 9/1205; C07K 1/22; C07K 2319/50; C07K 2319/00; C07K 2319/95
See application file for complete search history.

(56) References Cited

U.S. PATENT DOCUMENTS 7,655,413 B2   2/2010 Butt et al.
2012/0065107 A1 3/2012 Ring et al.

OTHER PUBLICATIONS

WO2019238828, Written Opinion of the Interantional Searching Authority. Dec. 19, 2019.*
Witkowski et al., Biochemistry 38:11643-11650, 1999.*
Tang et al., Phil Trans R Soc B 368:20120318, 1-10, 2013.*
Seffernick et al., J. Bacteriol. 183(8):2405-2410, 2001.*
Singh et al., Current Protein and Peptide Science 19(1):5-15, 2018.*
Sadowski et al., Current Opinion in Structural Biology 19:357-362, 2009.*
Lucas et al., GenBank accession No. KQK04268, Oct. 29, 2015.*
UniProtKB accession No. 11HF82_BRADI published Jan. 9, 2013.*
Amor-Mahjoub, M. et al., The effect of the hexahistidine-tag in the oligomerization of HSC70 constructs. Journal of Chromatography B: Analytical Technologies in the Biomedical and Life Sciences, 844(2), pp. 328-334, 2006.
Bachmair, a, Finley, D. & Varshavsky, a, In vivo half-life of a protein is a function of its amino-terminal residue. Science (New York, N.Y.), 234(4773), pp. 179-186, 1986.
Bohnsack, M.T., Exportin 5 is a RanGTP-dependent dsRNA-binding protein that mediates nuclear export of pre-miRNAs. RNA, 10(2), pp. 185-191, 2004.
Butt, T.R. et al., SUMO fusion technology for difficult-to-express proteins. Protein Expression and Purification, 43(1), pp. 1-9, 2005.
Chan, P. et al., Purification of Heterotrimeric G Protein Subunits by GST-Ric-8 Association: Primary Characterization of Purified G olf. Journal of Biological Chemistry, 286(4), pp. 2625-2635, 2011.
Chant, A. et al., Attachment of a histidine tag to the minimal zinc finger protein of the Aspergillus nidulans gene regulatory protein AreA causes a conformational change at the DNA-binding site. Protein Expression and Purification, 39(2), pp. 152-159, 2005.
Chen, X., Pham, E. & Truong, K., TEV protease-facilitated stoichiometric delivery of multiple genes using a single expression vector. Protein Science, 19(12), pp. 2379-2388, 2010.
Frey, S. & Görlich, D., A new set of highly efficient, tag-cleaving proteases for purifying recombinant proteins. Journal of Chromatography A, 1337, pp. 95-105, 2014a.

(Continued)

*Primary Examiner* — Delia M Ramirez
(74) *Attorney, Agent, or Firm* — Birch, Stewart, Kolasch & Birch, LLP

(57) ABSTRACT

The present invention relates to a fusion protein, comprising the structure N-$PCS^Y$-$degSig_N$-M-$PCS^X$-$degSig_C$-C; wherein N represents the N-terminus; $PCS^Y$ and $PCS^X$ each represent a protease cleavage site (PCS), which differ from each other in at least one amino acid residue: $degSig_N$ represents a degradation signal which promotes degradation of the fusion protein in a host cell if $PCS^Y$ is cleaved by a protease such that the first amino acid of $degSig_N$ becomes the new N-terminus of the remaining fusion; M represents a cytoplasmic selection marker; and $degSig_C$ represents a second degradation signal which promotes degradation of the fusion protein in a host cell if $PCS^X$ is not cleaved by a protease; and C represents the C-terminus. Further provided is a nucleic acid construct, comprising a nucleic acid sequence coding for said fusion protein, a nucleic acid expression construct library, comprising a plurality of such nucleic acid expression constructs in diversified form, and methods using the fusion protein and nucleic acid constructs coding therefor. Finally, the present invention provides variants of bdSUMO and bdSENP1 which have been identified by the methods of the present disclosure, and which exhibit improved properties over existing orthogonal protease/protease cleavage site-pairs which are currently used with wild-type bdSUMO and wildtype bdSENP1.

19 Claims, 14 Drawing Sheets
Specification includes a Sequence Listing.

(56) References Cited

OTHER PUBLICATIONS

Frey, S. & Görlich, D., Purification of protein complexes of defined subunit stoichiometry using a set of orthogonal, tag-cleaving proteases. Journal of Chromatography A, 1337, pp. 106-115, 2014b.

Harder, B. et al., TEV protease-mediated cleavage in *Drosophila* as a tool to analyze protein functions in living organisms. BioTechniques, 44(6), pp. 765-772, 2008.

Harper, S. & Speicher, D.W., Purification of Proteins Fused to Glutathione S-Transferase. In Methods in molecular biology (Clifton, N.J.). pp. 259-280, 2011.

Hendriks, I.A. & Vertegaal, A.C.O., A comprehensive compilation of SUMO proteomics. Nature reviews. Molecular cell biology, 17(9), pp. 581-595, 2016.

Herrmann, J., Lerman, L.O. & Lerman, A., Ubiquitin and ubiquitin-like proteins in protein regulation. Circulation Research, 100(9), pp. 1276-1291, 2007.

Himeno, H., Kurita, D. & Muto, A., TmRNA-mediated trans-translation as the major ribosome rescue system in a bacterial cell. Frontiers in Genetics, 5(APR), pp. 1-13, 2014.

Katzmann, D.J., Babst, M. & Emr, S.D., Ubiquitin-dependent sorting into the multivesicular body pathway requires the function of a conserved endosomal protein sorting complex, ESCRT-I. Cell, 106(2), pp. 145-155, 2001.

Keiler, K.C., Biology of trans—Translation. Annual Review of Microbiology, 62(1), pp. 133-151, 2008.

Kerscher, O., Felberbaum, R. & Hochstrasser, M., Modification of proteins by ubiquitin and ubiquitin-like proteins. Annual review of cell and developmental biology, 22, pp. 159-180, 2006.

Khorasanizadeh, S., Peters, I.D. & Roder, H., Evidence for a three-state model of protein folding from kinetic analysis of ubiquitin variants with altered core residues. Nature structural biology, 3(2), pp. 193-205, 1996.

Kimple, M.E., Brill, A.L. & Pasker, R.L., Overview of affinity tags for protein purification. Current Protocols in Protein Science, (SUPPL. 73), pp. 608-616, 2013.

Kosobokova, E.N., Skrypnik, K.A. & Kosorukov, V.S., Overview of fusion tags for recombinant proteins. Biochemistry (Moscow), 81(3), pp. 187-200, 2016.

Kostelansky, M.S. et al., Molecular Architecture and Functional Model of the Complete Yeast ESCRT-I Heterotetramer. Cell, 129(3), pp. 485-498, 2007.

Kuwata, T. & Nakamura, T., BCL11A is a SUMOylated protein and recruits SUMO-conjugation enzymes in its nuclear body. Genes to Cells, 13(9), pp. 931-940, 2008.

Malakhov, M.P. et al., SUMO fusions and SUMO-specific protease for efficient expression and purification of proteins. Journal of Structural and Functional Genomics, 5(1-2), pp. 75-86, 2004.

Marblestone, J.G. et al., Comparison of SUMO fusion technology with traditional gene fusion systems: enhanced expression and solubility with SUMO. Protein science: a publication of the Protein Society, 15(1), pp. 182-189, 2006.

McCoy, J. & La Ville, E., Expression and Purification of Thioredoxin Fusion Proteins. In Current Protocols in Protein Science. Hoboken, NJ, USA: John Wiley & Sons, Inc., p. 6.7.1-6.7.14, 1997.

Pattenden, L.K. & Thomas, W.G., Amylose Affinity Chromatography of Maltose-Binding Protein. In Affinity Chromatography. Totowa, NJ: Humana Press, pp. 169-190, 2008.

Rao, R.N., Allen, N.E. & Hobbs, J.N., Genetic and enzymatic basis of hygromycin B resistance in *Escherichia coli*. Genetic and Enzymatic Basis of Hygromycin B Resistance in *Escherichia coli*. Antimicrobial Agents and Chemotherapy, 24(5), pp. 689-695, 1983.

Reverter, D. & Lima, C.D., A basis for SUMO protease specificity provided by analysis of human Senp2 and a Senp2-SUMO complex. Structure, 12(8), pp. 1519-1531 2004.

Reverter, D. & Lima, C.D., Structural basis for SENP2 protease interactions with SUMO precursors and conjugated substrates. Nature Structural & Molecular Biology, 13(12), pp. 1060-1068, 2006.

Rodriguez, Arturo Vera, "Novel export and import pathways in *S. cerevisiae* identified by an engineered SUMO system" In: Dissertation for the award of the degree 'Doctor rerum naturalium' within the Molecular Biology Program of the Georg-August-Universität Göttingen, Georg-August-Universität Göttingen, pp. 1-132, Jun. 26, 2017.

Sato, M. & Toda, T., Alp7/TACC is a crucial target in Ran-GTPase-dependent spindle formation in fission yeast. Nature, 447(7142), pp. 334-337, 2007.

Shen, L. et al., SUMO protease SENP1 induces isomerization of the scissile peptide bond. Nature Structural & Molecular Biology, 13(12), pp. 1069-1077, 2006.

Suh-Lailam, B.B. & Hevel, J.M., Efficient cleavage of problematic tobacco etch virus (TEV)-protein arginine methyltransferase constructs. Analytical Biochemistry, 387(1), pp. 130-132, 2009.

Taxis, C. & Knop, M., TIPI: TEV Protease-Mediated Induction of Protein Instability. In Methods in Molecular Biology. pp. 611-626, 2012.

Vertegaal, A.C.O. et al., A proteomic study of SUMO-2 target proteins. Journal of Biological Chemistry, 279(32), pp. 33791-33798, 2004.

Wang, K.H. et al., Tuning the strength of a bacterial N-end rule degradation signal. Journal of Biological Chemistry, 283(36), pp. 24600-24607, 2008.

Woestenenk, E.A. et al., His tag effect on solubility of human proteins produced in *Escherichia coli*: A comparison between four expression vectors. Journal of Structural and Functional Genomics, 5(3), pp. 217-229, 2004.

Xu, Z. et al., Crystal structure of the SENP1 mutant C603S-SUMO complex reveals the hydrolytic mechanism of SUMO-specific protease. The Biochemical journal, 398(3), pp. 345-352, 2006.

Yan, Y., Orcutt, S.J. & Strickler, J.E., The use of SUMO as a fusion system for protein expression and purification. Chimica oggi, 27(6), 2009.

Zuo, X., Li, S., et al., Enhanced expression and purification of membrane proteins by SUMO fusion in *Escherichia coli*. Journal of Structural and Functional Genomics, 6(2-3), pp. 103-111, 2005.

Zuo, X., Mattern, M.R., et al., Expression and purification of SARS coronavirus proteins using SUMO-fusions. Protein Expression and Purification, 42(1), pp. 100-110, 2005.

International Search Report and Written Opinion for PCT/EP2019/065516, European Patent Office, Oct. 14, 2019.

"Doctoral degree regulations of the mathematics and natural sciences graduate school of the Georg-August-Universitat Gottingen," Georg-August University School of Science (GAUSS)—RerNat-O, 2018, pp. 1-5.

Japanese Office Action for Japanese Application No. 2020-569885, dated May 30, 2023, with English translation.

Rodriguez, "Novel export and import pathways in *S. cerevisiae* identified by an engineered SUMO system," Gottingen State and University Library HP, Sep. 7, 2018, pp. 1-2, retrieved on May 8, 2023 from https://ediss.uni-goettingen.de/handle/11858/00-1735-0000-002E-E49F-0?locale-attribute=en.

* cited by examiner

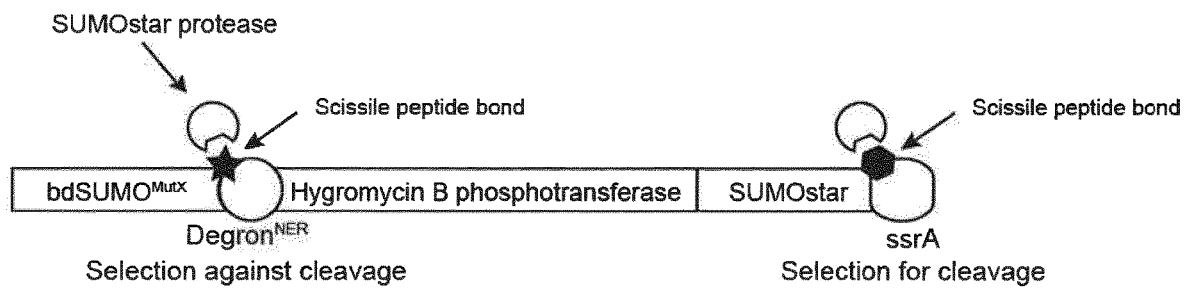

B

```
bdSUMOwt    56 SVDMTAIAFLFDGRRLRAEQTPDE 79
bdSUMOMut1  56 SVDMKAIAFLFKGRRLRAERTPDE 79
bdSUMOMut2  56 SVDMTAIAFLFKGRRLRAECTPDE 79
bdSUMOMut3  56 SVDMHAIAFLFKGRRLRAEKTPDE 79
bdSUMOMut4  56 SVDMRAIAFLFRGRRLRAEVTPDE 79
bdSUMOMut5  56 SVDMTAIAFLFKGRRLRAEFTPDE 79
bdSUMOMut6  56 SVDMHAIAFLFKGRRLRAEQTPDE 79
bdSUMOMut7  56 SVDMDAIAFLFRGRRLRAECTPDE 79
bdSUMOMut8  56 SVDMPAIAFLFKGRRLRAEWTPDE 79
bdSUMOMut9  56 SVDMAAIAFLFKGRRLRAEYTPDE 79
bdSUMOMut10 56 SVDMTAIAFLFKGRRLRAERTPDE 79
```

PROTEASE SPECIFIC FOR A NOVEL SUMO-DERIVED PROTEASE CLEAVAGE SITE

CROSS-REFERENCE TO RELATED APPLICATIONS

This application is the U.S. National Stage of International Application PCT/EP2019/065516, filed Jun. 13, 2019, which designates the U.S. and was published by the International Bureau in English on Dec. 19, 2019, and which claims the benefit of European Patent Application No. 18177803.6, filed Jun. 14, 2018; both of which are hereby incorporated herein in their entirety by reference.

REFERENCE TO ELECTRONIC SEQUENCE LISTING

The application contains a Sequence Listing which has been submitted electronically in .txt format and is hereby incorporated by reference in its entirety. Said .txt copy, created on Sep. 4, 2024, is named "151523_sequence listing_revised incl. seq73_ST25" and is 81,689 bytes in size. The sequence listing contained in this .file is part of the specification and is hereby incorporated by reference herein in its entirety.

FIELD OF THE INVENTION

The present disclosure pertains to the field of molecular biology. More specifically, the present disclosure provides a fusion protein, which can be used to develop orthogonal proteases/protease cleavage-sites, methods using said fusion protein, as well as variant protease cleavage-sites of bdSUMO and variant proteases of bdSENP1.

BACKGROUND OF THE INVENTION

Recombinant protein expression and purification are fundamental for modern biochemistry and structural biology as well as for the production of proteins and protein complexes for practical applications.

The most exploited protein expression system is the bacterium *E. coli* because of the ease of its genetic manipulation, low cost of biomass production and fast growth kinetics. *E. coli* fails, however, to introduce typical eukaryotic post-translational modifications and in many cases also to fold eukaryotic proteins properly. Expression in eukaryotic hosts is then an alternative.

Affinity tags facilitate the purification of recombinant proteins considerably. Poly histidine tagged proteins, for example, can be purified in a standardized manner, namely by binding to a Ni(II) chelate matrix, washing off contaminants and desorption by imidazole. The maltose-binding protein (MBP), thioredoxin (TRX), or NusA exemplify another category of tags, namely those that enhance the level of expression, solubility and successful folding of the fused target protein, in particular if *E. coli* is used as an expression host. Tags may interfere with the target protein's function or the intended application. It is therefore often desired to remove them from the target protein. Tag removal is typically implemented by (I) modular fusions of an N-terminal tag (or tags), an intervening protease-cleavage site (PCS) and the protein of choice; (II) by treatment of the purified fusion protein with an appropriate PCS-specific protease and (III) separation of the target protein from the cleaved tag and the protease.

The "affinity capture and proteolytic release strategy" is a particularly efficient implementation of affinity chromatography. A tag-PCS-target protein fusion is bound through the tag to an affinity matrix. However, elution is not achieved by disengaging the tag from the matrix, but by cleavage of the PCS module. This procedure combines the specificities of the affinity matrix with that of the protease and therefore yields far purer protein preparations than affinity chromatography alone. Furthermore, it is time-saving and simplifies the workflow by eliminating the need for separate tag cleavage and tag removal.

An extension of this strategy even allows to select for the presence of several subunits within a given protein complex. This requires that two or more subunits are equipped with distinct (and non-cross reacting) affinity tags and with distinct PCSs, and that two or more rounds of affinity capture and proteolytic release are performed in succession (Frey & Görlich 2014b). Furthermore, it requires that the used proteases are orthogonal in their specificities, i.e. that each protease cleaves only "its" PCS and leaves the others intact.

One type of tag-cleaving proteases recognizes short linear peptides as PCSs, examples being: thrombin, Factor Xa, enterokinase, human rhinovirus 3C protease, or TEV protease. These suffer, however, from one or several of the following problems: poor specificity leading also to degradation of the target protein, poor substrate turnover, poor activity at low temperature (4° C.), remaining undesired residues on the target protein, or difficult production of the protease (reviewed in Yan et al. 2009).

Proteases that recognize ubiquitin-like modifiers (Ubls), such as SUMO, NEDD8 or Atg4 as a PCSs, overcome these difficulties (Malakhov et al. 2004; Frey & Görlich 2015; Frey & Görlich 2014a). They recognize the 3D fold of the cognate Ubls and cleave behind a Gly-Gly motif (Phe-Gly or Tyr-Gly in the case of Atg8), accept all amino acids (except for Pro) at the $P_1'$ position, and they show a tremendous substrate turnover even at temperatures as low as 0° C. (Frey & Görlich 2014a). Previously used Ubl-proteases include: *S. cerevisiae* Ulp1 (also called SENP1, cleaving SUMO-fusions), *Brachypodium distachyon* bdSENP1 (also cleaving SUMO-fusions), *Brachypodium distachyon* or Salmon salar NEDP1 (cleaving NEDD8-fusions), *Xenopus laevis* Atg4B (cleaving Atg8-fusions).

An additional advantage of the use of Ubls as PCSs is that they have (like MBP, NusA or thioredoxin) a strong expression- and fold-enhancing effect. They can, however, not be used in eukaryotic expressing systems, because the endogenous Ubl-proteases cause a premature tag-cleavage. So far, there was only one attempt to solve this problem, namely the SUMOstar system (Patent US 2012/0065106 A1). SUMOstar is derived from yeast SUMO (scSUMO) and carries the R64T and R17E mutations that disrupt the Ulp1-binding interface, while the SUMOstar protease is a D451S, T452G and E455S-mutated version of the wild type yeast Ulp1 protease. SUMOstar protease cleaves wild type scSUMO as well as the SUMOstar fusions with comparable efficiency. It is thus not orthogonal to the parental protease.

The purpose of this invention was to create a generic in vivo selection system to evolve protease/PCS pairs to enhanced and novel specificities, and in particular to orthogonality to a reference pair. A further aim was to evolve SUMO mutants that can be used as a stable fusion tag in any eukaryotic systems and that is resistant to cleavage SUMO-specific proteases from yeast, plants, human, amphibians, and insects as well as to cleavage by the SUMOstar protease. A final aim was to evolve a variant bdSENP1 protease, which (I) efficiently cleaves the new bdSUMO mutant(s), but not wild type scSUMO, human SUMO (i.e. hsSUMO2) or SUMOstar-fusions and (II) causes no toxicity when expressed in a prokaryotic or eukaryotic host.

SUMMARY OF THE INVENTION

The present disclosure relates to a selection system for evolving proteases and protease-cleavage modules to novel specificities. We describe a SUMO protein mutant (bdSUMO$^{Mut1}$) as a novel protease-cleavage module, which is highly resistant to cleavage by previously described SUMO proteases and thus allows the stable expression of bdSUMO$^{Mut1}$-fusion proteins in eukaryotic hosts. We further describe a SUMO protease mutant (bdSENP1$^{MutB}$), which leaves SUMOstar and wild type SUMO fusion proteins intact but cleaves bdSUMO$^{Mut1}$-fusion proteins efficiently and thus enables tag-removal as well as protein purification by the "affinity capture and proteolytic release strategy". Both, bdSUMO$^{Mut1}$ and bdSENP1$^{MutB}$ are part of our novel SUMOvera system, which is described in detail through the following sections. In addition, bdSUMO mutants 8, 10, 11, 12, 13, 14, 15 as well as bdSENP1 mutants G, H, i, J and K are described as alternative parts of the system.

Summary of the Claimed Aspects

In more generic terms, the present invention relates to a fusion protein, comprising the structure N-PCS$^Y$-degSig$_N$-M-PCS$^X$-degSig$_C$-C;

wherein N represents the N-terminus;
PCS$^Y$ and PCS$^X$ each represent a protease cleavage site (PCS), which differ from each other in at least one amino acid residue;
degSig$_N$ represents a degradation signal, which promotes degradation of the fusion protein in a host cell if PCS$^Y$ is cleaved by a protease such that the first residue of degSig$_N$ becomes the new N-terminus of the remaining fusion;
M represents a cytoplasmic selection marker; and
degSig$_C$ represents a second degradation signal, which promotes degradation of the fusion protein in a host cell if PCS$^X$ is not cleaved by a protease; and
C represents the C-terminus.

Further provided is a nucleic acid construct, comprising a nucleic acid sequence coding for the fusion protein of the present disclosure.

Also provided is a nucleic acid expression construct library, comprising a plurality of diversified nucleic acid expression constructs of the present disclosure,
wherein the nucleic acid encoding PCS$^Y$ of the fusion protein comprises a diversity such that in the encoded PCS$^Y$ at least one amino acid position is diversified.

The present disclosure moreover provides a plurality of host cells, wherein each member of the plurality of host cells comprises a nucleic acid expression construct of the present disclosure, which is not diversified, or a member of a plurality of diversified nucleic acid expression constructs according to the present disclosure, wherein the host cells promote degradation of the fusion protein via degSig$_N$, if PCS$^Y$ is cleaved by a protease, and promote degradation of the fusion protein via degSig$_C$, if PCS$^X$ is not cleaved by a protease. In embodiments, the host cells are capable of simultaneously expressing a protease of interest and the fusion protein encoded by the nucleic acid expression construct, wherein said protease of interest is capable of cleaving PCS$^X$.

Alternatively, the host cells may comprise a first non-diversified nucleic acid expression construct according to the present disclosure, and each member of said plurality of host cells comprises a member of a plurality of second expression constructs encoding a diversified protease of interest, wherein the host cells are capable of simultaneously expressing said diversified protease of interest together with the fusion protein encoded by said first expression construct, wherein said plurality of second expression constructs is derived from a protease capable of cleaving PCS$^Y$ of the fusion protein of the first expression construct, and whereby the plurality of second expression constructs comprises a diversity in at least one amino acid position at the protease interface interacting with said PCS$^Y$.

Furthermore, the present disclosure provides a method for simultaneously testing whether (a) a first protease cleavage site PCS$^Y$ is not cleaved by a protease of interest, and (b) whether a second protease cleavage site PCS$^X$ is cleaved by said protease of interest, comprising the steps of
 (i) providing a host cell comprising a first (non-diversified) nucleic acid construct according to the present disclosure and a second expression construct for expression of a protease of interest, wherein the host cell is capable of simultaneously expressing the fusion protein and said protease of interest, and wherein the host cell promotes degradation of the fusion protein via degSig$_N$, if PCS$^Y$ is cleaved by a protease; and promotes degradation of the fusion protein via degSig$_C$, if PCS$^X$ is not cleaved by a protease;
 (ii) cultivating the host cell of step (i) under conditions such that the fusion protein and the protease of interest are simultaneously expressed; and
 (iii) subjecting the host cell of step (ii) to selective conditions using the cognate selecting agent for the selection marker of the fusion protein encoded by the first nucleic acid construct;
wherein growth of the host cell in the presence of the selective conditions applied in step (iii) indicates that the first protease cleavage site PCS$^Y$ is not cleaved by said protease of interest, and that said second protease cleavage site PCS$^X$ is cleaved by said protease of interest of said second nucleic acid expression construct; preferably wherein the selection marker confers antibiotic resistance to the host cell.

Additionally, the present disclosure provides a method for identifying a protease cleavage site variant PCS$^Y$ of a first protease cleavage site PCS$^X$, wherein PCS$^Y$ is not cleaved by a protease of interest, comprising the steps of
 (i) providing a plurality of host cells, wherein each member of said plurality of host cells comprises a member of a plurality of first nucleic acid constructs according to the present disclosure, which encodes for a diversified variant PCS$^Y$ of a first protease cleavage site PCS$^X$, and a second expression construct for expression of a protease of interest, wherein said protease of interest is capable of cleaving PCS$^X$, whereby the plurality of host cells is capable of simultaneously expressing the fusion protein encoded by the first nucleic acid construct and said protease of interest, and wherein the host cells promote degradation of the fusion protein via degSig$_N$, if PCS$^Y$ is cleaved by a protease; and promote degradation of the fusion protein via degSig$_C$, if PCS$^X$ is not cleaved by a protease;

(ii) cultivating the plurality of host cells of step (i) under conditions such that the fusion protein and the protease of interest are simultaneously expressed; and (iii) subjecting the plurality of host cells of step (ii) to selective conditions using the cognate selecting agent for the selection marker of the fusion protein encoded by the plurality of first nucleic acid constructs;

(iv) identifying a host cell, which has been positively selected in step (iii), and identifying the sequence of $PCS^Y$ of the first nucleic acid construct of the identified host cell, wherein $PCS^Y$ is a protease cleavage site variant of a first protease cleavage site $PCS^X$, and wherein $PCS^Y$ is not cleaved by said protease of interest of the second expression construct.

The present disclosure further pertains to a method for identifying a protease variant, which is capable of cleaving a protease cleavage site variant $PCS^X$ of a first protease cleavage site $PCS^Y$, but not the first protease cleavage site $PCS^Y$, wherein said protease variant is derived from a first protease, which is capable of cleaving the first protease cleavage site $PCS^Y$, but not the protease cleavage site variant $PCS^X$, comprising the steps of (i) providing a plurality of host cells, wherein each member comprises a non-diversified first nucleic acid expression construct according to the present disclosure, in which $PCS^X$ is a protease cleavage site variant of a first protease cleavage site $PCS^Y$, wherein the $PCS^Y$ is cleaved by a first protease of interest and $PCS^X$ is not cleaved by said first protease; and wherein each member of said plurality of host cells further comprises a member of a plurality of a second expression constructs expressing protease variants of said first protease, wherein said plurality of second nucleic acid expression constructs comprises a diversity in at least one amino acid position at the protease interface interacting with said first $PCS^Y$, whereby the plurality of host cells is capable of simultaneously expressing the fusion protein and said protease of interest, and wherein the host cells promote degradation of the fusion protein via $degSig_N$, if $PCS^Y$ is cleaved by a protease; and promote degradation of the fusion protein via $degSig_C$, if $PCS^X$ is not cleaved by a protease;

(ii) cultivating the plurality of host cells of step (i) under conditions such that the fusion protein and the protease of interest are simultaneously expressed; and (iii) subjecting the plurality of host cells of step (ii) to selective conditions using the cognate selecting agent for the selection marker of the fusion protein encoded by the first nucleic acid expression construct; and (iv) identifying a host cell, which has been positively selected in step (iii), and identifying the sequence of the protease variant encoded by the second nucleic acid construct of the identified host cell, wherein said protease variant is capable of cleaving a protease cleavage site variant $PCS^X$ of a first protease cleavage site $PCS^Y$, but is incapable of cleaving the first protease cleavage site $PCS^Y$.

Combination of the above-described methods provides a method of preparing an orthogonal protease (P)/protease cleavage site (PCS) system, comprising the steps of (i) providing a plurality of host cells, wherein each member of said plurality of host cells comprises a member of a plurality of first nucleic acid constructs according to the present disclosure, which encodes a diversified variant $PCS^Y$ of a first protease cleavage site $PCS^X$, and a second expression construct for expression of a first protease $P^X$ of interest, which is capable of cleaving $PCS^X$, whereby the plurality of host cells is capable of simultaneously expressing the fusion protein and said first protease of interest, and wherein the host cells promote degradation of the fusion protein via $degSig_N$, if $PCS^Y$ is cleaved by a protease; and promote degradation of the fusion protein via $degSig_C$, if $PCS^X$ is not cleaved by a protease;

(ii) cultivating the plurality of host cells of step (i) under conditions such that the fusion protein and the first protease $P^X$ are simultaneously expressed; and (iii) subjecting the plurality of host cells of step (ii) to selective conditions using the cognate selecting agent for the selection marker of the fusion protein encoded by the plurality of first nucleic acid constructs (iv) identifying a host cell, which has been positively selected in step (iii), and identifying $PCS^\#$, wherein $PCS^\#$ is the sequence of the $PCS^Y$ from the first nucleic acid construct of the identified host cell, wherein $PCS^\#$ is a protease cleavage site variant of a first protease cleavage site $PCS^X$, and wherein $PCS^\#$ is not cleaved by said first protease $P^X$ while $PCS^X$ is cleaved by $P^X$;

(v) preparing a second plurality of host cells, each member of which comprises a third nucleic acid expression construct, encoding a non-diversified fusion protein comprising the structure:

$$N\text{-}PCS^*\text{-}degSig_N\text{-}M\text{-}PCS^\#\text{-}degSig_C\text{-}C;$$

wherein N represents the N-terminus, $PCS^\#$ is the sequence of $PCS^Y$ identified in step (iv), PCS* is a second protease cleavage site, which may or may not be identical to $PCS^X$, and which differs from $PCS^\#$ in at least one amino acid residue, $degSig_N$ represents a degradation signal, which promotes degradation of the fusion protein in the host cell if PCS* is cleaved by a protease such that the first residue of $degSig_N$ becomes the new N-terminus of the remaining fusion, M represents a cytoplasmic selection marker, and $degSig_C$ represents a second degradation signal, which promotes degradation of the fusion protein in a host cell if $PCS^\#$ is not cleaved by a protease, and C represents the C-terminus;

and wherein each member of said second plurality of host cells further comprises a member of a plurality of a fourth expression construct expressing protease variants of a protease P*, wherein said protease P* is capable of cleaving PCS* such that the first residue of $degSig_N$ becomes the new N-terminus of the remaining fusion, wherein said plurality of the fourth nucleic acid expression constructs further comprises a diversity in at least one amino acid position at the protease interface of said protease P* interacting with said first protease cleavage site PCS*, whereby the plurality of host cells is capable of simultaneously expressing the non-diversified fusion protein and said protease variants, and wherein the host cells promote degradation of the fusion protein via $degSig_N$, if $PCS^X$ is cleaved by a protease; and promote degradation of the fusion protein via $degSig_C$, if $PCS^\#$ is not cleaved by a protease;

(vi) cultivating the plurality of host cells of step (v) under conditions such that the fusion protein and the variants of protease $P^X$ are simultaneously expressed;

(vii) subjecting the plurality of host cells of step (vi) to selective conditions using the cognate selecting agent for the selection marker of the fusion protein encoded by the third nucleic acid expression construct; and (viii) identifying a cell, which has been positively selected in step (vii), and identifying P#, wherein P# is the sequence of the protease variant of the protease P* encoded by the fourth nucleic acid construct of the identified host cell, which protease variant P# is capable of cleaving the protease cleavage site variant PCS#, and which is incapable of cleaving the first cleavage site PCS*;

thereby obtaining orthogonal protease/protease cleavage site systems of a first PCS* and first protease P*, and a variant PCS# and a variant protease P#.

The present disclosure also provides variants of bdSUMO and bdSENP1, which have been identified by the methods of the present disclosure, and which exhibit improved properties over existing orthogonal protease/protease cleavage site-pairs, which are currently used with wild-type bdSUMO and wild-type bdSENP1. Specifically, the present disclosure provides a variant SUMO protease cleavage site (PCS), wherein said variant SUMO PCS comprises a C-terminal Gly-Gly, and, when fused to the N-terminus of MBP having the amino acid sequence of SEQ ID NO: 71, is cleaved more efficiently after the C-terminal Gly-Gly by a protease having the amino acid sequence of SEQ ID NO: 57 (MutB bdSENP1) as compared to cleavage by a protease having the amino acid sequence of SEQ ID NO: 7 (scUlp1) or SEQ ID NO: 8 (hsSENP2), when tested at the same concentration under standard conditions of 1 hour incubation at 21° C., an initial concentration of PCS-MBP fusion of 100 UM in a buffer consisting of 45 mM Tris/HCl PH 7.5, 250 mM NaCl, 2 mM $MgCl_2$, 250 mM sucrose, 10 mM DTT; optionally wherein the protease having the amino acid sequence of SEQ ID NO: 57 (MutB bdSENP1) cleaves an at least a 500-fold molar excess of the said SUMO PCS-MBP fusion at the above standard conditions.

Similarly, the present disclosure provides a variant protease, wherein said variant protease cleaves a protease cleavage site (PCS) having the amino acid sequence of SEQ ID NO: 41 (Mut1 bdSUMO), when fused to the N-terminus of MBP having the amino acid sequence of SEQ ID NO: 71, more efficiently after the C-terminal Gly-Gly than a protease cleavage site having the amino acid sequence of SEQ ID NO: 4 (scSUMO) fused to the N-terminus of SEQ ID NO: 71 or a protease cleavage site having the amino acid sequence of SEQ ID NO: 3 (hsSUMO) fused to the N-terminus of SEQ ID NO: 71, when tested at the same concentration under standard conditions of 1 hour incubation at 21° C., an initial concentration of PCS-MBP fusions of 100 μM in a buffer consisting of 45 mM Tris/HCl PH 7.5, 250 mM NaCl, 2 mM $MgCl_2$, 250 mM sucrose, 10 mM DTT; optionally wherein said variant protease cleaves an at least a 500-fold molar excess of the Mut1 bdSUMO-MBP fusion at the above standard conditions.

Finally, the present disclosure also provides a process of purifying a protein of interest, comprising the steps of (i) providing a protein of interest to be purified, wherein said protein comprises an affinity tag fused to said protein via a variant protease cleavage site according to the present disclosure;

(ii) binding the protein of step (i) to an affinity matrix via said affinity tag; and (iii) eluting the protein from the affinity matrix using a variant protease of the present disclosure; thereby purifying the protein.

SEQ ID NO: 6 consists of amino acids 248-481 of wild-type bdSENP1 (NCBI reference sequence XP_003567671.1) set forth in SEQ ID NO: 73; SEQ ID NO: 25 consists of amino acids 265-354 of wild-type bdSENP1 set forth in SEQ ID NO: 73; SEQ ID NOs: 26-40 are variants of SEQ ID NO: 25; and SEQ ID NOs: 56-70 are variants of SEQ ID NO: 6. Accordingly, unless indicated otherwise, the positions of amino acid mutations within bdSENP1 described herein refer to positions 269, 280, 346 and 350 (R269, N280, R346 and K350) of the amino acid sequence of wild-type bdSENP1 set forth in SEQ ID NO: 73. Said amino acid positions 269, 280, 346 and 350 of SEQ ID NO: 73 correspond to:

(i) amino acid positions 22, 33, 99 and 103 of SEQ ID NOs: 6 and 56-70, and (ii) amino acid positions 5, 16, 82 and 86 of SEQ ID NOs: 25-40.

DETAILED DESCRIPTION OF THE PREFERRED EMBODIMENTS

An In Vivo System to Select for New Protein Cleavage Sites and Proteases with Orthogonal Specifies The first part of this invention was to create an in vivo selection system in *E. coli* for evolving a SUMO-specific protease/SUMO protein pair to orthogonal specificity as compared to a reference SUMO-protease/substrate pair. This system can select at the same time "for" cleavage of one SUMO variant "X" and "against" the cleavage of another SUMO variant "Y". For that, we used the ssrA degradation signal (reviewed in Keiler 2008; Himeno et al. 2014), an N-end rule degron ($Degron^{NER}$) (Bachmair et al. 1986), and the hygromycin B phosphotransferase (HygB) that allows *E. coli* cells to survive in the presence of hygromycin B (Rao et al. 1983). During selection HygB is expressed as a $SUMO^Y$-$Degron^{NER}$-HygB-$SUMO^X$-ssrA fusion protein (FIG. 1).

The ssrA signal is a small peptide (AADENYALAA; SEQ ID NO: 2) that triggers rapid degradation of HygB, unless a co-expressed SUMO-specific protease cleaves $SUMO^X$ and thus disconnects the ssrA signal from the fusion protein. "$Degron^{NER}$" is a strong N-end-rule degradation signal (FLFVQ; SEQ ID NO: 1) (Wang et al. 2008) that remains silent in the fusion context, but gets activated if $SUMO^Y$ is cleaved by the co-expressed SUMO-specific protease. Thus, HygB is only stable and consequently the cells acquire hygromycin B resistance if the coexpressed SUMO-specific protease cleaves $SUMO^X$, but not $SUMO^Y$ (FIG. 1).

The functionality of the system was validated using the SUMO protein (bdSUMO) and its specific protease from *Brachypodium distachyon* (bdSENP1) (Frey & Görlich 2014a). Specifically, the selection system was tested by co-expressing an IPTG-inducible bdSENP1 with a series of different constitutively expressed $bdSUMO^{variant}$-Degron NER-HygB-bdSUMO-ssrA fusion proteins in *E. coli* (FIG. 2). Since the aim of the selection is to obtain protease variants that cleave $SUMO^X$ very efficiently and thus remove the C-terminal degron already at very low protease concentrations, a very weak ribosome-binding site (RBS) is used to initiate translation of the fusion protein. This weak RBS has the RNA sequence AAAACAAGUUAUCCAUG (SEQ ID NO: 72; with AUG being the start codon) and produces 50-fold less protein than a strong RBS. Cells were then tested for survival in a medium containing relevant amounts of hygromycin B and IPTG. As a positive control for a non-cleavable SUMO variant, we used bdSUMO*, in which the $P_1$ residue carried a protease-blocking mutation (Kuwata & Nakamura 2008). Indeed, cells survived in hygromycin B-containing medium only when both protein degradation signals were kept inactive, namely by the bdSENP1-mediated cleavage of the C-terminal bdSUMO and the nullrecognition of the N-terminal bdSUMO* (FIG. 2-B). These experiments clearly showed that our designed in vivo system was functional and appropriate for the selection of SUMO-specific proteases with orthogonal substrate specificity.

In more generic terms, the present disclosure thus provides a fusion protein with the structure N-PCS$^Y$-degSig$_N$-M-PCS$^X$-degSig$_C$-C;

wherein
N represents the N-terminus;
PCS$^Y$ and PCS$^X$ each represent a protease cleavage site (PCS), which differ from each other in at least one amino acid residue;
degSig$_N$ represents a degradation signal, which promotes degradation of the fusion protein in a host cell if PCS$^Y$ is cleaved by a protease such that the first amino acid of degSig$_N$ becomes the new N-terminus of the remaining fusion;
M represents a cytoplasmic selection marker; and
degSig$_C$ represents a second degradation signal, which promotes degradation of the fusion protein in a host cell if PCS$^X$ is not cleaved by a protease; and
C represents the C-terminus.

As used herein, the term "selection marker" is intended to mean a gene encoding a cytoplasmic protein, which upon introduction into a suitable host cell confers a trait to said host cell, which can be used for positive selection when subjecting the host cell under selective conditions. Suitable hosts are species/strains that recognize both degradations signals used and that do not contain endogenous PCS-specific proteases that would interfere with the assay, one example being *Escherichia coli* Top10 F'. The selection marker may be a gene, which confers prototrophy to auxotrophs, or resistance against an external chemical or physical stimulus, such that in the absence of said selection marker the host cell will not grow, when subjected to the external stimulus. In preferred embodiments, M is a cytoplasmic selection marker providing resistance against an antibiotic selection agent. Such marker is preferred over auxotrophy markers, because it does not require an auxotrophic strain and the stringency of selection can be titrated by applying low or high concentrations of antibiotics. Such antibiotic resistance markers are well-known in the art and used for stably maintaining plasmids in a prokaryotic host cell. Suitable markers include cytoplasmic proteins that inactivate or bypass otherwise toxic antibiotics. Examples are shown in the table below.

| Antibiotic | Gene | Enzyme | UniProt identifier |
|---|---|---|---|
| Hygromycin B | hph | Hygromycin B phosphotransferase | P00557 |
| Kanamycin | aphA1 | Aminoglycoside 3'-phosphotransferase I | P00551 |
| Streptomycin | srtB | Aminoglycoside O-phosphotransferase APH(6)-Id | C5IWK8 |
|  | aadA | Streptomycin 3"-adenylyltransferase | P0AG05 |
| Spectinomycin | aph | Spectinomycin phosphotransferase | O06916 |
|  | aadA | Streptomycin 3"-adenylyltransferase | P0AG05 |
| Zeocin | ble | Bleomycin-binding protein | Q7DJ53 |
| Trimethoprim | dfrA | Dihydrofolate reductase | Q81R22 |

Other selectable markers might work as well, provided they function in the selected host, they tolerate fusions to both termini and can become susceptible to cytoplasmic protein degradation. As exemplified herein, degSig$_N$ may comprise the amino acid sequence FLFVQ (Degron$^{NER}$; SEQ ID NO: 1), and/or degSig$_C$ may comprise the amino acid sequence AADENYALAA (ssrA; SEQ ID NO: 2). In a preferred embodiment, degSig$_N$ is FLFVQ (Degron$^{NER}$; SEQ ID NO: 1), and degSig$_C$ is AADENYALAA (ssrA; SEQ ID NO: 2).

Generally, the fusion protein of the present invention can be advantageously used to develop and identify orthogonal protease/protease cleavage site pairs and variants. Of particular interest herein are eukaryotic orthogonal protease/protease cleavage site pairs and variants, in particular orthogonal protease/protease cleavage site pairs and variants, which can be advantageously applied in mammalian cells. In general, any two PCSs may be tested for their orthogonality using the fusion protein of the present disclosure. In principle, there is no need for the two PCSs being particularly related to each other or to bdSUMO. However, in specific embodiments, PCS$^Y$ and/or PCS$^X$ are selected from the bdSUMO protease cleavage site shown in SEQ ID NO: 3, a paralog or an ortholog of bdSUMO, or a functionally equivalent variant of bdSUMO having at least 80% sequence identity over the full-length of SEQ ID NO: 3 (bdSUMO). Hence, one of PCS$^Y$ or PCS$^X$ may be the bdSUMO protease cleavage site shown in SEQ ID NO: 3. In other embodiments, PCS$^Y$ and/or PCS$^X$ may be a paralog or an ortholog of bdSUMO. Examples of such a paralog or ortholog include ubiquitin-related proteins such as NEDD8, Atg4, or ubiquitin itself. Other examples of a paralog or ortholog include SUMO proteins from other species, including yeast species and animal special, such as from mammalian species. In one particular embodiment, said SUMO paralog or ortholog is from *Saccharomyces cerevisiae* having the amino acid sequence shown in SEQ ID NO: 4 (scSUMO). In another particular embodiment, said SUMO paralog or ortholog is from *Homo sapiens* having the amino acid sequence shown in SEQ ID NO: 5 (hsSUMO2). As shown in the examples, although scSUMO or hsSUMO2 have a percentage identity as low as about 40% to the full length of SEQ ID NO: 3 (bdSUMO), these paralogs or orthologs still represent functional embodiments. Thus, in embodiments, the PCS has at least 40%, preferably at least 45%, more preferably at least 50%, more preferably at least 55%, more preferably at least 60%, more preferably at least 65%, more preferably at least 70%, more preferably at least 75%, and more preferably at least 80% sequence identity over the full length of SEQ ID NO: 3 (bdSUMO). In preferred embodiments, the PCS has at least 82%, preferably at least 84%, more preferably at least 86%, more preferably at least 88%, more preferably at least 90%, more preferably at least 92%, more preferably at least 94%, more preferably at least 96%, more preferably at least 98%, more preferably at least 99% sequence identity over the full length of SEQ ID NO: 3 (bdSUMO). At the same time PCS$^Y$ and PCS$^X$ differ from each other in at least one amino acid residue in the PCS interface interacting with the cognate protease of PCS$^X$. In general, there is no limitation in respect to the number of residues that can be diversified or randomised in the PCS. Hence, PCS$^Y$ and PCS$^X$ may differ from each other preferably in at least two amino acid residues in the PCS interface interacting with the cognate protease of PCS$^X$; more preferably in at least three amino acid residues in the PCS interface interacting with the cognate protease of PCS$^X$. As noted above, in principle, both PCS may be completely unrelated to each other, i.e. they differ in every amino acid residue.

As used herein, an amino acid sequence is said to have "X % sequence identity with SEQ ID NO: Y" over a defined length of amino acids if the sequence in question is aligned with said SEQ ID NO: Y and the sequence identity between those to aligned sequences is at least X %. Such an alignment can be performed using for example publicly available computer homology programs such as the "BLAST" program, such as "blastp" provided at the NCBI homepage at ncbi.nlm.nih.gov/blast/blast.cgi, using the default settings provided therein. Subsequently, identical residues are determined, such as by counting by hand, and a subsequent calculation of the percentage identity (PID) by dividing the number of identities over the indicated length of SEQ ID NO: Y gives "X % sequence identity". If a particular length is not specifically indicated, the sequence identity is calculated over the entire/full length of SEQ ID NO: Y. Further methods of calculating sequence identity percentages of sets of polypeptides are known in the art.

Likewise, the present disclosure further provides a nucleic acid construct, comprising a nucleic acid sequence coding for the fusion protein as described above. In specific embodiments, the nucleic acid construct comprises all regulatory sequences, which are required for controlling translation and transcription of the fusion protein in a desired host cell. Accordingly, in a preferred embodiment, the nucleic acid construct is an expression construct. Nucleic acid constructs and expression constructs are well-known to the skilled person, and its components will be selected in accordance with the host cell in question. Usually they will further comprise an origin of replication, which is functional for the required purpose, and a selectable marker, in order to stably maintain the nucleic acid construct or expression construct, in case it is in the form of a plasmid.

The nucleic acid construct may be diversified at $PCS^Y$ and/or $PCS^X$, which allows that several constructs can be tested simultaneously to identify pairs of protease cleavage sites in which $PCS^X$ is cleaved, and $PCS^Y$ is not cleaved, by positive selection. Accordingly, the present disclosure further provides a nucleic acid expression construct library, comprising a plurality of diversified nucleic acid expression constructs according to the present disclosure, wherein the nucleic acid encoding $PCS^Y$ of the fusion protein comprises a diversity such that in the encoded $PCS^Y$ at least one amino acid position, preferably at least two encoded amino acid positions, more preferably at least three encoded amino acid positions, such as at least four encoded amino acid positions, in particular at least five encoded amino acid positions may be diversified. Of course, the strongest effects of mutations will be observed in those residues, which are in the interface between the PCS and its cognate protease. Accordingly, usually, the amino acid position(s) comprising the diversity is/are position(s) within the $PCS^Y$ interface interacting with a protease of interest capable of cleaving the unmodified, non-diversified parent $PCS^Y$. The diversity may be introduced by site-directed mutagenesis, e.g. by using diversified PCR primer, or by random mutagenesis. At the same time, such diversified PCS may be selected for other properties such as improved expression, folding, or solubility. In case of the bdSUMO PCS, preferred positions for introducing diversity are T60, D67, and/or Q75.

In order to take effect, or probably only to propagate the nucleic acid (expression) construct or the of the nucleic acid expression construct library, the construct or construct library needs to be introduced into a host cell, using routine methods in the art. The result is a plurality of host cells, wherein each host cell comprises a nucleic acid expression construct according to the present disclosure, which is not diversified. In the case of a nucleic acid expression construct library, each member of the plurality of cells will ideally comprise one member of the diversified nucleic acid expression construct library.

The host cell may be any cell, which is either suitable for propagating the nucleic acid expression construct, or—more preferably—any host cell, which is capable of expressing the nucleic acid expression construct of the present disclosure, and wherein the host cell promotes degradation of the fusion protein via $degSig_N$, if $PCS^Y$ is cleaved by a protease; and promotes degradation of the fusion protein via $degSig_C$, if $PCS^X$ is not cleaved by a protease (i.e. the host cell must be compatible with the degradation signals $degSig_N$ and $degSig_C$). Thus, suitable hosts are species/strains that recognize both degradations signals used and that do not contain endogenous PCS-specific proteases that would interfere with the assay, one example being *Escherichia coli* Top10 F'. Accordingly, the host cell may be a prokaryotic cell, such as a bacterial cell. In the context of a SUMO PCS, the host cell may preferably be an *E. coli* host cell. For screening purposes, it is advantageous that the host cell does not itself express an endogenous protease relevant to the PCS. However, to screen for the effect of a particular (exogenous) protease on the PCSs of the constructs, it is preferred that the host cells are capable of simultaneously expressing a protease of interest and the fusion protein encoded by the nucleic acid expression construct. Preferably said protease of interest is capable of cleaving $PCS^X$. The nucleic acid expression construct of the protease may be under the control of an inducible promoter. Inducible promoters are known to the skilled person, and are generally distinguished into physically inducible promoters and chemically inducible promoters. Physically inducible promoters are promoters, which may be sensitive to temperature or light. Chemically inducible promoters include the Tet-on or Tet-off system, promoters, which are inducible by metal ions, or the Lac- and Tac-gene promoters. Preferably the inducible promoter is inducible by IPTG, as in the examples used herein, and requires the presence of a lacI gene within the host and/or on the plasmids of the selection system. The expression construct expressing the fusion protein of the present disclosure, and the expression construct expressing the protease of interest should have compatible origins of replication and different selectable markers, in order to ensure that both constructs are maintained in the host cell.

Vice versa, it is also possible to screen for a mutant protease, which is capable of cleaving $PCS^X$ but not $PCS^Y$. In this context, the present disclosure also provides a plurality of host cells, wherein each member of the plurality of host cells comprises a first non-diversified nucleic acid expression construct encoding a fusion protein of the present disclosure, and a member of a plurality of second expression constructs encoding a diversified protease of interest. In this case, said plurality of second expression constructs is derived from a first protease capable of cleaving $PCS^Y$ of the fusion protein of the first expression construct, and a member of the plurality of the host cells will ideally comprise a single member of the plurality of the diversified second nucleic acid expression constructs encoding a mutant protease. The host cells are capable of simultaneously expressing said diversified protease of interest and the fusion protein encoded by said first expression construct. The plurality of second expression constructs comprises a diversity in at least one amino acid position at the protease interface interacting with said $PCS^Y$, preferably in at least two amino acid positions at the protease interface interacting with said $PCS^Y$, more preferably in at least three amino acid positions at the protease interface interacting with said $PCS^Y$, more preferably in at least four amino acid positions at the protease interface interacting with said $PCS^Y$, and most preferably in at least five amino acid positions at the protease interface interacting with said $PCS^Y$. The diversity may be introduced by site-directed mutagenesis, e.g. by using diversified PCR primer, or by random mutagenesis, using routine methods in the art. At the same time, such diversified proteases may be selected for other properties such as improved expression, folding, solubility, (temperature) stability, and/or increased activity. In case of bdSENP1, the preferred positions for introducing diversity comprise, for example, the positions corresponding to N280, R346, K350, and/or R269 of SEQ ID NO: 73.

In light of the foregoing, the present disclosure provides a method for simultaneously testing whether (a) a first protease cleavage site $PCS^Y$ is not cleaved by a protease of interest, and (b) whether a second protease cleavage site $PCS^X$ is cleaved by said protease of interest, comprising the steps of
  (i) providing a host cell comprising a first nucleic acid construct according to the present disclosure and a second expression construct for expression of a protease of interest, wherein the host cell is capable of simultaneously expressing the fusion protein and said protease of interest, and wherein the host cell promotes degradation of the fusion protein via $degSig_N$, if $PCS^Y$ is cleaved by a protease, and promotes degradation of the fusion protein via $degSig_C$, if $PCS^X$ is not cleaved by a protease;
  (ii) cultivating the host cell of step (i) under conditions such that the fusion protein and the protease of interest are simultaneously expressed; and
  (iii) subjecting the host cell of step (ii) to selective conditions using the cognate selecting agent for the selection marker of the fusion protein encoded by the first nucleic acid construct;
wherein growth of the host cell in the presence of the selective conditions applied in step (iii) indicates that the first protease cleavage site $PCS^Y$ is not cleaved by said protease of interest, and that said second protease cleavage site $PCS^X$ is cleaved by said protease of interest of said second nucleic acid expression construct. As set out above, the cytoplasmic selection marker may advantageously confer antibiotic resistance to the host cell, thereby positively selecting those cells in which the protease of interest cleaves $PCS^X$ but not $PCS^Y$.

Likewise, the present disclosure also provides a method for identifying a protease cleavage site variant $PCS^Y$ of a first protease cleavage site $PCS^X$, wherein $PCS^Y$ is not cleaved by a protease of interest, comprising the steps of
  (i) providing a plurality of host cells, wherein each member of said plurality of host cells comprises a member of a plurality of first nucleic acid constructs according to the present disclosure, with the plurality of first nucleic acid constructs encoding a diversified variant $PCS^Y$ of a first protease cleavage site $PCS^X$, and a second expression construct for expression of a protease of interest, wherein said protease of interest is capable of cleaving $PCS^X$, whereby the plurality of host cells is capable of simultaneously expressing the fusion protein encoded by the first nucleic acid construct and said protease of interest, and wherein the host cell promotes degradation of the fusion protein via $degSig_N$, if $PCS^Y$ is cleaved by a protease, and promotes degradation of the fusion protein via $degSig_C$, if $PCS^X$ is not cleaved by a protease;
  (ii) cultivating the plurality of host cells of step (i) under conditions such that the fusion protein and the protease of interest are simultaneously expressed; and
  (iii) subjecting the plurality of host cells of step (ii) to selective conditions using the cognate selecting agent for the selection marker of the fusion protein encoded by the plurality of first nucleic acid constructs; and
  (iv) identifying a host cell, which has been positively selected in step (iii), and identifying the sequence of $PCS^Y$ of the first nucleic acid construct of the identified host cell, which $PCS^Y$ is a protease cleavage site variant of a first protease cleavage site $PCS^X$, and which $PCS^Y$ is not cleaved by said protease of interest of the second expression construct.

Moreover, the present disclosure provides a method for identifying a protease variant, which is capable of cleaving a protease cleavage site variant $PCS^X$ of a first protease cleavage site $PCS^Y$, but not the first protease cleavage site $PCS^Y$, wherein said protease variant is derived from a first protease, which is capable of cleaving the first protease cleavage site $PCS^Y$, but not the protease cleavage site variant $PCS^X$, comprising the steps of
  (i) providing a plurality of host cells, wherein each member comprises a non-diversified first nucleic acid expression construct according to the present disclosure, in which $PCS^X$ is a protease cleavage site variant of a first protease cleavage site $PCS^Y$, wherein the $PCS^Y$ is cleaved by a first protease of interest and $PCS^X$ is not cleaved by said first protease; and wherein each member of said plurality of host cells further comprises a member of a plurality of a second expression construct expressing protease variants of said first protease of interest, wherein said plurality of second nucleic acid expression constructs comprises a diversity in at least one amino acid position at the protease interface interacting with said first $PCS^Y$, whereby the plurality of host cells is capable of simultaneously expressing the fusion protein and said protease of interest, and wherein the host cell promotes degradation of the fusion protein via $degSig_N$, if $PCS^Y$ is cleaved by a protease, and promotes degradation of the fusion protein via $degSig_C$, if $PCS^X$ is not cleaved by a protease;
  (ii) cultivating the plurality of host cells of step (i) under conditions such that the fusion protein and the protease of interest are simultaneously expressed; and
  (iii) subjecting the plurality of host cells of step (ii) to selective conditions using the cognate selecting agent for the selection marker of the fusion protein encoded by the first nucleic acid expression construct;
  (iv) identifying a host cell, which has been positively selected in step (iii), and identifying the sequence of the protease variant encoded by the second nucleic acid construct of the identified host cell, wherein the protease variant is capable of cleaving a protease cleavage site variant $PCS^X$ of a first protease cleavage site $PCS^Y$, but incapable of cleaving the first protease cleavage site $PCS^Y$.

Both methods can suitably be combined to identify a new orthogonal protease (P)/protease cleavage site (PCS) system. Accordingly, the present disclosure further provides a method of preparing an orthogonal protease (P)/protease cleavage site (PCS) system, comprising the steps of
  (i) providing a plurality of host cells, wherein each member of said plurality of host cells comprises a member of a plurality of first nucleic acid constructs according to the present disclosure, which encodes a diversified variant $PCS^Y$ of a first protease cleavage site $PCS^X$, and a second expression construct for expression of a first protease $P^X$ of interest, which is capable of cleaving $PCS^X$, whereby the plurality of host cells is capable of simultaneously expressing the fusion protein and said first protease of interest, and wherein the host cells promote degradation of the fusion protein via degSig$_N$, if PCS$^Y$ is cleaved by a protease; and promote degradation of the fusion protein via degSig$_C$, if PCS$^X$ is not cleaved by a protease;

(ii) cultivating the plurality of host cells of step (i) under conditions such that the fusion protein and the first protease P$^X$ are simultaneously expressed; and (iii) subjecting the plurality of host cells of step (ii) to selective conditions using the cognate selecting agent for the selection marker of the fusion protein encoded by the plurality of first nucleic acid constructs;

(iv) identifying a host cell, which has been positively selected in step (iii), and identifying PCS$^\#$, wherein PCS$^\#$ is the sequence of the PCS$^Y$ from the first nucleic acid construct of the identified host cell, wherein PCS$^\#$ is a protease cleavage site variant of a first protease cleavage site PCS$^X$, and wherein PCS$^\#$ is not cleaved by said first protease P$^X$ while PCS$^X$ is cleaved by P$^X$;

(v) preparing a second plurality of host cells, which comprise a third nucleic acid expression construct, encoding a non-diversified fusion protein comprising the structure:

N-PCS*-degSig$_N$-M-PCS$^\#$-degSig$_C$-C;

wherein N represents the N-terminus, PCS$^\#$ is the sequence of PCS$^Y$ identified in step (iv), PCS* is a second protease cleavage site, which may or may not be identical to PCS$^X$, and which differs from PCS$^\#$ in at least one amino acid residue, degSig$_N$ represents a degradation signal, which promotes degradation of the fusion protein in the host cell if PCS* is cleaved by a protease such that the first amino acid of degSig$_N$ becomes the new N-terminus of the remaining fusion, M represents a cytoplasmic selection marker, and degSig$_C$ represents a second degradation signal, which promotes degradation of the fusion protein in a host cell if PCS$^\#$ is not cleaved by a protease, and C represents the C-terminus;

and wherein each member of said second plurality of host cells further comprises a member of a plurality of a fourth expression construct expressing protease variants of a protease P*, wherein said protease P* is capable of cleaving PCS* such that the first amino acid of degSig$_N$ becomes the new N-terminus of the remaining fusion, wherein said plurality of the fourth nucleic acid expression constructs comprises a diversity in at least one amino acid position at the protease interface of said protease P* interacting with said first protease cleavage site PCS*, whereby the plurality of host cells is capable of simultaneously expressing the non-diversified fusion protein and said protease variants, and wherein the host cells promote degradation of the fusion protein via degSig$_N$, if PCS* is cleaved by a protease; and promote degradation of the fusion protein via degSig$_C$, if PCS* is not cleaved by a protease;

(vi) cultivating the plurality of host cells of step (v) under conditions such that the fusion protein and the variants of protease P* are simultaneously expressed;

(vii) subjecting the plurality of host cells of step (vi) to selective conditions using the cognate selecting agent for the cytoplasmic selection marker M of the fusion protein encoded by the third nucleic acid expression construct; and (viii) identifying a cell, which has been positively selected in step (vii), and identifying P$^\#$, wherein P$^\#$ is the sequence of the protease variant of protease P* encoded by the fourth nucleic acid construct of the identified host cell, which protease variant P$^\#$ is capable of cleaving the protease cleavage site variant PCS$^\#$, and which is incapable of cleaving the first cleavage site PCS$^X$;

thereby obtaining orthogonal protease/protease cleavage site systems of a PCS* and a protease P*, and a variant PCS$^\#$ and a variant protease P$^\#$.

bdSUMO$^{Mut1}$, a Highly Cleavage-Resistant SUMO Protein Mutant

Applying the above-disclosed methods, the second achievement of our work was to evolve a new SUMO mutant that is not cleaved by the SUMOstar protease. We chose SUMOstar as a reference protease, because it is the so far most promiscuous SUMO-protease, accepting not only all so far tested wild SUMOs, but also the SUMOstar mutant as a substrate (see Table 1, FIG. 14 and FIG. 15). Selection for SUMOstar protease-resistance therefore appeared to be the most stringent criterion for evolving widely orthogonal SUMO variants.

We chose as a starting point bdSUMO, because this variant is cleaved by Ulp1 and the SUMOstar protease already ≈10-fold less efficiently than that S. cerevisiae SUMO-fusions (Frey & Görlich 2014b).

In order to create bdSUMO mutants that are not cleaved by SUMOstar protease, residues T60, D67 and Q75 (numbering according to the full-length SUMO protein) were randomized (see FIG. 3). These three mutagenized positions were chosen since they might be located in the bdSENP1-interacting interface according to a multiple sequence alignment using the information of already crystalized SUMO·SUMO-specific protease complexes (Xu et al. 2006; Reverter & Lima 2006; Shen et al. 2006; Reverter & Lima 2004). Nevertheless, there was no experimental structural information for the SUMO/SENP1 complex from Brachypodium distachyon that would have helped us for the rational design of the SUMO mutants and therefore predict the desired mutations.

The randomization of the three residues resulted in a bdSUMO mutant library (bdSUMO$^{MutX}$) that was then cloned as a bdSUMO$^{MutX}$-Degron$^{NER}$-HygB-SUMOstar-ssrA fusion protein to screen against bdSUMO$^{MutX}$ cleavage by the SUMOstar protease (FIG. 3-A). After selection, 10 different colonies were selected and their SUMO sequences were determined. All colonies had a strong preference for the D67K mutation and considerable amino acid variability in the other two mutagenized positions (FIG. 3-B). Cells expressing bdSUMO$^{Mut1}$ fused to HygB (bdSUMO$^{Mut1}$-degronNER-HygB-SUMOstar-ssrA) showed the best bacterial survival in the presence of hygromycin B compared to all other 9 bdSUMO mutants when SUMOstar protease was co-expressed after the addition of IPTG. bdSUMO$^{Mut1}$, which is not cleaved by SUMOstar protease, comprises the mutations T60K, D67K and Q75R and is the first element of our invention named the SUMOvera system. Detailed analyses revealed, however, that the D67K mutation alone was necessary and sufficient for blocking cleavage not only by the SUMOstar protease but also for other SUMO-specific proteases such as bdSENP1, Ulp1 and hsSENP2 (see FIG. 5, FIG. 15 and Table 1). The T60K and Q75R mutations will become crucial later on.

bdSENP1$^{MutB}$, a Protease Mutant that Cleaves bdSU-MO$^{Mut1}$ but not Wild Type SUMO Proteins As described above, our invention also includes the creation of a bdSENP1 protease mutant that cleaves bdSU-MO$^{Mut1}$ but not SUMOstar. To obtain such mutant, four residues of bdSENP1 (corresponding to R269, N280, R346 and K350 of SEQ ID NO: 73) were randomly mutagenized. These four residues were selected since they might interact with the residues mutated in bdSUMO (based on the multiple sequence alignment mentioned above). In order to select for the desired bdSENP1 mutant, we used our designed in vivo selection method.

The construct used during the screen was a SUMOstar-Degron NER-HygB-bdSUMO$^{Mut1}$-ssrA fusion (FIG. 4-A). SUMOstar was placed at the N-terminus of HygB to select against protease cleavage, whereas bdSUMO$^{Mut1}$ was cloned at the C-terminus to select for efficient protein cleavage by a prospective bdSENP1 mutant.

The bdSENP1 mutant library (bdSENP1$^{MutX}$) was cloned behind an IPTG-controlled promoter and the already mentioned weak ribosome-binding site, transformed into E. coli containing the SUMOstar-Degron$^{NER}$-HygB-bdSUMO$^{Mut1}$-ssrA reporter, and cells were then plated on hygromycin B-containing medium. Twenty different hygromycin B-resistant mutants were selected, sequenced, and re-screened for hygromycin B resistance at low and high expression levels of the protease. Six mutants were positive during re-rescreening, namely bdSENP1$^{MutA}$ (carrying the R269P, N280G, R346E and K350P mutations at the positions corresponding to amino acid residues R269, N280, R346 and K350 of wild-type bdSENP1 set forth in SEQ ID NO: 73), bdSENP1$^{MutB}$ (N280S, R346E at the positions corresponding to amino acid residues N280 and R346 of wild-type bdSENP1 set forth in SEQ ID NO: 73), bdSENP1$^{MutC}$ (R269S, N280A, R346G and K350V at the positions corresponding to amino acid residues R269, N280, R346 and K350 of wild-type bdSENP1 set forth in SEQ ID NO: 73), bdSENP1$^{MutD}$ (R269P, N280E, R346E and K350Q at the positions corresponding to amino acid residues R269, N280, R346 and K350 of wild-type bdSENP1 set forth in SEQ ID NO: 73), bdSENP1$^{MutE}$ (N280G, R346Y, K350A at the positions corresponding to amino acid residues N280, R346 and K350 of wild-type bdSENP1 set forth in SEQ ID NO: 73) and bdSENP1$^{MutF}$ (R269P, N280C, R346L, K350R at the positions corresponding to amino acid residues R269, N280, R346 and K350 of wild-type bdSENP1 set forth in SEQ ID NO: 73) (FIG. 4-B). These results suggest that changing the residues corresponding to N280 and R346 of SEQ ID NO: 73 is key for switching the selectivity of the protease towards bdSUMO$^{Mut1}$-fusion proteins. Moreover, the high variability in the mutagenized residues among all bdSENP1 mutants clearly indicates that there are several solutions to the problem, and none of the discovered solutions had been predictable from previous structural or sequence information.

The re-screening identified bdSENP1$^{MutB}$ (carrying just the N280S and R346E mutations) as the best mutant. When bdSENP1$^{MutB}$ was co-expressed with the HygB reporter construct, essentially the same level of hygromycin B resistance was observed as for cells that expressed HygB without degradation signals. We therefore decided to characterize bdSENP1$^{MutB}$ in more detail. It represents the second element of the novel SUMOvera system.

A first in vitro protein cleavage tests showed that the T60K and Q75R mutations of the bdSUMO$^{Mut1}$ protein are required for an efficient cleavage by the bdSENP1$^{MutB}$ protease (FIG. 5). The bdSENP1$^{MutB}$ protease is extremely active on bdSUMO$^{Mut1}$-fusion proteins as it is able to cleave a 500-fold molar excess of substrate within one hour at 0° C. (FIG. 6). In fact, this protease has a 100 times higher activity as compared to the commonly used TEV protease (see Example 1).

Although bdSENP1$^{MutB}$ was selected only against cleavage of SUMOstar, exhaustive protein cleavage assays proved that not only SUMOstar but also wild type scSUMO and human SUMO-2 (hsSUMO2) fusion proteins remain intact even in the presence of extremely high concentration of bdSENP1$^{MutB}$ (see FIG. 14 and Example 2). Moreover, the cleavage assays also revealed that bdSUMO$^{Mut1}$ fusions are highly resistant towards bdSENP1, Ulp1, hsSENP2 and the SUMOstar protease (see Table 1, FIG. 15 and Example 2). We therefore can conclude that our selection strategy was effective, and that both components of the SUMOvera system (bdSUMO$^{Mut1}$/bdSENP1$^{MutB}$) are orthogonal to virtually any other SUMO/SUMO protease system.

Applications of the SUMOvera System in Eukaryotic Hosts

Another aspect of this invention is the utility of the SUMOvera system in eukaryotic hosts. Unlike E. coli, eukaryotes possess endogenous SUMO-specific proteases, and consequently the expression of SUMO-tagged proteins in eukaryotic hosts results in a pre-mature cleavage of the SUMO fusions. In contrast to scSUMO and bdSUMO, bdSUMO$^{Mut1}$ remains stable as a fusion protein if over-expressed in S. cerevisiae (Example 3) or even after hours of incubation in various eukaryotic cellular lysates (derived from plants, frog eggs, human or insect cells, see Example 4). In fact, bdSUMO$^{Mut1}$-fusions are more stable than SUMOstar-fusions.

The two components of the SUMOvera system enable the expression, purification and efficient tag-removal of recombinant proteins expressed either in E. coli or in a eukaryotic host. The system also enables the protein purification by the "affinity capture and proteolytic release strategy" as described in (Frey & Görlich 2014b). In combination with an N-terminal His-tag, bdSUMO$^{Mut1}$-tagged proteins can be over-expressed in E. coli or yeast and further purified using a nickel chelate matrix. During protein purification, bdSU-MO$^{Mut1}$-fusion proteins can be eluted by on-column cleavage using bdSENP1$^{MutB}$ protease in order to achieve a higher degree of purity compared to standard elution methods. As an example, the present invention provides the evidence that the SUMOvera system together with the SUMOstar system, allows the purification of untagged and stoichiometric hetero-dimeric protein complexes in S. cerevisiae (Example 5).

This invention also shows the feasibility to perform site-specific proteolysis in vivo by overexpressing the bdSENP1$^{MutB}$ protease in S. cerevisiae without interfering with cell viability. Site-specific proteolysis of fusion proteins by several proteases has been used in living cells for various biochemical assays (Chen et al. 2010; Harder et al. 2008; Sato & Toda 2007). The cleavage of a fusion protein in vivo requires that a specific protease is expressed ectopically only at a given time. Over-expression of Ulp1, bdSENP1 or SUMOstar protease in e.g. S. cerevisiae is lethal, probably because of an induced massive de-sumoylation of essential SUMO-conjugates. In contrast, bdSENP1$^{MutB}$ protease can be over-expressed in a eukaryotic host without causing cellular death (Example 6), obviously because endogenous SUMO-conjugates are not recognized by this protease variant. In addition, it is well possible that the bdSENP1$^{MutB}$ protease could be also used in Hela cells (and perhaps in other eukaryotic systems) since hsSUMO2 is also not cleaved by this protease (FIG. 14).

Alternative Parts of the SUMOvera System

We have characterized extensively how a specific group of mutations in bdSUMO and bdSENP1 gave rise to the novel features of the two components SUMOvera system. However, it was unknown whether different sets of mutations at the same positions could also lead to the same results as only very small populations of bdSUMO and bdSENP1 mutants were analyzed and characterized after selection. We therefore decided to investigate whether it was possible to isolate more bdSUMO mutants that have the same or similar properties as bdSUMO$^{Mut1}$.

To do so, a library of bdSUMO with randomized mutations at residues T60, D67 and Q75 was screened by phage display to select mutants that are cleaved by the bdSENP1$^{MutB}$ protease and not by Ulp1 and hsSENP2. After selection, we analyzed a large population of bdSUMO mutants and observed that the mutation D67K was extremely dominant proving its vital role to achieve cleavage resistance against wild type protease (FIG. 12-A). Even though the mutations at positions T60 and Q75 were highly variable, we observed that certain residues were more frequent than others, suggesting some preference for certain residues to achieve efficient cleavage by the bdSENP1$^{MutB}$ protease (FIG. 12-A).

In order to test the efficiency of those preferred residues, we created and further tested in vitro several bdSUMO mutants with different combinations of the most frequent mutations (FIG. 12-B). The in vitro experiments confirmed that all tested combinations of mutations conferred cleavage resistance against wild type proteases as well as efficient recognition by the bdSENP1$^{MutB}$ (see Table 1 and FIG. 15).

In a next experiment, we decided to analyze whether the mutations in bdSENP1$^{MutB}$ would be the only set of mutations possible to achieve an efficient cleavage of bdSUMO$^{Mut1}$. To do so, we used the already described in vivo selection system to co-express a bdSENP1 library (bdSENP1$^{MutX}$) together with the reporter fusion protein scSUMO-Degron$^{NER}$-HygB-SUMO$^{Mut1}$-ssrA (FIG. 13-A). After selection, the sequence analysis of 96 different hygromycin B resistance colonies showed the presence of nine different bdSENP1 mutants. Interestingly, these nine mutants did not converge to a consensus sequence. Instead, rather different sets of mutations appear to achieve the same shift in substrate specificity of the protease (FIG. 13-B). Conversely, however, only a very small fraction of the 160,000 possible residue combinations appears to be effective.

We tested five of the newly identified bdSENP1 mutants in detail and found four of them (MutG, H, J, i and K) to cleave bdSUMO$^{Mut1}$-fusions as effectively or even more effectively than the earlier described SENP1$^{MutB}$ (Table 1 and FIG. 15). The same assay also revealed that several alternative bdSUMO mutants (Mut10, 11, 13, 15) were highly efficient substrates for at least some of these new bdSENP1 mutants (Table 1 and FIG. 15).

In a last aspect of this disclosure, we provide the evidence that mutations in bdSUMO$^{Mut1}$ (T60K, D67K and Q75R) and bdSUMO$^{Mut11}$ (T60S, D67K and Q75W) can be transplanted to other SUMO orthologs and then confer cleavage resistance against wild type proteases. Mutations in scSUMO (D61, D68 and Q76) and hsSUMO2 (R61, D68 and D76) allowed cleavage resistance against Ulp1, SUMO-star protease, hsSENP2 and bdSENP1 (FIG. 14). Moreover, the bdSENP1$^{MutB}$ protease was able to recognize scSUMO and hsSUMO2 carrying the bdSUMO$^{Mut1}$ exchanges more efficiently than the corresponding wild type scSUMO and hsSUMO2 proteins (FIG. 14, lower panel).

In more generic terms, the present disclosure thus provides a variant SUMO protease cleavage site (PCS), wherein said variant SUMO PCS comprises a C-terminal Gly-Gly, and, when fused to the N-terminus of MBP having the amino acid sequence of SEQ ID NO: 71, is cleaved more efficiently after the C-terminal Gly-Gly by a protease having the amino acid sequence of SEQ ID NO: 57 (MutB bdSENP1) as compared to cleavage by a protease having the amino acid sequence of SEQ ID NO: 7 (scUlp1) or SEQ ID NO: 8 (hsSENP2), when tested at the same concentration under standard conditions of 1 hour incubation at 21° C., an initial concentration of PCS-MBP fusion of 100 µM in a buffer consisting of 45 mM Tris/HCl PH 7.5, 250 mM NaCl, 2 mM MgCl$_2$, 250 mM sucrose, 10 mM DTT. Efficiency of the cleavage can be read out using routine procedures, for example HPLC and 'under the curve integration', or SDS-PAGE followed by Coomassie staining and measuring the gel with a densitometer. In a preferred embodiment, the protease having the amino acid sequence of SEQ ID NO: 57 (MutB bdSENP1) cleaves an at least a 500-fold molar excess of the said SUMO PCS-MBP fusion at the above standard conditions. In an even more preferred embodiment, the protease having the amino acid sequence of SEQ ID NO: 57 (MutB bdSENP1) cleaves an at least a 1000-fold molar excess of the said SUMO PCS-MBP fusion at the above standard conditions.

In embodiments, said variant SUMO PCS has at least 80% sequence identity over the full-length of SEQ ID NO: 3 (bdSUMO), or said variant SUMO PCS is a mutant paralog or a mutant ortholog of the bdSUMO protease cleavage site shown in SEQ ID NO: 3, wherein said variant SUMO protease cleavage site, when aligned to the full-length sequence of SEQ ID NO: 3, comprises a substitution at the position corresponding to D67 of the aligned SEQ ID NO: 3, wherein the amino acid at said position is substituted by a another amino acid selected from the group consisting of K, R, N, A and H; preferably wherein said amino acid is selected from the group consisting of K and R; in particular wherein said amino acid is K. Examples of a paralog or ortholog include ubiquitin-related proteins such as NEDD8, Atg4, or ubiquitin itself. Other examples of a paralog or ortholog include SUMO proteins from other species, including yeast species and animal special, such as from mammalian species. In one particular embodiment, said SUMO paralog or ortholog is from *Saccharomyces cerevisiae* having the amino acid sequence shown in SEQ ID NO: 4 (scSUMO). In another particular embodiment, said SUMO paralog or ortholog is from *Homo sapiens* having the amino acid sequence shown in SEQ ID NO: 5 (hsSUMO2). As shown in the examples, although scSUMO or hsSUMO2 have a percentage identity as low as about 40% to the full length of SEQ ID NO: 3 (bdSUMO), these paralogs or orthologs still form the basis of functional embodiments. Thus, in embodiments, the PCS has at least 40%, preferably at least 45%, more preferably at least 50%, more preferably at least 55%, more preferably at least 60%, more preferably at least 65%, more preferably at least 70%, more preferably at least 75%, and more preferably at least 80% sequence identity over the full length of SEQ ID NO: 3 (bdSUMO). In preferred embodiments, the variant protease cleavage site has at least 82%, preferably at least 84%, more preferably at least 86%, more preferably at least 88%, more preferably at least 90%, more preferably at least 92%, more preferably at least 94%, more preferably at least 96%, more preferably at least 98%, more preferably at least 99% sequence identity over the full length of SEQ ID NO: 3 (bdSUMO).

In addition, said variant protease cleavage site, when aligned to the full-length sequence of SEQ ID NO: 3, may further comprises a substitution at the position corresponding to Q75 of the aligned SEQ ID NO: 3, wherein the amino acid at said position is substituted by a another amino acid selected from the group consisting of R, W, A, H, M, I, P, and F; preferably wherein said amino acid is selected from the group consisting of R, W, A, and H. Alternatively to a substitution at a position corresponding to Q75, or in addition to said variant protease cleavage site, when aligned to the full-length sequence of SEQ ID NO: 3, may further comprises a substitution at the position corresponding to T60 of the aligned SEQ ID NO: 3, wherein the amino acid at said position is substituted by another amino acid selected from the group consisting of S, N, OK, P, H, R, and Q; preferably wherein said amino acid is selected from the group consisting of OS, N, K, and P. In view of the above, the present disclosure particularly contemplates embodiments, wherein said variant protease cleavage site comprises a combination of substitutions selected from the group consisting of (i) 67K, 60K, 75R (Mut1); (ii) 67K, 60P, 75W (Mut8); (iii) 67K, 75R (Mut10); (iv) 67K, 60S, 75H (Mut11); (v) 67K, 60S, 75W (Mut12); (vi) 67K, 60S, 75A (Mut13); (vii) 67K, 60N, 75W (Mut14); and (viii) 67K, 60N, 75A (Mut15), wherein the number indicates the amino acid in the variant SUMO PCS corresponding to the indicated position in SEQ ID NO: 3.

In a particularly preferred embodiment, the variant protease cleavage site has the amino acid sequence of SEQ ID NO: 3 (bdSUMO), except for the substitution D67K, optionally, if present, in combination with the additional substitutions at position T60 and/or Q75, as further described above. In certain embodiments, said additional substitution comprises an amino acid selected from the group consisting of Q75R, Q75W, Q75A, Q75H, Q75M, Q75I, Q75P, and Q75F; preferably wherein said substitution is selected from the group consisting of Q75R, Q75W, Q75A, and Q75H. In further embodiments, said additional substitution comprises an amino acid selected from the group consisting of T60S, T60N, T60K, T60P, T60H, T60R, and T60Q; preferably wherein said substitution is selected from the group consisting of T60S, T60N, T60K, and T60P. In particular embodiments, said variant protease cleavage site comprises a combination of substitutions selected from the group consisting of (i) D67K, T60K, Q75R (Mut1); (ii) D67K, T60P, Q75W (Mut8); (iii) D67K, Q75R (Mut10); (iv) D67K, T60S, Q75H (Mut11); (v) D67K, T60S, Q75W (Mut12); (vi) D67K, T60S, Q75A (Mut13); (vii) D67K, T60N, Q75W (Mut14); and (viii) D67K, T60N, Q75A (Mut15). In specific embodiments, the variant protease cleavage site has an amino acid sequence selected from SEQ ID NO: 41-55.

As noted above, the variant protease cleavage site may be a mutant, paralog or ortholog of the bdSUMO protease cleavage site shown in SEQ ID NO: 3, wherein said variant protease cleavage site, when aligned to the full-length sequence of SEQ ID NO: 3, comprises a substitution at the position corresponding to D67 of the aligned SEQ ID NO: 3, wherein the amino acid at said position is substituted by another amino acid selected from the group consisting of K, R, N, A and H; preferably wherein said amino acid is selected from the group consisting of K and R; in particular wherein said amino acid is K. In one particular embodiment, said SUMO ortholog is from *Saccharomyces cerevisiae* having the amino acid sequence shown in SEQ ID NO: 4 (scSUMO), specifically wherein SEQ ID NO: 4 comprises the substitution D68K, optionally in combination with Q76W or Q76R, and/or D61K or D61S. In a preferred embodiment said SUMO ortholog is from *Saccharomyces cerevisiae* having the amino acid sequence shown in SEQ ID NO: 4 (scSUMO), which comprises the combination of D61K, D68K, and Q75R. In another particular embodiment, said SUMO ortholog is from *Homo sapiens* having the amino acid sequence shown in SEQ ID NO: 5 (hsSUMO2), in particular wherein SEQ ID NO: 5 comprises the substitution D63K, optionally in combination with D71R or D71W, and/or R56K or R56S. In a preferred embodiment said SUMO ortholog is from *Homo sapiens* having the amino acid sequence shown in SEQ ID NO: 5 (hsSUMO2) comprising the combination of (i) R56K, D63K, D71R, or (ii) R56S, D63K, and D71W.

Likewise, the present disclosure also provides a cognate variant protease to the variant protease cleavage site of the present disclosure. The variant protease of the present disclosure is capable of cleaving the protease cleavage site as disclosed herein. More specifically, it cleaves a protease cleavage site (PCS) having the amino acid sequence of SEQ ID NO: 41 (Mut1 bdSUMO), when fused to the N-terminus of MBP having the amino acid sequence of SEQ ID NO: 71, more efficiently after the C-terminal Gly-Gly than a protease cleavage site having the amino acid sequence of SEQ ID NO: 4 (scSUMO) fused to the N-terminus of SEQ ID NO: 71 or a protease cleavage site having the amino acid sequence of SEQ ID NO: 3 (hsSUMO) fused to the N-terminus of SEQ ID NO: 71, when tested at the same concentration under standard conditions of 1 hour incubation at 21° C., an initial concentration of PCS-MBP fusions of 100 μM in a buffer consisting of 45 mM Tris/HCl PH 7.5, 250 mM NaCl, 2 mM $MgCl_2$, 250 mM sucrose, 10 mM DTT. Efficiency of the cleavage can be read out using routine procedures, for example HPLC and 'under the curve integration', or SDS-PAGE followed by Coomassie staining and measuring the gel with a densitometer. In a preferred embodiment, said variant protease cleaves an at least a 500-fold molar excess of the Mut1 bdSUMO-MBP fusion at the above standard conditions. In a more preferred embodiment, said variant protease cleaves an at least a 1000-fold molar excess of the Mut1 bdSUMO-MBP fusion at the above standard conditions.

In embodiments, said variant protease has at least 80% sequence identity over the full-length of SEQ ID NO: 6 (bdSENP1), and said variant protease comprises a substitution at the amino acid position corresponding to position 33 of SEQ ID NO: 6, wherein the amino acid at said position is substituted by another amino acid selected from the group consisting of S, H, Q, A, G, and C; preferably wherein said another amino acid is selected from the group consisting of S, H, Q, and A. In embodiments, the variant protease has at least 82%, preferably at least 84%, more preferably at least 86%, more preferably at least 88%, more preferably at least 90%, more preferably at least 92%, more preferably at least 94%, more preferably at least 96%, more preferably at least 98%, more preferably at least 99% sequence identity over the full length of SEQ ID NO: 6 (bdSENP1). SEQ ID NO: 6 shows the catalytic domain of bdSENP1.

In certain embodiments, said variant protease further comprises a substitution at the amino acid position corresponding to position 99 of SEQ ID NO: 6 (R346 of SEQ ID NO: 73), wherein the amino acid at said position is substituted by another amino acid selected from the group consisting of E, S, V, Y, and L; preferably wherein said amino acid is selected from the group consisting of E, S, and V. In addition to the substitution at the amino acid position corresponding to position 99 of SEQ ID NO: 6 (R346 of SEQ ID NO: 73), or in alternative, said variant protease may further comprise a substitution at the amino acid position corresponding to position 22 of SEQ ID NO: 6 (R269 of SEQ ID NO: 73), wherein the amino acid at said position is substituted by another amino acid selected from the group consisting of E, S, P, K, V. Moreover, said variant protease may further comprise a substitution at the amino acid position corresponding to position 103 of SEQ ID NO: 6 (K350 of SEQ ID NO: 73), wherein the amino acid at said position is substituted by another amino acid selected from the group consisting of M, E, V, G, T, and R; preferably wherein said amino acid is selected from the group consisting of M, E, V, G, and T.

In a preferred embodiment, said variant protease comprises a combination of substitutions selected from the group consisting of (i) 280S, 346E (MutB); (ii) 280H, 269S, 350V (MutG); (iii) 269P, 280A, 346E, 350M (MutH); (iv) 269K, 280H, 346E, 350E (MutI); (v) 269E, 280S, 346S, 350T (MutJ); and (vi) 269V, 280Q, 346V, 350G (MutK), wherein said amino acid substitutions are at positions corresponding to amino acid residues R269, N280, R346 and K350 of wild-type bdSENP1 set forth in SEQ ID NO: 73.

In a most preferred embodiment, the variant protease has the amino acid sequence of SEQ ID NO: 6 (bdSENP1), except for the substitution at the amino acid position corresponding to N280 of SEQ ID NO: 73, optionally, if present, in combination with the additional substitutions at the amino acid positions corresponding to R269, R346, and/or K350 of SEQ ID NO: 73. In preferred embodiments, said substitution at the amino acid position corresponding to N280 of SEQ ID NO: 73 is selected from the group consisting of N280S, N280H, N280Q, N280A, N280G, and N280C; preferably wherein said substitution is selected from the group consisting of N280S, N280H, N280Q, and N280A. In further embodiments, the additional substitution at the amino acid position corresponding to R269 of SEQ ID NO: 73 is selected from the group consisting of R269E, R269S, R269P, R269K, R269V. In further embodiments, the additional substitution at the amino acid position corresponding to R346 of SEQ ID NO: 73 is selected from the group consisting of R346E, R346S, and R346V. In further embodiments, the additional substitution at the amino acid position corresponding to K350 of SEQ ID NO: 73 is selected from the group consisting of K350M, K350E, K350V, K350G, K350T, and K350R; preferably wherein said substitution is selected from the group consisting of K350M, K350E, K350V, K350G, and K350T. In particular embodiments, said variant protease comprises a combination of substitutions selected from the group consisting of (i) N280S, R346E (MutB); (ii) N280H, R269S, K350V (MutG); (iii) R269P, N280A, R346E, K350M (MutH); (iv) R269K, N280H, R346E, K350E (MutI); (v) R269E, N280S, R346S, K350T (MutJ); and (vi) R269V, N280Q, R346V, K350G (MutK); wherein said amino acid substitutions are at positions corresponding to amino acid residues R269, N280, R346 and K350 of wild-type bdSENP1 set forth in SEQ ID NO: 73. In specific embodiments, the variant protease has an amino acid sequence selected from SEQ ID NO: 56-70.

Further provided is a fusion protein, comprising a variant protease cleavage site according to the present disclosure. For example, such fusion protein may comprise a protein of interest, to which an affinity tag is fused to said protein together with the variant protease cleavage site of the present disclosure.

In this context, the present disclosure also provides a process of purifying a protein of interest, comprising the steps of (i) providing a protein of interest to be purified wherein said protein comprises an affinity tag fused to said protein together with a variant protease cleavage site according to the present disclosure;
(ii) binding the protein of step (i) to an affinity matrix via said affinity tag; and
(iii) eluting the protein from the affinity matrix using a (cognate) variant protease of the present disclosure;

thereby purifying the protein. Suitable affinity tags and corresponding affinity matrices are known to the skilled person, and the affinity purification process can be carried out using routine procedures only.

The invention is further described by the following embodiments:

1. A fusion protein, comprising the structure

N-PCS$^Y$-degSig$_N$-M-PCS$^X$-degSig$_C$-C;

wherein
   N represents the N-terminus;
   PCS$^Y$ and PCS$^X$ each represent a protease cleavage site (PCS), which differ from each other in at least one amino acid residue such that the first amino acid of degSig$_N$ becomes the new N-terminus of the remaining fusion;
   degSig$_N$ represents a degradation signal, which promotes degradation of the fusion protein in a host cell if PCS$^Y$ is cleaved by a protease;
   M represents a cytoplasmic selection marker; and
   degSig$_C$ represents a second degradation signal, which promotes degradation of the fusion protein in a host cell if PCS$^X$ is not cleaved by a protease; and
   C represents the C-terminus.

2. The fusion protein of embodiment 1, wherein PCS$^Y$ and/or PCS$^X$ are protease cleavage sites selected from bdSUMO shown in SEQ ID NO: 3, a paralog or an ortholog of bdSUMO, or a functionally equivalent variant thereof having at least 80% sequence identity over the full-length of SEQ ID NO: 3 (bdSUMO); optionally wherein PCS$^Y$ and/or PCS$^X$ are selected from a paralog or an ortholog of bdSUMO, or a functionally equivalent variant of bdSUMO having at least 80% sequence identity over the full-length of SEQ ID NO: 3 (bdSUMO).

3. The fusion protein of any preceding embodiment, wherein PCS$^Y$ and PCS$^X$ differ from each other in at least one amino acid residue, which are in the PCS interface interacting with the cognate protease of PCS$^X$;
   preferably in at least two amino acid residues, which are in the PCS interface interacting with the cognate protease of PCS$^X$;
   more preferably in at least three amino acid residues, which are in the PCS interface interacting with the cognate protease of PCS$^X$.

4. The fusion protein of any preceding embodiment, wherein degSig$_N$ comprises the amino acid sequence FLFVQ (Degron$^{NER}$; SEQ ID NO: 1).

5. The fusion protein of any preceding embodiment, wherein M is a cytoplasmic selection marker providing resistance against an antibiotic selection agent, preferably wherein M provides resistance against hygromycin B.

6. The fusion protein of any preceding embodiment, wherein degSig$_C$ comprises the amino acid sequence AADENYALAA (ssrA; SEQ ID NO: 2).

7. A nucleic acid construct, comprising a nucleic acid sequence coding for the fusion protein of any one of the preceding embodiments.

8. The nucleic acid construct of embodiment 7, wherein the nucleic acid construct is an expression construct, wherein the nucleic acid sequence coding for the fusion protein is under the control of a constitutive promoter.
9. A nucleic acid expression construct library, comprising a plurality of diversified nucleic acid expression constructs according to embodiment 7,
   wherein the nucleic acid encoding $PCS^Y$ of the fusion protein comprises a diversity such that in the encoded $PCS^Y$ at least one encoded amino acid position, preferably at least two encoded amino acid positions, more preferably at least three encoded amino acid positions are diversified.
10. The nucleic acid expression construct library of embodiment 9, wherein the amino acid position(s) comprising the diversity is/are position(s) within the $PCS^Y$ interface interacting with a protease of interest capable of cleaving the unmodified, non-diversified $PCS^Y$.
11. A plurality of host cells, wherein each member of the plurality of host cells comprises a nucleic acid expression construct according to embodiment 7, which is not diversified, or a member of a plurality of nucleic acid expression constructs according to embodiment 9 or 10; preferably wherein the host cell is an *E. coli* host cell, wherein the host cells promote degradation of the fusion protein via $degSig_N$, if $PCS^Y$ is cleaved by a protease, and promote degradation of the fusion protein via $degSig_C$, if $PCS^X$ is not cleaved by a protease.
12. The plurality of host cells of embodiment 11, wherein the host cells are capable of simultaneously expressing a protease of interest and the fusion protein encoded by the nucleic acid expression construct, wherein said protease of interest is capable of cleaving $PCS^X$;
    preferably wherein the protease is under the control of an inducible promoter.
13. The plurality of host cells of embodiment 11, wherein the host cells comprise a first non-diversified nucleic acid expression construct according to embodiment 7, and a plurality of second expression constructs encoding a diversified protease of interest,
    wherein the host cells are capable of simultaneously expressing said diversified protease of interest together with the fusion protein encoded by said first expression construct,
    wherein said plurality of second expression constructs is derived from a protease capable of cleaving $PCS^Y$ of the fusion protein of the first expression construct, and
    wherein said plurality of second expression constructs comprises a diversity in at least one amino acid position at the protease interface interacting with said $PCS^Y$,
    preferably in at least two amino acid positions at the protease interface interacting with said $PCS^Y$,
    more preferably in at least three amino acid positions at the protease interface interacting with said $PCS^Y$,
    more preferably in at least four amino acid positions at the protease interface interacting with said $PCS^Y$,
    and most preferably in at least five amino acid positions at the protease interface interacting with said $PCS^Y$.
14. A method for simultaneously testing whether (a) a first protease cleavage site $PCS^Y$ is not cleaved by a protease of interest, and (b) whether a second protease cleavage site $PCS^X$ is cleaved by said protease of interest, comprising the steps of
    (i) providing a host cell comprising a first nucleic acid construct according to embodiment 7 and a second expression construct for expression of a protease of interest, wherein the host cell is capable of simultaneously expressing the fusion protein and said protease of interest, and wherein the host cells promote degradation of the fusion protein via $degSig_N$, if $PCS^Y$ is cleaved by a protease, and promote degradation of the fusion protein via $degSig_C$, if $PCS^X$ is not cleaved by a protease;
    (ii) cultivating the host cell of step (i) under conditions such that the fusion protein and the protease of interest are simultaneously expressed; and
    (iii) subjecting the host cell of step (ii) to selective conditions using the cognate selecting agent for the selection marker of the fusion protein encoded by the first nucleic acid construct;
    wherein growth of the host cell in the presence of the selective conditions applied in step (iii) indicates that the first protease cleavage site $PCS^Y$ is not cleaved by said protease of interest, and that said second protease cleavage site $PCS^X$ is cleaved by said protease of interest of said second nucleic acid expression construct;
    preferably wherein the selection marker confers antibiotic resistance to the host cell.
15. A method for identifying a protease cleavage site variant $PCS^Y$ of a first protease cleavage site $PCS^X$, wherein $PCS^Y$ is not cleaved by a protease of interest, comprising the steps of
    (i) providing a plurality of host cells, wherein each member of said plurality of host cells comprises a member of a plurality of first nucleic acid constructs according to embodiment 10, wherein the plurality of first nucleic acid constructs encodes diversified variant $PCS^Y$ of a first protease cleavage site $PCS^X$, and a second expression construct for expression of a protease of interest, wherein said protease of interest is capable of cleaving $PCS^X$, whereby the plurality of host cells is capable of simultaneously expressing the fusion protein encoded by the first nucleic acid construct and said protease of interest, and wherein the host cells promote degradation of the fusion protein via $degSig_N$, if $PCS^Y$ is cleaved by a protease, and promote degradation of the fusion protein via $degSig_C$, if $PCS^X$ is not cleaved by a protease;
    (ii) cultivating the plurality of host cells of step (i) under conditions such that the fusion protein and the protease of interest are simultaneously expressed; and
    (iii) subjecting the plurality of host cells of step (ii) to selective conditions using the cognate selecting agent for the selection marker of the fusion protein encoded by the plurality of first nucleic acid constructs;
    (iv) identifying a host cell, which has been positively selected in step (iii), and identifying the sequence of $PCS^Y$ of the first nucleic acid construct of the identified host cell, wherein $PCS^Y$ is a protease cleavage site variant of a first protease cleavage site $PCS^X$, and wherein $PCS^Y$ is not cleaved by said protease of interest of the second expression construct.
16. A method for identifying a protease variant, which is capable of cleaving a protease cleavage site variant $PCS^X$ of a first protease cleavage site $PCS^Y$, but not the first protease cleavage site $PCS^Y$, wherein said protease variant is derived from a first protease, which is capable of cleaving the first protease cleavage site $PCS^Y$, but not the protease cleavage site variant $PCS^X$, comprising the steps of
(i) providing a plurality of host cells, wherein each member comprises a non-diversified first nucleic acid expression construct according to embodiment 7, in which $PCS^X$ is a protease cleavage site variant of a first protease cleavage site $PCS^Y$, wherein the $PCS^Y$ is cleaved by a first protease of interest and $PCS^X$ is not cleaved by said parent protease; and wherein each member of said plurality of host cells further comprises a member of a plurality of a second expression construct expressing protease variants of said first protease, wherein said plurality of second nucleic acid expression constructs comprises a diversity in at least one amino acid position at the protease interface interacting with said first $PCS^Y$, whereby the plurality of host cells is capable of simultaneously expressing the fusion protein and said protease of interest, and wherein the host cells promote degradation of the fusion protein via $degSig_N$, if $PCS^Y$ is cleaved by a protease, and promote degradation of the fusion protein via $degSig_C$, if $PCS^X$ is not cleaved by a protease;

(ii) cultivating the plurality of host cells of step (i) under conditions such that the fusion protein and the protease of interest are simultaneously expressed; and (iii) subjecting the plurality of host cells of step (ii) to selective conditions using the cognate selecting agent for the selection marker of the fusion protein encoded by the first nucleic acid expression construct;

(iv) identifying a host cell, which has been positively selected in step (iii), and identifying the sequence of the protease variant encoded by the second nucleic acid construct of the identified host cell, wherein said protease variant is capable of cleaving a protease cleavage site variant $PCS^X$ of a first protease cleavage site $PCS^Y$, but incapable of cleaving the first protease cleavage site $PCS^Y$.

17. A method of preparing an orthogonal protease (P)/protease cleavage site (PCS) system, comprising the steps of (i) providing a plurality of host cells, wherein each member of said plurality of host cells comprises a member of a plurality of first nucleic acid constructs according to embodiment 10, which encodes a diversified variant $PCS^Y$ of a first protease cleavage site $PCS^X$, and a second expression construct for expression of a first protease $P^X$ of interest, which is capable of cleaving $PCS^X$, whereby the plurality of host cells is capable of simultaneously expressing the fusion protein and said first protease of interest, and wherein the host cells promote degradation of the fusion protein via $degSig_N$, if $PCS^Y$ is cleaved by a protease, and promote degradation of the fusion protein via $degSig_C$, if $PCS^X$ is not cleaved by a protease;

(ii) cultivating the plurality of host cells of step (i) under conditions such that the fusion protein and the first protease $P^X$ are simultaneously expressed; and (iii) subjecting the plurality of host cells of step (ii) to selective conditions using the cognate selecting agent for the selection marker of the fusion protein encoded by the plurality of first nucleic acid constructs;

(iv) identifying a host cell which has been positively selected in step (iii), and identifying $PCS^\#$, wherein $PCS^\#$ is the sequence of the $PCS^Y$ of the first nucleic acid construct of the identified host cell, wherein $PCS^\#$ is a protease cleavage site variant from a first protease cleavage site $PCS^X$, and wherein $PCS^\#$ is not cleaved by said first protease $P^X$ while $PCS^X$ is cleaved by $P^X$;

(v) preparing a second plurality of host cells, which comprises a third nucleic acid expression construct, encoding a non-diversified fusion protein comprising the structure:

$$N\text{-}PCS^*\text{-}degSig_N\text{-}M\text{-}PCS^\#\text{-}degSig_C\text{-}C;$$

wherein N represents the N-terminus, $PCS^\#$ is the sequence of $PCS^Y$ identified in step (iv), PCS* is a second protease cleavage site, which may or may not be identical to $PCS^X$, and which differs from $PCS^\#$ in at least one amino acid residue, $degSig_N$ represents a degradation signal, which promotes degradation of the fusion protein in the host cell if PCS* is cleaved by a protease protease such that the first amino acid of $degSig_N$ becomes the new N-terminus of the remaining fusion, M represents a cytoplasmic selection marker, and $degSig_C$ represents a second degradation signal, which promotes degradation of the fusion protein in a host cell if $PCS^\#$ is not cleaved by a protease, and C represents the C-terminus;

and wherein each member of said second plurality of host cells further comprises a member of a plurality of a fourth expression construct expressing protease variants of a protease P*, wherein said protease P* is capable of cleaving PCS* such that the first amino acid of $degSig_N$ becomes the new N-terminus of the remaining fusion, wherein said plurality of the fourth nucleic acid expression constructs comprises a diversity in at least one amino acid position at the protease interface of said protease P* interacting with said first protease cleavage site PCS*, whereby the plurality of host cells is capable of simultaneously expressing the non-diversified fusion protein and said protease variants, and wherein the host cells promote degradation of the fusion protein via $degSig_N$, if PCS* is cleaved by a protease; and promote degradation of the fusion protein via $degSig_C$, if $PCS^\#$ is not cleaved by a protease;

(vi) cultivating the plurality of host cells of step (v) under conditions such that the fusion protein and the variants of protease P* are simultaneously expressed;

(vii) subjecting the plurality of host cells of step (vi) to selective conditions using the cognate selecting agent for the selection marker of the fusion protein encoded by the third nucleic acid expression construct; and (viii) identifying a cell, which has been positively selected in step (vii), and identifying $P^\#$, wherein $P^\#$ is the sequence of the protease variant $P^X$ encoded by the fourth nucleic acid construct of the identified host cell, which protease variant $P^\#$ is capable of cleaving the protease cleavage site variant $PCS^\#$, and which is incapable of cleaving the first cleavage site $PCS^X$;

thereby obtaining orthogonal protease/protease cleavage site systems of a PCS* and a protease P*, and a variant PCS# and a variant protease P#.

18. A variant SUMO protease cleavage site (PCS), wherein said variant SUMO PCS comprises a C-terminal Gly-Gly, and, when fused to the N-terminus of MBP having the amino acid sequence of SEQ ID NO: 71, is cleaved more efficiently after the C-terminal Gly-Gly by a protease having the amino acid sequence of SEQ ID NO: 57 (MutB bdSENP1) as compared to cleavage by a protease having the amino acid sequence of SEQ ID NO: 7 (scUlp1) or SEQ ID NO: 8 (hsSENP2), when tested at the same concentration under standard conditions of 1 hour incubation at 21° C., an initial concentration of PCS-MBP fusion of 100 µM in a buffer consisting of 45 mM Tris/HCl PH 7.5, 250 mM NaCl, 2 mM MgCl$_2$, 250 mM sucrose, 10 mM DTT;
   optionally wherein the protease having the amino acid sequence of SEQ ID NO: 57 (MutB bdSENP1) cleaves an at least a 500-fold molar excess of the said SUMO PCS-MBP fusion at the above standard conditions.

19. The variant protease cleavage site of embodiment 18, wherein the variant protease cleavage site has at least 80% sequence identity over the full-length of SEQ ID NO: 3 (bdSUMO), or is a homolog of the bdSUMO protease cleavage site shown in SEQ ID NO: 3, wherein said variant protease cleavage site, when aligned to the full-length sequence of SEQ ID NO: 3, comprises a substitution at the position corresponding to D67 of the aligned SEQ ID NO: 3, wherein the amino acid at said position is substituted by another amino acid selected from the group consisting of K, R, N, A and H; preferably wherein said amino acid is selected from the group consisting of K and R; in particular wherein said amino acid is K.

20. The variant protease cleavage site of embodiment 19, wherein said variant protease cleavage site, when aligned to the full-length sequence of SEQ ID NO: 3, further comprises a substitution at the position corresponding to Q75 of the aligned SEQ ID NO: 3, wherein the amino acid at said position is substituted by another amino acid selected from the group consisting of R, W, A, H, M, I, P, and F; preferably wherein said amino acid is selected from the group consisting of R, W, A, and H; and/or
   wherein said variant protease cleavage site, when aligned to the full-length sequence of SEQ ID NO: 3, further comprises a substitution at the position corresponding to T60 of the aligned SEQ ID NO: 3, wherein the amino acid at said position is substituted by another amino acid selected from the group consisting of S, N, K, P, H, R, and Q; preferably wherein said amino acid is selected from the group consisting of S, N, K, and P.

21. The variant protease cleavage site of any one of embodiments 19 to 20, wherein said variant protease cleavage site comprises a combination of substitutions selected from the group consisting of
   (i) 67K, 60K, 75R (Mut1);
   (ii) 67K, 60P, 75W (Mut8);
   (iii) 67K, 75R (Mut10);
   (iv) 67K, 60S, 75H (Mut11);
   (v) 67K, 60S, 75W (Mut12);
   (vi) 67K, 60S, 75A (Mut13);
   (vii) 67K, 60N, 75W (Mut14); and
   (viii) 67K, 60N, 75A (Mut15).

22. The variant protease cleavage site of any one of embodiments 19-21, having the amino acid sequence of SEQ ID NO: 3 (bdSUMO), except for the substitution D67K, optionally, if present, in combination with the additional substitutions at position T60 and/or Q75; preferably wherein the variant protease cleavage site has the amino acid sequence of any one of SEQ ID NO: 41 to SEQ ID NO: 55.

23. A variant protease, wherein said variant protease cleaves a protease cleavage site (PCS) having the amino acid sequence of SEQ ID NO: 41 (Mut1 bdSUMO), when fused to the N-terminus of MBP having the amino acid sequence of SEQ ID NO: 71, more efficiently after the C-terminal Gly-Gly than a protease cleavage site having the amino acid sequence of SEQ ID NO: 4 (scSUMO) fused to the N-terminus of SEQ ID NO: 71 or a protease cleavage site having the amino acid sequence of SEQ ID NO: 3 (hsSUMO) fused to the N-terminus of SEQ ID NO: 71, when tested at the same concentration under standard conditions of 1 hour incubation at 21° C., an initial concentration of PCS-MBP fusions of 100 µM in a buffer consisting of 45 mM Tris/HCl PH 7.5, 250 mM NaCl, 2 mM MgCl$_2$, 250 mM sucrose, 10 mM DTT;
   optionally wherein said variant protease cleaves an at least a 500-fold molar excess of the Mut1 bdSUMO-MBP fusion at the above standard conditions.

24. The variant protease of embodiment 23, wherein said variant protease has at least 80% sequence identity over the full-length of SEQ ID NO: 6 (bdSENP1), wherein said variant protease comprises a substitution at the amino acid position corresponding to position 33 of SEQ ID NO: 6 (N280 of SEQ ID NO: 73), wherein the amino acid at said position is substituted by another amino acid selected from the group consisting of S, H, Q, A, G, and C; preferably wherein said amino acid is selected from the group consisting of S, H, Q, and A.

25. The variant protease of embodiment 24, wherein said variant protease further comprises a substitution at the amino acid position corresponding to position 99 of SEQ ID NO: 6 (R346 of SEQ ID NO: 73), wherein the amino acid at said position is substituted by another amino acid selected from the group consisting of E, S, V, Y, and L; preferably wherein said substitution is selected from the group consisting of E, S, and V; and/or
   wherein said variant protease further comprises a substitution at the amino acid position corresponding to position 22 of SEQ ID NO: 6 (R269 of SEQ ID NO: 73), wherein the amino acid at said position is substituted by another amino acid selected from the group consisting of E, S, P, K, V; and/or
   wherein said variant protease further comprises a substitution at the amino acid position corresponding to position 103 of SEQ ID NO: 6 (K350 of SEQ ID NO: 73), wherein the amino acid at said position is substituted by another amino acid selected from the group consisting of M, E, V, G, T, and R; preferably wherein said substitution is selected from the group consisting of M, E, V, G, and T.

26. The variant protease of any one of embodiments 24 to 25, wherein said variant protease comprises a combination of substitutions selected from the group consisting of
   (i) 280S, 346E (MutB);
   (ii) 280H, 269S, K350V (MutG);
   (iii) 269P, 280A, 346E, 350M (MutH);

(iv) 269K, 280H, 346E, 350E (MutI);
(v) 269E, 280S, 346S, 350T (MutJ); and
(vi) 269V, 280Q, 346V, 350G (MutK),
wherein said amino acid substitutions are at positions corresponding to amino acid residues R269, N280, R346 and K350 of wild-type bdSENP1 set forth in SEQ ID NO: 73.

27. The variant protease of any one of embodiments 24-26, having the amino acid sequence of SEQ ID NO: 6 (bdSENP1), except for the substitution at the amino acid position corresponding to N280 of SEQ ID NO: 73, optionally, if present, in combination with the additional substitutions at amino acid positions corresponding to R269, R346, and/or K350 of SEQ ID NO: 73; preferably wherein the variant protease has the amino acid sequence of any one of SEQ ID NO: 56 to SEQ ID NO: 70.

28. The variant protease of any one of embodiments 23-27, wherein said protease is capable of cleaving the protease cleavage site according to embodiments 18-22.

29. A fusion protein, comprising a variant protease cleavage site according to embodiments 18-22.

30. A process of purifying a protein of interest, comprising the steps of
   (i) providing a protein of interest to be purified wherein said protein comprises an affinity tag fused to said protein together with a variant protease cleavage site according to any one of embodiments 18-22;
   (ii) binding the protein of step (i) to an affinity matrix via said affinity tag; and
   (iii) eluting the protein from the affinity matrix using a variant protease of any one of embodiments 23-27; thereby purifying the protein.

The present invention is further illustrated by the following figures, sequences and examples, which are in no way intended to limit the scope of the invention, which is only determined by the appended claims.

DESCRIPTION OF THE FIGURES

FIG. 3 (A) Illustration of the fusion proteins used to select for bdSUMO mutants ($bdSUMO^{MutX}$), which are not cleaved by the SUMOstar protease. (B) Sequence alignment of amino acids 56-79 of wild-type bdSUMO ($bdSUMO^{wt}$) and ten different bdSUMO mutants (SEQ ID NOs: 9-19). Identical residues are highlighted in black boxes and the numbering of the sequence is according to the full-length wild type (wt) bdSUMO protein. The bdSUMO mutant that belongs to the SUMOvera system is underlined ($bdSUMO^{Mut1}$).

Figure 1:
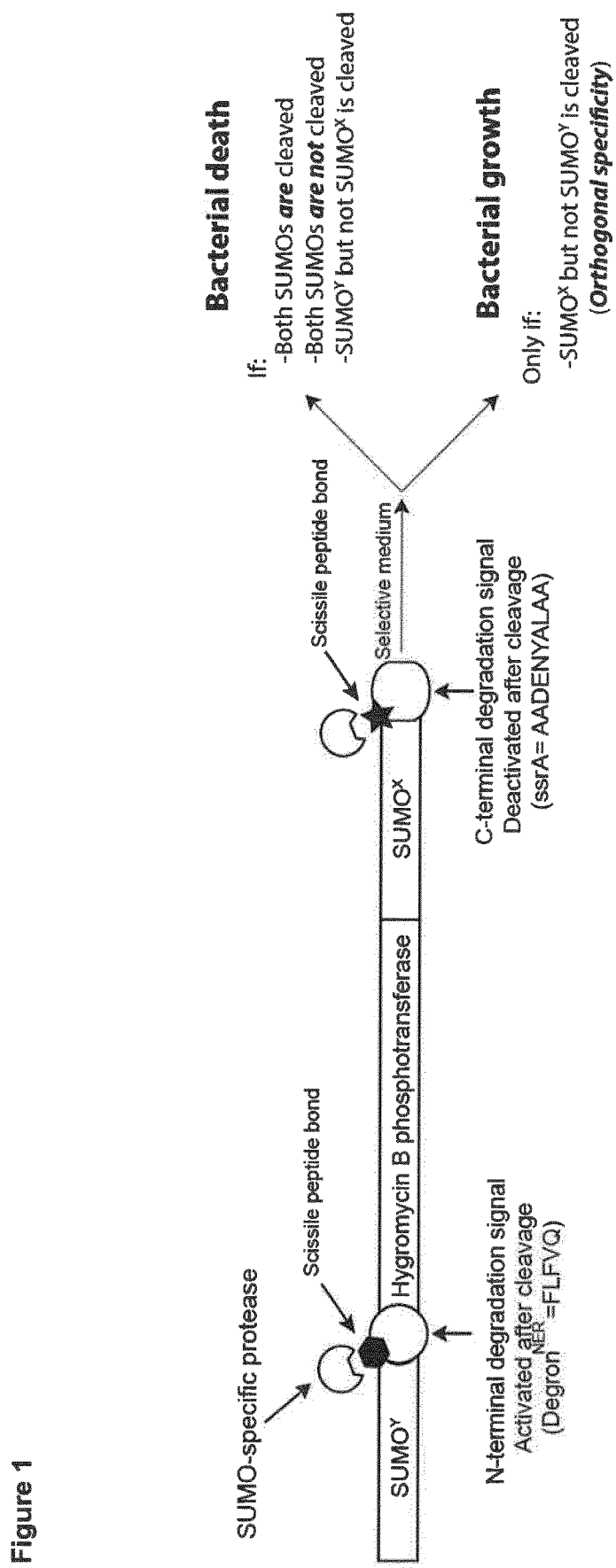
FIG. 1 Diagram of the in vivo system for the selection of proteases and protease-cleavage sites with orthogonal specificities. The system is based on the survival of $E.\ coli$ cells in selective medium containing hygromycin B. Cells co-express a SUMO-specific protease and the fusion protein $SUMO^Y$-$Degron^{NER}$-HygB-$SUMO^X$-ssrA as a selection marker. Cells survive only if a given SUMO-specific protease shows orthogonal specificity to two different protease cleavage sites ($SUMO^Y$ and $SUMO^X$).
Figure 2:
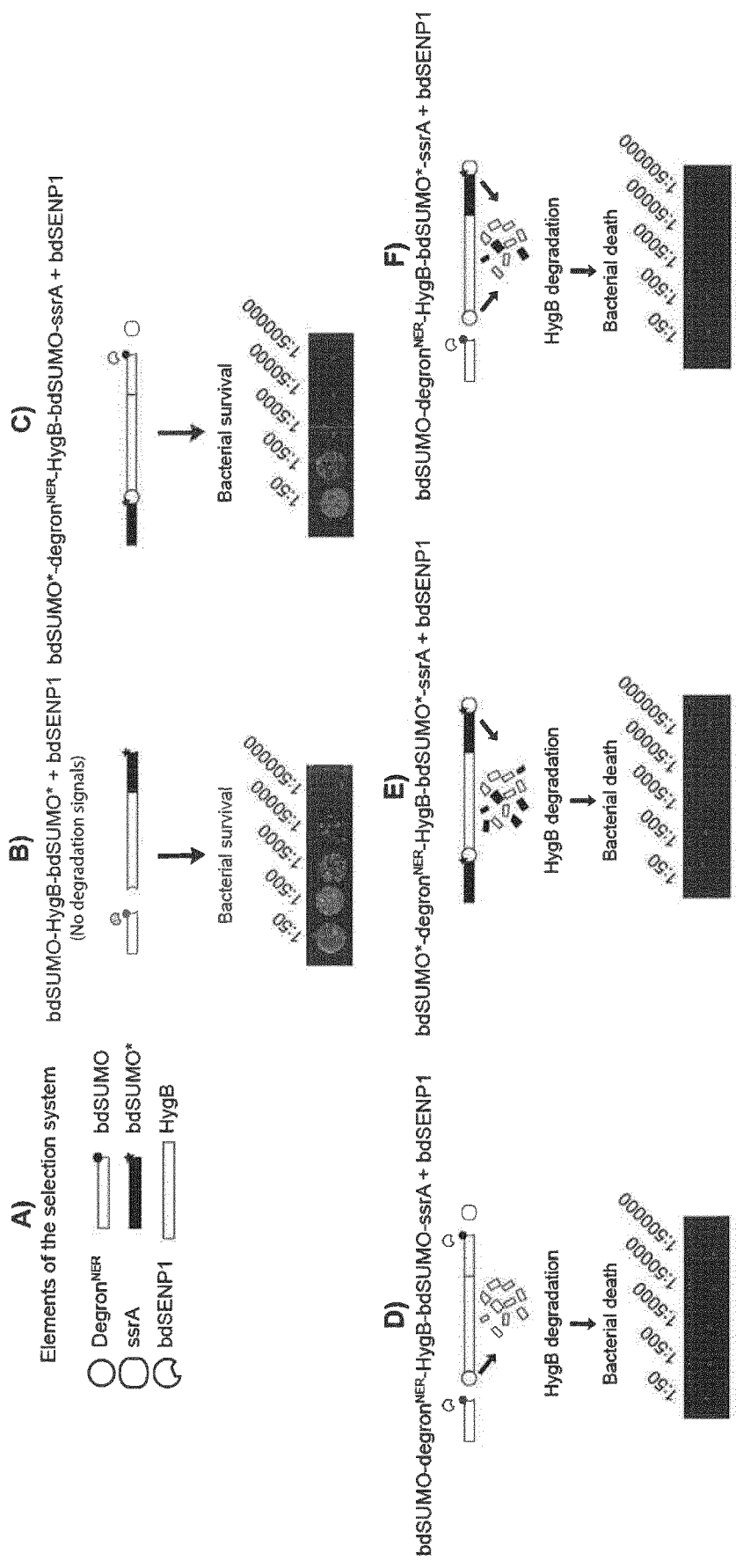
FIG. 2 Validation of the in vivo selection system. (A) The SUMO protein (bdSUMO) and the SUMO-specific protease 1 (bdSENP1) from $B.\ distachyon$ were used as model proteins to the test the functionality of the selection system. A non-cleavable SUMO mutant (SUMO*) was used to account against cleavage. (B) Cells expressing a HygB construct lacking both protein degradation signals were used as positive control for cellular growth in selective media. (C) Only cells expressing SUMO*-$Degron^{NER}$-HygB-bdSUMO-ssrA survived due to the permanent inactivation of both degradation signals. (D, E, C and F). Bacteria co-expressing bdSENP1 and a different reporter protein do not survive after the degradation of HygB due to activation of the $Degron^{NER}$ and/or the lack of inactivation of the ssrA signal.
Figure 4:
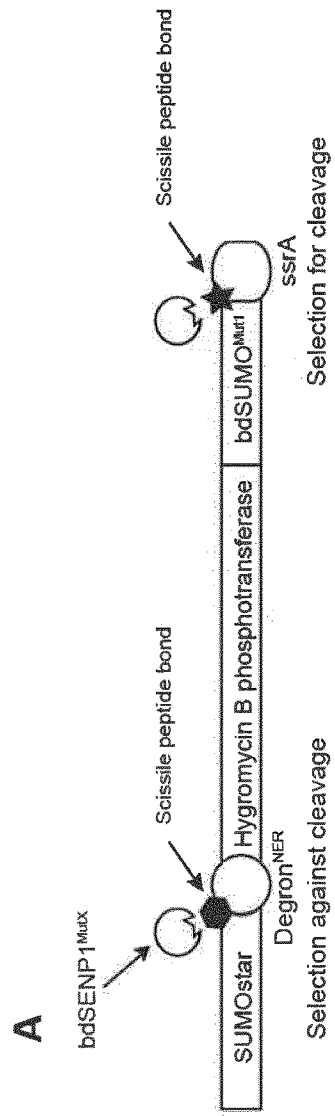
FIG. 4 (A) Reporter construct used to select for bdSENP1 mutants ($bdSENP1^{MutX}$) that cleave $bdSUMO^{Mut1}$ but do not recognize SUMOstar as substrate. (B) Sequence alignment of amino acids 254-354 of wild type bdSENP1 and six different functional bdSENP1 mutants (SEQ ID NO: 25-31). The bdSENP1 mutant that belongs to the SUMOvera system is shown underlined ($bdSENP1^{MutB}$). The numbering of the sequencing is set according to the full-length bdSENP1 protein (set forth in SEQ ID NO: 73) and identical residues are highlighted in black.
Figure 5:
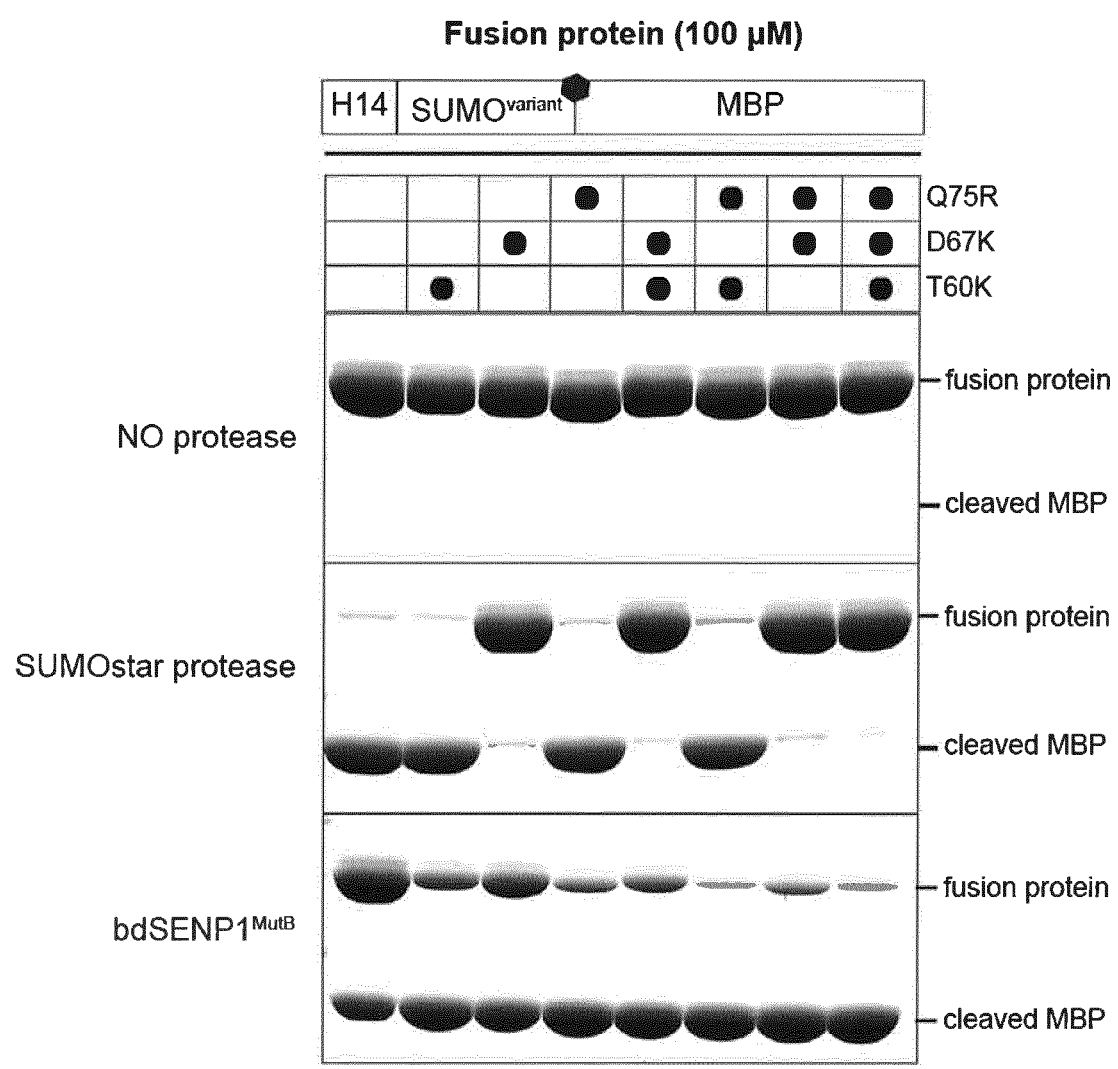
FIG. 5 Effect of each mutation in $bdSUMO^{Mut1}$ for the cleavage resistance against SUMOstar protease. Different variants of the bdSUMO-MBP fusion protein containing one, two or three mutations as in $bdSUMO^{Mut1}$ were incubated with a large amount of SUMOstar protease (10 μM) for 2 h at 25° C. Samples were resolved by SDS-PAGE to separate the fusion protein from the C-terminal cleaved MBP. The same bdSUMO-MBP fusion proteins were used to evaluate the contribution of each mutation in $bdSUMO^{Mut1}$ for the recognition by $bdSENP1^{MutB}$. Samples containing 100 μM of each MBP fusion protein were incubated with 200 nM of $bdSENP1^{MutB}$ protease for 1 h at 4° C.

SEQUENCES (Degron$^{NER}$)
SEQ ID NO: 1
FLFVQ (ssrA)
SEQ ID NO: 2
AADENYALAA (WT bdSUMO amino acids 1-97)
SEQ ID NO: 3
MSAAGGEEDKKPAGGEGGGAHINLKVKGQDGNEVFFRIKRSTQLKKLMN
AYCDRQSVDMTAIAFLFDGRRLRAEQTPDELEMEDGDEIDAMLHQTGG (WT scSUMO amino acids 1-98)
SEQ ID NO: 4
MSDSEVNQEAKPEVKPEVKPETHINLKVSDGSSEIFFKIKKTTPLRRLM
EAFAKRQGKEMDSLRFLYDGIRIQADQTPEDLDMEDNDIIEAHREQIGG (WT hsSUMO2; Homo sapiens SUMO2, amino acids 1-93)
SEQ ID NO: 5
MADEKPKEGVKTENNDHINLKVAGQDGSVVQFKIKRHTPLSKLMKAYCE
RQGLSMRQIRFRFDGQPINETDTPAQLEMEDEDTIDVFQQQTGG (WT bdSENP1 amino acids 248-481)
SEQ ID NO: 6
PFVPLTDEDEDNVRHALGGRKRSETLSVHEASNIVITREILQCLNDKEW
LNDEVINLYLELLKERELREPNKFLKCHFFNTFFYKKLINGGYDYKSVR
RWTTKRKLGYNLIDCDKIFVPIHKDVHWCLAVINIKEKKFQYLDSLGYM
DMKALRILAKYLVDEVKDKSGKQIDVHAWKQEGVQNLPLQENGWDCGMF
MLKYIDFYSRDMELVFGQKHMSYFRRRTAKEILDLKAG (scUlp1 amino acids 403-621)
SEQ ID NO: 7
LVPELNEKDDDQVQKALASRENTQLMNRDNIEITVRDFKTLAPRRWLND
TIIEFFMKYIEKSTPNTVAFNSFFYTNLSERGYQGVRRWMKRKKTQIDK
LDKIFTPINLNQSHWALGIIDLKKKTIGYVDSLSNGPNAMSFAILTDLQ
KYVMEESKHTIGEDFDLIHLDCPQQPNGYDCGIYVCMNTLYGSADAPLD
FDYKDAIRMRRFIAHLILTDALK (hsSENP2; Homo sapiens SENP2, amino acids 419-644)
SEQ ID NO: 8
EFPEITEEMEKEIKNVFRNGNQDEVLSEAFRLTITRKDIQTLNHLNWLN
DEIINFYMNMLMERSKEKGLPSVHAFNTFFFTKLKTAGYQAVKRWTKKV
DVFSVDILLVPIHLGVHWCLAVVDFRKKNITYYDSMGGINNEACRILLQ
YLKQESIDKKRKEFDTNGWOLFSKKSQEIPQQMNGSDCGMFACKYADCI
TKDRPINFTQQHMPYFRKRMVWEILHRKLL (Wt bdSUMO; amino acids 56-79)
SEQ ID NO: 9
SVDMTAIAFLFDGRRLRAEQTPDE (Mut1 bdSUMO; amino acids 56-79)
SEQ ID NO: 10
SVDMKAIAFLFKGRRLRAERTPDE -continued (Mut2 bdSUMO; amino acids 56-79)
SEQ ID NO: 11
SVDMTAIAFLFKGRRLRAECTPDE (Mut3 bdSUMO; amino acids 56-79)
SEQ ID NO: 12
SVDMHAIAFLFKGRRLRAEKTPDE (Mut4 bdSUMO; amino acids 56-79)
SEQ ID NO: 13
SVDMRAIAFLFRGRRLRAEVTPDE (Mut5 bdSUMO; amino acids 56-79)
SEQ ID NO: 14
SVDMTAIAFLFKGRRLRAEFTPDE (Mut6 bdSUMO; amino acids 56-79)
SEQ ID NO: 15
SVDMHAIAFLFKGRRLRAEQTPDE (Mut7 bdSUMO; amino acids 56-79)
SEQ ID NO: 16
SVDMDAIAFLFRGRRLRAECTPDE (Mut8 bdSUMO; amino acids 56-79)
SEQ ID NO: 17
SVDMPAIAFLFKGRRLRAEWTPDE (Mut9 bdSUMO; amino acids 56-79)
SEQ ID NO: 18
SVDMAAIAFLFKGRRLRAEYTPDE (Mut10 bdSUMO; amino acids 56-79)
SEQ ID NO: 19
SVDMTAIAFLFKGRRLRAERTPDE (Mut11 bdSUMO; amino acids 56-79)
SEQ ID NO: 20
SVDMSAIAFLFKGRRLRAEWTPDE (Mut12 bdSUMO; amino acids 56-79)
SEQ ID NO: 21
SVDMSAIAFLFKGRRLRAEHTPDE (Mut13 bdSUMO; amino acids 56-79)
SEQ ID NO: 22
SVDMSAIAFLFKGRRLRAEATPDE (Mut14 bdSUMO; amino acids 56-79)
SEQ ID NO: 23
SVDMNAIAFLFKGRRLRAEWTPDE (Mut15 bdSUMO; amino acids 56-79)
SEQ ID NO: 24
SVDMNAIAFLFKGRRLRAEATPDE (Wt bdSENP1 amino acids 265-354)
SEQ ID NO: 25
GGRKRSETLSVHEASNIVITREILQCLNDKEWLNDEVINLYLELLKERE
LREPNKFLK-CHFFNTFFYKKLINGGYDYKSVRRWTTKRKLG (MutA bdSENP1 amino acids 265-354)
SEQ ID NO: 26
GGRKPSETLSVHEASGIVITREILQCLNDKEWLNDEVINLYLELLKERE
LREPNKFLK-CHFFNTFFYKKLINGGYDYKSVREWTTPRKLG (MutB bdSENP1 amino acids 265-354)
SEQ ID NO: 27
GGRKRSETLSVHEASSIVITREILQCLNDKEWLNDEVINLYLELLKERE
LREPNKFLK-CHFFNTFFYKKLINGGYDYKSVREWTTKRKLG (MutC bdSENP1 amino acids 265-354)
SEQ ID NO: 28
GGRKSSETLSVHEASAIVITREILQCLNDKEWLNDEVINLYLELLKERE
LREPNKFLK-CHFFNTFFYKKLINGGYDYKSVRGWTTVRKLG (MutD bdSENP1 amino acids 265-354)
SEQ ID NO: 29
GGRKPSETLSVHEASEIVITREILQCLNDKEWLNDEVINLYLELLKERE
LREPNKFLK-CHFFNTFFYKKLINGGYDYKSVREWTTQRKLG (MutE bdSENP1 amino acids 265-354)
SEQ ID NO: 30
GGRKRSETLSVHEASGIVITREILQCLNDKEWLNDEVINLYLELLKERE
LREPNKFLKCHFFNTFFYKKLINGGYDYKSVRYWTTARKLG (MutF bdSENP1 amino acids 265-354)
SEQ ID NO: 31
GGRKPSETLSVHEASCIVITREILQCLNDKEWLNDEVINLYLELLKERE
LREPNKFLKCHFFNTFFYKKLINGGYDYKSVRLWTTRRKLG (MutG bdSENP1 amino acids 265-354)
SEQ ID NO: 32
GGRKSSETLSVHEASHIVITREILQCLNDKEWLNDEVINLYLELLKERE
LREPNKFLKCHFFNTFFYKKLINGGYDYKSVRRWTTV-KLG (MutH bdSENP1 amino acids 265-354)
SEQ ID NO: 33
GGRKPSETLSVHEASAIVITREILQCLNDKEWLNDEVINLYLELLKERE
LREPNKFLKCHFFNTFFYKKLIN-GYDYKSVREWTTMRKLG (Muti bdSENP1 amino acids 265-354)
SEQ ID NO: 34
GGRKKSETLSVHEASHIVITREILQCLNDKEWLNDEVINLYLELLKERE
LREPNKFLKCHFFNTFFYKKLINGGYDYKSVREWTTRRKLG (MutJ bdSENP1 amino acids 265-354)
SEQ ID NO: 35
GGRKESETLSVHEASSIVITREILQCLNDKEWLNDEVINLYLELLKERE
LREPNKFLKCHFFNTFFYKKLINGGYDYKSVRSWTTTRKLG (MutK bdSENP1 amino acids 265-354)
SEQ ID NO: 36
GGRKVSETLSVHEASQIVITREILQCLNDKEWLNDEVINLYLELLKERE
LREPNKFLKCHFFNTFFYKKLINGGYDYKSVRVWTTGRKLG (MutL bdSENP1 amino acids 265-354)
SEQ ID NO: 37
GGRKLSETLSVHEASVIVITREILQCLNDKEWLNDEVINLYLELLKERE
LREPNKFLKCHFFNTFFYKKLINGGYDYKSVRPWTTARKLG (MutM bdSENP1 amino acids 265-354)
SEQ ID NO: 38
GGRKASETLSVHEASWIVITREILQCLNDKEWLNDEVINLYLELLKERE
LREPNKFLKCHFFNTFFYKKLINGGYDYKSVRRWTTERKLG (MutN bdSENP1 amino acids 265-354)
SEQ ID NO: 39
GGRKSSETLSVHEASPIVITREILQCLNDKEWLNDEVINLYLELLKERE
LREPNKFLKCHFFNTFFYKKLINGGYDYKSVRRWTTRRKLG (MutO bdSENP1 amino acids 265-354)
SEQ ID NO: 40
GGRKRSETLSVHEASRIVITREILQCLNDKEWLNDEVINLYLELLKERE
LREPNKFLKCHFFNTFFYKKLINGGYDYKSVRGWTTLRKLG (Mut1 bdSUMO residues 1-97)
SEQ ID NO: 41
MSAAGGEEDKKPAGGEGGGAHINLKVKGQDGNEVFFRIKRSTQLKKLMN
AYCDRQSVDMKAIAFLFKGRRLRAERTPDELEMEDGDEIDAMLHQTGG (Mut2 bdSUMO residues 1-97)
SEQ ID NO: 42
MSAAGGEEDKKPAGGEGGGAHINLKVKGQDGNEVFFRIKRSTQLKKLMN
AYCDRQSVDMTAIAFLFKGRRLRAECTPDELEMEDGDEIDAMLHQTGG (Mut3 bdSUMO residues 1-97)
SEQ ID NO: 43
MSAAGGEEDKKPAGGEGGGAHINLKVKGQDGNEVFFRIKRSTQLKKLMN
AYCDRQSVDMHAIAFLFKGRRLRAEKTPDELEMEDGDEIDAMLHQTGG (Mut4 bdSUMO residues 1-97)
SEQ ID NO: 44
MSAAGGEEDKKPAGGEGGGAHINLKVKGQDGNEVFFRIKRSTQLKKLMN
AYCDRQSVDMRAIAFLFRGRRLRAEVTPDELEMEDGDEIDAMLHQTGG (Mut5 bdSUMO residues 1-97)
SEQ ID NO: 45
MSAAGGEEDKKPAGGEGGGAHINLKVKGQDGNEVFFRIKRSTQLKKLMN
AYCDRQSVDMTAIAFLFKGRRLRAEFTPDELEMEDGDEIDAMLHQTGG -continued (Mut6 bdSUMO residues 1-97)
SEQ ID NO: 46
MSAAGGEEDKKPAGGEGGGAHINLKVKGQDGNEVFFRIKRSTQLKKLMN
AYCDRQSVDMHAIAFLFKGRRLRAEQTPDELEMEDGDEIDAMLHQTGG (Mut7 bdSUMO residues 1-97)
SEQ ID NO: 47
MSAAGGEEDKKPAGGEGGGAHINLKVKGQDGNEVFFRIKRSTQLKKLMN
AYCDRQSVDMDAIAFLFRGRRLRAECTPDELEMEDGDEIDAMLHQTGG (Mut8 bdSUMO residues 1-97)
SEQ ID NO: 48
MSAAGGEEDKKPAGGEGGGAHINLKVKGQDGNEVFFRIKRSTQLKKLMN
AYCDRQSVDMPAIAFLFKGRRLRAEQTPDELEMEDGDEIDAMLHQTGG (Mut9 bdSUMO residues 1-97)
SEQ ID NO: 49
MSAAGGEEDKKPAGGEGGGAHINLKVKGQDGNEVFFRIKRSTQLKKLMN
AYCDRQSVDMAAIAFLFKGRRLRAEYTPDELEMEDGDEIDAMLHQTGG (Mut10 bdSUMO residues 1-97)
SEQ ID NO: 50
MSAAGGEEDKKPAGGEGGGAHINLKVKGQDGNEVFFRI KRSTQLKKLM
NAYCDRQSVDMTAIAFLFKGRRLRAERTPDELEMEDGDEIDAMLHQTGG (Mut11 bdSUMO residues 1-97)
SEQ ID NO: 51
MSAAGGEEDKKPAGGEGGGAHINLKVKGQDGNEVFFRIKRSTQLKKLMN
AYCDRQSVDMSAIAFLFKGRRLRAEWTPDELEMEDGDEIDAMLHQTGG (Mut12 bdSUMO residues 1-97)
SEQ ID NO: 52
MSAAGGEEDKKPAGGEGGGAHINLKVKGQDGNEVFFRI KRSTQLKKLM
NAYCDRQSVDMSAIAFLFKGRRLRAEHTPDELEMEDGDEIDAMLHQTGG (Mut13 bdSUMO residues 1-97)
SEQ ID NO: 53
MSAAGGEEDKKPAGGEGGGAHINLKVKGQDGNEVFFRI KRSTQLKKLM
NAYCDRQSVDMSAIAFLFKGRRLRAEATPDELEMEDGDEIDAMLHQTGG (Mut14 bdSUMO residues 1-97)
SEQ ID NO: 54
MSAAGGEEDKKPAGGEGGGAHINLKVKGQDGNEVFFRIKRSTQLKKLMN
AYCDRQSVDMNAIAFLFKGRRLRAEWTPDELEMEDGDEIDAMLHQTGG (Mut15 bdSUMO residues 1-97)
SEQ ID NO: 55
MSAAGGEEDKKPAGGEGGGAHINLKVKGQDGNEVFFRIKRSTQLKKLMN
AYCDRQSVDMNAIAFLFKGRRLRAEATPDELEMEDGDEIDAMLHQTGG (MutA bdSENP1 residues 248-481)
SEQ ID NO: 56
PFVPLTDEDEDNVRHALGGRKPSETLSVHEASGIVITREILQCLNDKEW
LNDEVINLYLELLKERELREPNKFLKCHFFNTFFYKKLINGGYDYKSVR
EWTTPRKLGYNLIDCDKIFVPIHKDVHWCLAVINIKEKKFQYLDSLGYM
DMKALRILAKYLVDEVKDKSGKQIDVHAWKQEGVQNLPLQENGWDCGMF
MLKYIDFYSRDMELVFGQKHMSYFRRRTAKEILDLKAG (MutB bdSENP1 residues 248-481)
SEQ ID NO: 57
PFVPLTDEDEDNVRHALGGRKRSETLSVHEASSIVITREILQCLNDKEW
LNDEVINLYLELLKERELREPNKFLKCHFFNTFFYKKLINGGYDYKSVR
EWTTKRKLGYNLIDCDKIFVPIHKDVHWCLAVINIKEKKFQYLDSLGYM
DMKALRILAKYLVDEVKDKSGKQIDVHAWKQEGVQNLPLQENGWDCGMF
MLKYIDFYSRDMELVFGQKHMSYFRRRTAKEILDLKAG (MutC bdSENP1 residues 248-481)
SEQ ID NO: 58
PFVPLTDEDEDNVRHALGGRKSSETLSVHEASAIVITREILQCLNDKEW
LNDEVINLYLELLKERELREPNKFLKCHFFNTFFYKKLINGGYDYKSVR
GWTTVRKLGYNLIDCDKIFVPIHKDVHWCLAVINIKEKKFQYLDSLGYM
DMKALRILAKYLVDEVKDKSGKQIDVHAWKQEGVQNLPLQENGWDCGMF
MLKYIDFYSRDMELVFGQKHMSYFRRRTAKEILDLKAG (MutD bdSENP1 residues 248-481)
SEQ ID NO: 59
PFVPLTDEDEDNVRHALGGRKPSETLSVHEASEIVITREILQCLNDKEW
LNDEVINLYLELLKERELREPNKFLKCHFFNTFFYKKLINGGYDYKSVR
EWTTQRKLGYNLIDCDKIFVPIHKDVHWCLAVINIKEKKFQYLDSLGYM
DMKALRILAKYLVDEVKDKSGKQIDVHAWKQEGVQNLPLQENGWDCGMF
MLKYIDFYSRDMELVFGQKHMSYFRRRTAKEILDLKAG (MutE bdSENP1 residues 248-481)
SEQ ID NO: 60
PFVPLTDEDEDNVRHALGGRKRSETLSVHEASGIVITREILQCLNDKEW
LNDEVINLYLELLKERELREPNKFLKCHFFNTFFYKKLINGGYDYKSVR
YWTTARKLGYNLIDCDKIFVPIHKDVHWCLAVINIKEKKFQYLDSLGYM
DMKALRILAKYLVDEVKDKSGKQIDVHAWKQEGVQNLPLQENGWDCGMF
MLKYIDFYSRDMELVFGQKHMSYFRRRTAKEILDLKAG (MutF bdSENP1 residues 248-481)
SEQ ID NO: 61
PFVPLTDEDEDNVRHALGGRKPSETLSVHEASCIVITREILQCLNDKEW
LNDEVINLYLELLKERELREPNKFLKCHFFNTFFYKKLINGGYDYKSVR
LWTTRRKLGYNLIDCDKIFVPIHKDVHWCLAVINIKEKKFQYLDSLGYM
DMKALRILAKYLVDEVKDKSGKQIDVHAWKQEGVQNLPLQENGWDCGMF
MLKYIDFYSRDMELVFGQKHIMSYFRRRTAKEILDLKAG (MutG bdSENP1 residues 248-481)
SEQ ID NO: 62
PFVPLTDEDEDNVRHALGGRKSSETLSVHEASHIVITREILQCLNDKEW
LNDEVINLYLELLKERELREPNKFLKCHFFNTFFYKKLINGGYDYKSVR
RWTTVKLGYNLIDCDKIFVPIHKDVHWCLAVINIKEKKFQYLDSLGYMD
MKALRILAKYLVDEVKDKSGKQIDVHAWKQEGVQNLPLQENGWDCGMFM
LKYIDFYSRDMELVFGQKHMSYFRRRTAKEILDLKAG (MutH bdSENP1 residues 248-481)
SEQ ID NO: 63
PFVPLTDEDEDNVRHALGGRKPSETLSVHEASAIVITREILQCLNDKEW
LNDEVINLYLELLKERELREPNKFLKCHFFNTFFYKKLINGYDYKSVRE
WTTMRKLGYNLIDCDKIFVPIHKDVHWCLAVINIKEKKFQYLDSLGYMD
MKALRILAKYLVDEVKDKSGKQIDVHAWKQEGVQNLPLQENGWDCGMFM
LKYIDFYSRDMELVFGQKHMSYFRRRTAKEILDLKAG (Muti bdSENP1 residues 248-481)
SEQ ID NO: 64
PFVPLTDEDEDNVRHALGGRKKSETLSVHEASHIVITREILQCLNDKEW
LNDEVINLYLELLKERELREPNKFLKCHFFNTFFYKKLINGGYDYKSVR
EWTTRRKLGYNLIDCDKIFVPIHKDVHWCLAVINIKEKKFQYLDSLGYM
DMKALRILAKYLVDEVKDKSGKQIDVHAWKQEGVQNLPLQENGWDCGMF
MLKYIDFYSRDMELVFGQKHMSYFRRRTAKEILDLKAG (MutJ bdSENP1 residues 248-481)
SEQ ID NO: 65
PFVPLTDEDEDNVRHALGGRKESETLSVHEASSIVITREILQCLNDKEW
LNDEVINLYLELLKERELREPNKFLKCHFFNTFFYKKLINGGYDYKSVR
SWTTTRKLGYNLIDCDKIFVPIHKDVHWCLAVINIKEKKFQYLDSLGYM
DMKALRILAKYLVDEVKDKSGKQIDVHAWKQEGVQNLPLQENGWDCGMF
MLKYIDFYSRDMELVFGQKHIMSYFRRRTAKEILDLKAG (MutK bdSENP1 residues 248-481)
SEQ ID NO: 66
PFVPLTDEDEDNVRHALGGRKVSETLSVHEASQIVITREILQCLNDKEW
LNDEVINLYLELLKERELREPNKFLKCHFFNTFFYKKLINGGYDYKSVR
VWTTGRKLGYNLIDCDKIFVPIHKDVHWCLAVINIKEKKFQYLDSLGYM
DMKALRILAKYLVDEVKDKSGKQIDVHAWKQEGVQNLPLQENGWDCGMF
MLKYIDFYSRDMELVFGQKHMSYFRRRTAKEILDLKAG (MutL bdSENP1 residues 248-481)
SEQ ID NO: 67
PFVPLTDEDEDNVRHALGGRKLSETLSVHEASVIVITREILQCLNDKEW
LNDEVINLYLELLKERELREPNKFLKCHFFNTFFYKKLINGGYDYKSVR
PWTTARKLGYNLIDCDKIFVPIHKDVHWCLAVINIKEKKFQYLDSLGYM
DMKALRILAKYLVDEVKDKSGKQIDVHAWKQEGVQNLPLQENGWDCGMF
MLKYIDFYSRDMELVFGQKHMSYFRRRTAKEILDLKAG (MutM bdSENP1 residues 248-481)
SEQ ID NO: 68
PFVPLTDEDEDNVRHALGGRKASETLSVHEASWIVITREILQCLNDKEW
LNDEVINLYLELLKERELREPNKFLKCHFFNTFFYKKLINGGYDYKSVR
RWTTERKLGYNLIDCDKIFVPIHKDVHWCLAVINIKEKKFQYLDSLGYM
DMKALRILAKYLVDEVKDKSGKQIDVHAWKQEGVQNLPLQENGWDCGMF
MLKYIDFYSRDMELVFGQKHMSYFRRRTAKEILDLKAG (MutN bdSENP1 residues 248-481)
SEQ ID NO: 69
PFVPLTDEDEDNVRHALGGRKSSETLSVHEASPIVITREILQCLNDKEW
LNDEVINLYLELLKERELREPNKFLKCHFFNTFFYKKLINGGYDYKSVR
RWTTRRKLGYNLIDCDKIFVPIHKDVHWCLAVINIKEKKFQYLDSLGYM
DMKALRILAKYLVDEVKDKSGKQIDVHAWKQEGVQNLPLQENGWDCGMF
MLKYIDFYSRDMELVFGQKHIMSYFRRRTAKEILDLKAG -continued (MutO bdSENP1 residues 248-481)
SEQ ID NO: 70
PFVPLTDEDEDNVRHALGGRKRSETLSVHEASRIVITREILQCLNDKEW
LNDEVINLYLELLKERELREPNKFLKCHFFNTFFYKKLINGGYDYKSVR
GWTTLRKLGYNLIDCDKIFVPIHKDVHWCLAVINIKEKKFQYLDSLGYM
DMKALRILAKYLVDEVKDKSGKQIDVHAWKQEGVQNLPLQENGWDCGMF
MLKYIDFYSRDMELVFGQKHMSYFRRRTAKEILDLKAG (MBP)
SEQ ID NO: 71
AGTGTSKTEEGKLVIWINGDKGYNGLAEVGKKFEKDTGIKVTVEHPDKL
EEKFPQVAATGDGPDIIFWAHDRFGGYAQSGLLAEITPDKAFQDKLYPF
TWDAVRYNGKLIAYPIAVEALSLIYNKDLLPNPPKTWEEIPALDKELKA
KGKSALMFNLQEPYFTWPLIAADGGYAFKYENGKYDIKDVGVDNAGAKA
GLTFLVDLIKNKHMNADTDYSIAEAAFNKGETAMTINGPWAWSNIDTSK
VNYGVTVLPTFKGQPSKPFVGVLSAGINAASPNKELAKEFLENYLLTDE
GLEAVNKDKPLGAVALKSYEEELAKDPRIAATMENAQKGEIMPNIPQMS
AFWYAVRTAVINAASGRQTVDEALKDAQTN
The first four residues are part of a short linker
between SUMOs and MBP.

(WT bdSENP1 amino acids 1-481)
SEQ ID NO: 73
MGALTDSRKRVSADHRLHPSFPPSPPPPSKRTKLAPLLPVSSPPPLHYA
SPSSAAPGPSSSAAAAAATASTSSHSSLPHPRRRLPPAPPISRPIHGPQ
RVRRSFRGGNSRPNSNPPWYSPSPPPKPLGLDQYADLVYSVTHPPRPTP
AVHVPRGTEAIPEVVMVDDNEDIRQDKEDEQDVEEEAKAKVVGRKVPLY
KELYEKSSRQRDARLRTLEFEVQLAEKGRLGLERLAEVLPRITPNKEEV
PEPFVPLTDEDEDNVRHALGGRKRSETLSVHEASNIVITREILQCLNDK
EWLNDEVINLYLELLKERELREPNKFLKCHFFNTFFYKKLINGGYDYKS
VRRWTTKRKLGYNLIDCDKIFVPIHKDVHWCLAVINIKEKKFQYLDSLG
YMDMKALRILAKYLVDEVKDKSGKQIDVHAWKQEGVQNLPLQENGWDCG
MFMLKYIDFYSRDMELVFGQKHIMSYFRRRTAKEILDLKAG

EXAMPLES

Figure 6:
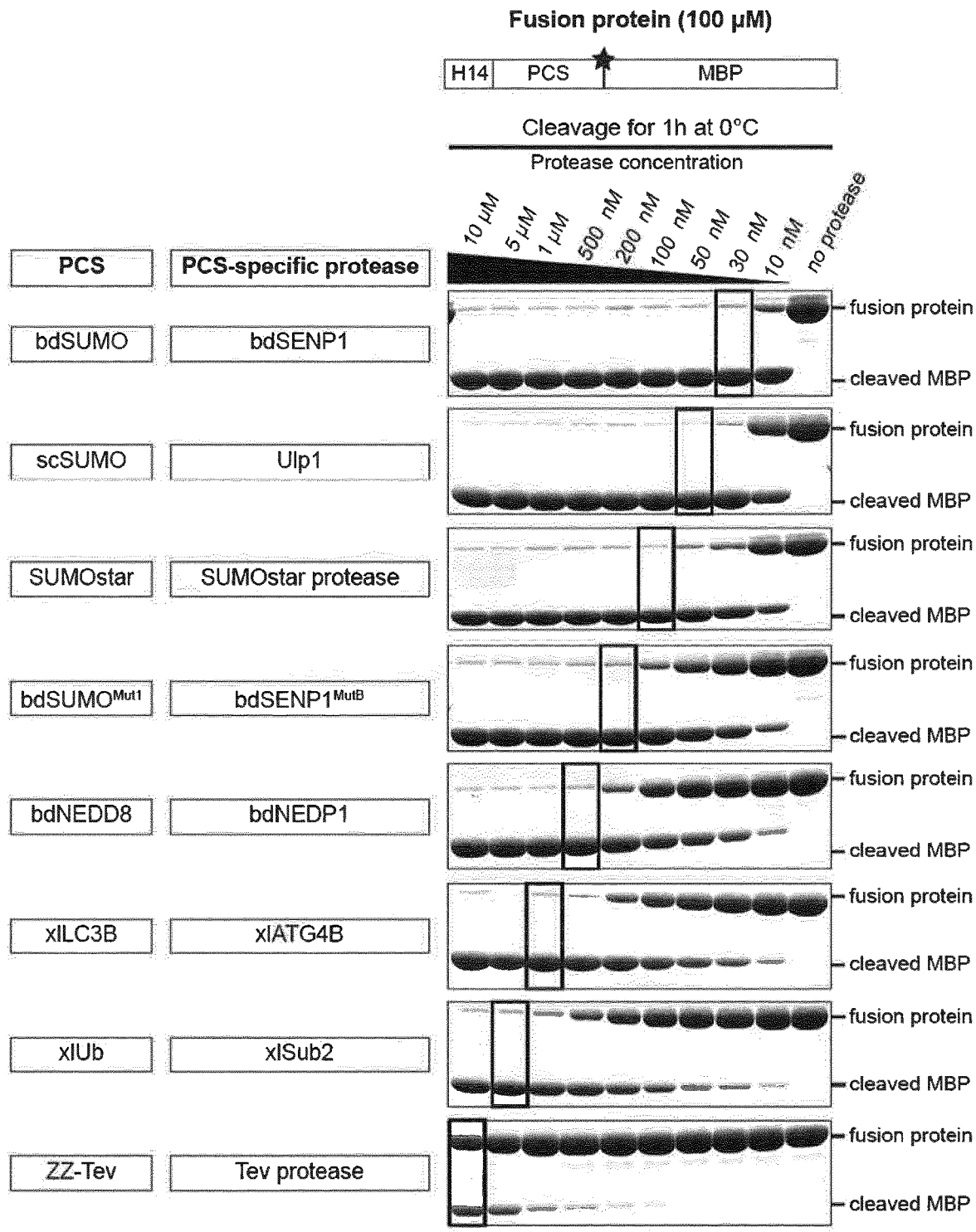
FIG. 6 Proteolytic efficiency of the $bdSENP1^{MutB}$ protease and other site-specific proteases. The proteolytic efficiency of different site-specific proteases was tested in solution for 1 h at 0° C. Different amount of a given protease were incubated with 100 μM of the corresponding tagged MBP. Samples were resolved by SDS-PAGE to separate the full-length fusion protein from the C-terminal cleaved MBP. Samples highlighted with a black box indicate the lowest protease concentration at which ≈95% of the cognate substrate is cleaved. The experiments are ordered in the figure from the most to the least efficient protease used in this experiment.

Example 1 Cleavage Efficiency bdSENP1$^{MutB}$ and Other Site Specific Proteases So far, bdSENP1 and Ulp1 are the most active Ubl-specific proteases known (Frey & Görlich 2014a). Around 15-50 nM of these two proteases were required to efficiently cleave the cognate substrate for 1 h at 0° C. (FIG. 6). Other commonly used Ubl-specific proteases (i.e. xlAtg4, xlSub2 and bdNEDP1) are from 15 to 150-fold less efficient than bdSENP1 and Ulp1. Here, we showed that bdSENP1$^{MutB}$ protease was only 5-fold less efficient as compared bdSENP1 or Ulp1. bdSENP1$^{MutB}$ protease is therefore a more attractive option to some wild type Ubl-specific proteases.

This example also shows that the bdSENP1$^{MutB}$ protease is around 1000-fold more efficient than the site-specific protease from the tobacco etch virus (TEV protease). For instance, only 200 nM of bdSENP1$^{MutB}$ protease were enough to cleave ≈95% of the cognate substrate (bdSUMOmut 1), while even 10 µM of TEV protease were not enough to cleave the same amount of fusion protein at the same conditions of incubation (FIG. 6). Although TEV protease is the most extensively used protease for tag removal, our data proves that bdSENP1$^{MutB}$ represents a more powerful tool for the same propose.

Materials and Methods

Cleavage reactions were carried out using cleavage buffer (45 mM Tris/HCl PH 7.5, 250 mM NaCl, 2 mM MgCl$_2$, 250 mM sucrose, 10 mM DTT) in a total volume of 20 µl. Prior to the reaction, substrates and proteases were diluted with cleavage buffer to 2-fold of the concentration required for the reaction. Equal volumes of diluted substrate and proteases were mixed in order to start the reaction. For every reaction, 100 µM of each MBP-tagged substrate were incubated with various amounts of a given protease (from 10 nM to 10 µM) for 1h on ice. The cleavage reactions were stopped by adding 180 µl of SDS sample buffer (3% SDS, 125 mM Tris/HCl (pH 6.8), 50 mM DTT, 1M sucrose and Coomassie brilliant blue G250). A sample corresponding to 2.5 µg of the bdSUMO$^{Mut1}$-tagged substrate was resolved by SDS-PAGE and further stained by Coomassie blue. Control samples without protease were included in the assays. The proteases tested were: bdSENP1 from B. distachyon, Ulp1 from S. cerevisiae, SUMOstar protease, bdSENP1$^{MutB}$ protease, bdNEDP1 from B. distachyon, xlATG4B and xlSub2 from X. leavis and TEV protease.

Example 2 bdSENP1$^{MutB}$ and SUMOstar are Orthogonal Proteases

Figure 7:
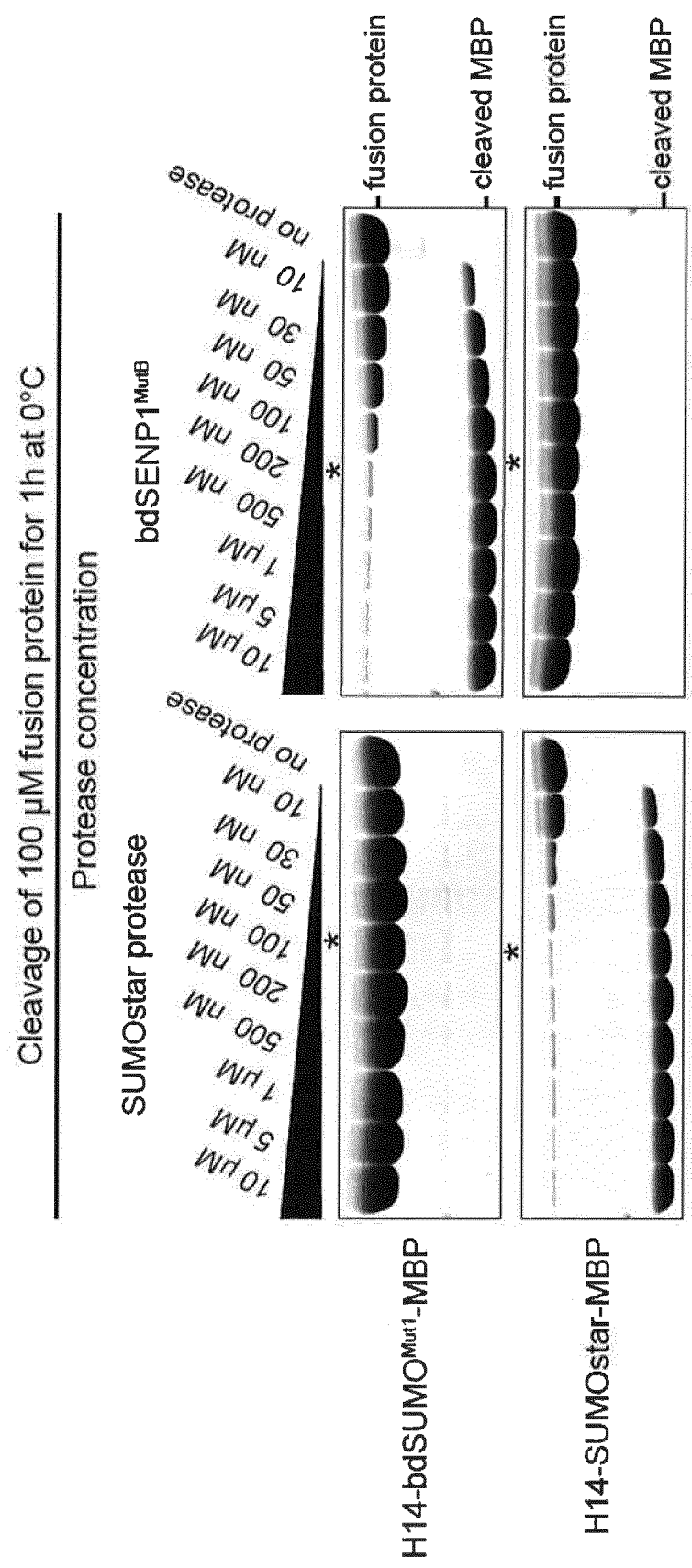
FIG. 7 $bdSENP1^{MutB}$ and SUMOstar proteases have fully orthogonal specificities. Samples containing 100 μM of a given H14-SUMO-MBP fusion protein were incubated with increasing concentration of either $bdSENP1^{MutB}$ or SUMOstar proteases for 1 h at 0° C. The full-length SUMO-fusion protein was separated from the C-terminal cleaved MBP by SDS-PAGE. The asterisks represent the protease concentration at which ≈95% of the cognate SUMO-fusion protein is cleaved.

To test the orthogonality between the SUMOvera and SUMOstar systems, bdSUMO$^{Mut1}$- and SUMOstar-MBP fusions were incubated for 1 h at 0° C. with increasing concentrations of either bdSENP1$^{MutB}$ or SUMOstar protease (FIG. 7). On one hand, bdSENP1$^{MutB}$ protease only cleaved its cognate substrate at a concentration of 200 nM, whereas the SUMOstar-MBP fusion remained intact even at the highest protease concentration of 10 µM. On the other hand, SUMOstar protease only recognized SUMOstar-MBP and left intact the bdSUMO$^{Mut1}$-MBP fusion protein even at the highest SUMOstar protease concentration of 10 µM. Note that 10 µM of either protease represents up to 1000-fold more protease needed for complete cleavage of the cognate substrate, and even so no protease cross-reactivity was observed. Therefore, the SUMOvera and the SUMOstar systems have indeed truly orthogonal specificities.

Materials and Methods

Cleavage reactions were performed, stopped and analyzed as described in Example 1. The only exceptions are that bdSUMO$^{Mut1}$ and SUMOstar fusion proteins were incubated with increasing concentration of each protease.

Example 3 Expression of bdSUMO$^{Mut1}$-Fusion Proteins in S. cerevisiae

Virtually, any protein tagged with a wild type SUMO protein is immediately cleaved if expressed in any eukaryotic host. SUMOstar is so far the only example of a SUMO protein that is a stable tag in different eukaryotic systems (Liu et al. 2008; Peroutka et al. 2008). We tested whether bdSUMO$^{Mut1}$ would also be resistant to cleavage by Ulp1 in vivo and therefore stable in yeast cells.

Figure 8:
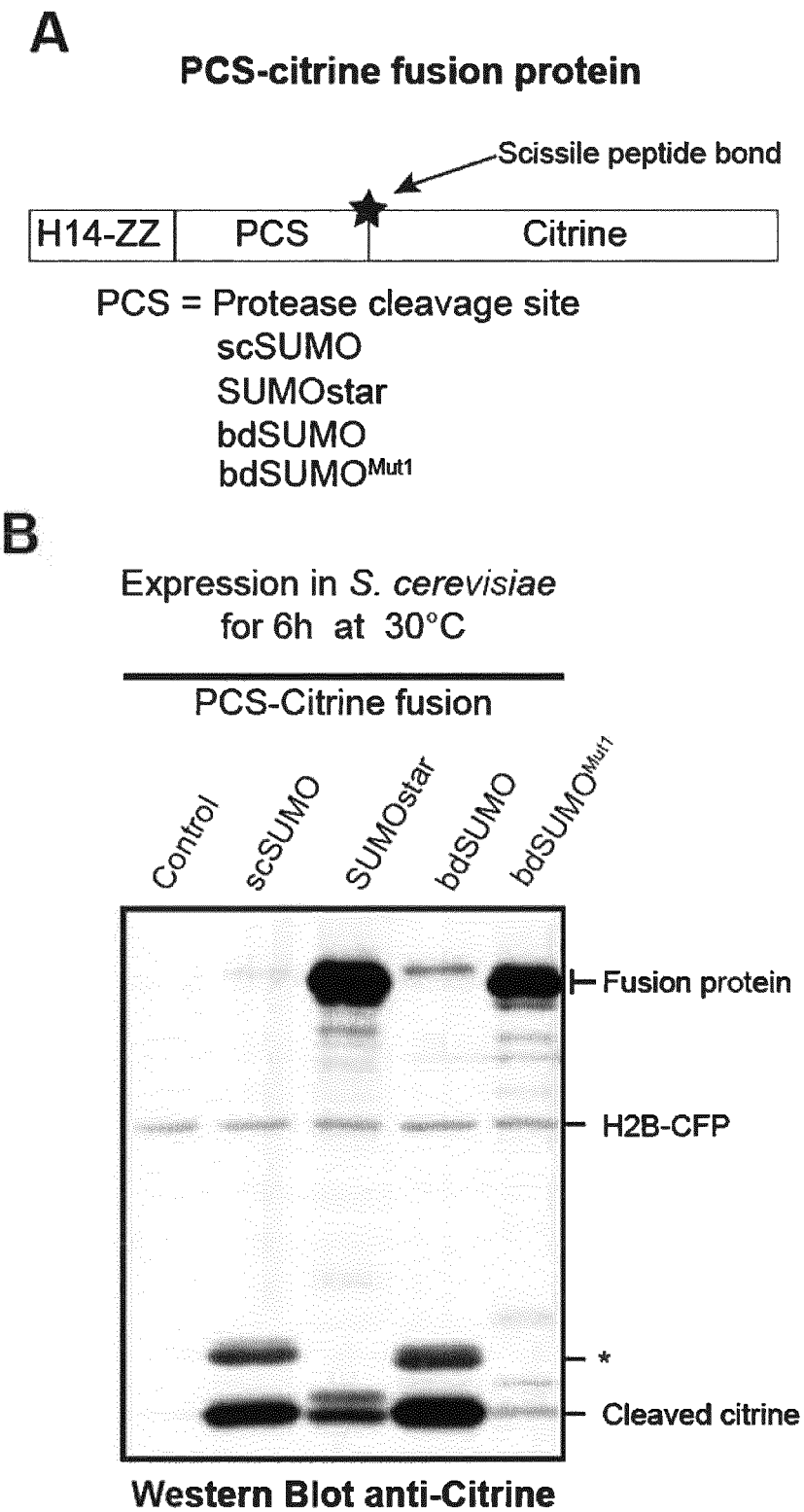
FIG. 8 $bdSUMO^{Mut1}$-fusion proteins are stable in $S.\ cerevisiae$. (A) Scheme of the SUMO fusion proteins overexpressed in $S.\ cerevisiae$ (H14: poly-histidine tag, ZZ: double copy of the Z-domain from staphylococcal protein A). (B) After 6h of protein over-expression at 30° C., the stability of different SUMO fusion proteins was analyzed by western blot using an anti-citrine antibody. Cyan fluorescent protein fused to histone 2B (H2B-CFP) was used as an internal control to confirm even loading of the samples. Cross-reactivity between the anti-citrine antibody and the ZZ-tag is indicated by *. An empty yeast lysate was used as a negative control.

To this end, we over-expressed citrine tagged with scSUMO, SUMOstar, bdSUMO or bdSUMO$^{Mut1}$ in S. cerevisiae to test if the fusion protein would remain as a full-length product. The stability of the fusion proteins was analyzed by western blot using an anti-citrine antibody (FIG. 8). As expected, scSUMO- and bdSUMO-tagged citrines were completely cleaved, whereas SUMOstar- and bdSUMO$^{Mut1}$-tagged proteins remained intact even after 6h of over-expression. In fact, bdSUMO$^{Mut1}$ was the most stable fusion tag during recombinant protein expression in yeast (even more than SUMOstar) since up to ≈100% of the overexpressed bdSUMO$^{Mut1}$-tagged protein remained as full-length and almost no cleaved citrine was detected. These results suggest that bdSUMO$^{Mut1}$ represents even a better choice than SUMOstar as a SUMO fusion tag for expression in S. cerevisiae.

Materials and Methods

For the over-expression of the SUMO-citrine fusion proteins, the respective expression plasmids were transformed in *S. cerevisiae* strain SFY123 (MATa, ADE2, his3-11, leu2-3, 112 LYS2, trp1-1, ura3 can1-100, H2B-CFP::Trp1) using the PEG/LiAc protocol described in (Gietz & Schiestl 2007). Next, a single transformed colony was picked to inoculate a starting preculture of SD-medium supplemented with 2% (w/v) of glucose. After overnight incubation at 30° C., cells were pelleted by centrifugation for 5 min at 2,000 rpm and further resuspended using fresh medium supplemented with 2% (w/v) of glucose and 2% (w/v) of raffinose. This last process was repeated twice. Centrifugation and subsequent resuspension of cells with fresh medium supplemented with 2% (w/v) of glucose and 2% (w/v) of raffinose were repeated twice. Resuspended cells were then used to inoculate 250 ml of SD-medium supplemented with 2% (w/v) of raffinose to an initial concentration of $OD_{600} \approx 0.2$. The culture was incubated at 30° C. with shaking until exponential growth phase was reached ($OD_{600} \approx 0.8$-1.0). Over-expression of the SUMO-citrine fusion proteins was induced by the addition of 2% (w/v) of galactose for 6 h at 30° C. while shaking. After protein over-expression, yeast cells were pelleted by centrifugation for 10 min at 2,000 rpm and 25° C. and further resuspended in resuspension buffer (45 mM Tris/HCl PH 7.5, 250 mM NaCl, 20 mM imidazole, 5 mM DTT).

To analyze the stability of the SUMO-citrine proteins, the resuspended cells were used to generate lysates by TCA/NaOH extraction as described in (Zuk 1998). Cell lysates corresponding to 35mOD of cells expressing the citrine fusion proteins were resolved by SDS-PAGE and analyzed by western blot. An anti-GFP primary antibody was used to detect the presence of cleaved citrine and/or the full-length SUMO-citrine fusion protein. A cell lysate lacking a SUMO-tagged citrine was used as negative control.

Example 4 bdSUMO$^{Mut1}$ is a Stable Tag in Eukaryotic Cellular Extracts

Figure 9:
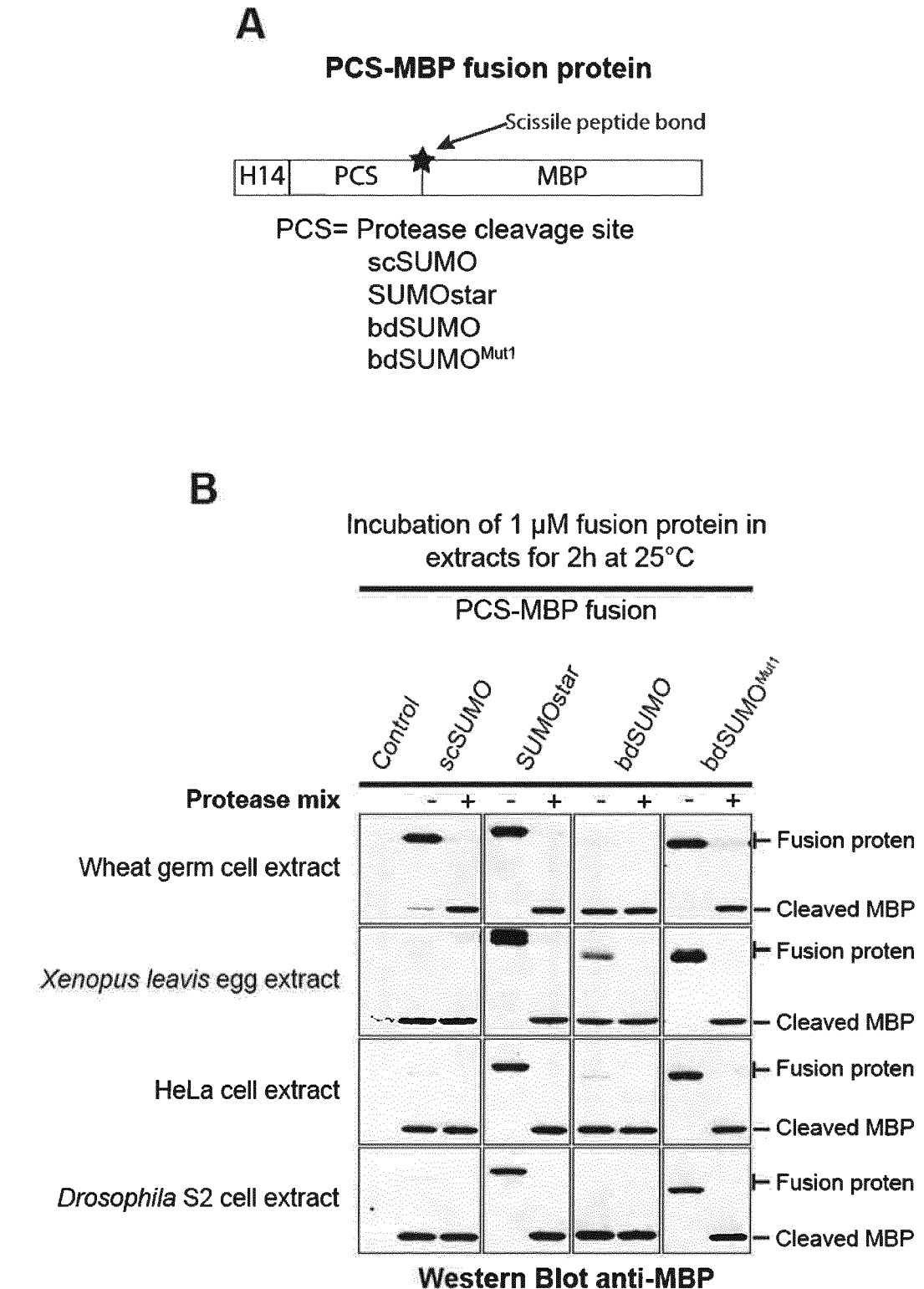
FIG. 9 $bdSUMO^{Mut1}$ is a stable fusion tag in eukaryotic lysates. (A) Figure of fusion proteins used to test the stability of different SUMO proteins in several eukaryotic lysates. (H14: poly-histidine tag, MBP: $E.\ coli$ Maltose Binding Protein). (B) The stability of different SUMO fusion proteins was analyzed by western blot using an anti-MBP antibody after incubation in highly concentrated eukaryotic extracts for 2 h at 30° C. The presence of a C-terminal cleaved MBP indicates the cleavage of the SUMO tag by the endogenous SUMO specific proteases. Samples with a protease mix (Ulp1, SUMOstar protease, bdSENP1 and bdSENP1$^{MutB}$ protease, 1 µM each) were included to rule out the presence of protease inhibitory substances present in the lysates.

We also analyzed the stability of scSUMO-, SUMOstar-, bdSUMO- and bdSUMO$^{Mut1}$-MBP fusion proteins in different eukaryotic extracts. Each MBP fusion protein was incubated in a highly concentrated extract for 2 h at 25° C. and further analyzed by western blot (FIG. 9). Proteins tagged with SUMOstar and bdSUMO$^{Mut1}$ were not cleaved in all samples, whereas the scSUMO as well as the bdSUMO fusions proteins were cleaved to different extents. Samples including a "protease mix" (Ulp1, SUMOstar protease, bdSENP1 and bdSENP1$^{MutB}$ protease, 1 μM each) showed that there was not any inhibitory substance that could have prevented endogenous SUMO-specific proteins to cleave either the SUMOstar or the bdSUMO$^{Mut1}$ fusion proteins. Therefore, these results confirm that bdSUMO$^{Mut1}$ is also a suitable fusion tag that can be used in virtually any eukaryotic host.

Materials and Methods

The stability of the different SUMO-tagged MBP fusion proteins was tested in different eukaryotic extracts (wheat germ extract, *Xenopus laevis* egg extract, rabbit reticulocytes extract, HeLa cell extract and *Drosophila* S2 cell extract). The preparation of the lysates was performed as described in (Mureev et al. 2009; Kovtun et al. 2010; Blow & Laskey 1986; Crevel & Cotterill 1991; Endo et al. 2010; Jackson & Hunt 1983). For a 12.5 μl volume reaction, 1 μM of SUMO-tagged substrate was incubated with 10 μl of each lysate for 2 h at 25° C. in the presence and absence of a protease mix containing 1 μM of different SUMO-specific proteases (Ulp1, SUMOstar, bdSENP1 and bdSENP1$^{MutB}$ protease). Finally, the reaction was stopped by adding SDS sample buffer (3% SDS, 125 mM Tris/HCl, (pH 6.8), 50 mM DTT, 1 M sucrose and coomassie brilliant blue G250) to a final volume of 100 μl. The stability of the substrates was analyzed by western blot using an anti-MBP primary antibody.

Example 5 Purification of a Hetero-Dimeric Complex in Yeast

Two or more site-specific proteases are used to purify protein complexes with defined subunit stoichiometry (Frey & Görlich 2014b). Although this technology is straightforward and requires only of proteases with mutually exclusive substrate specificity, it has been so far apply in prokaryotic systems such as *E. coli*. Here, we show that the SUMOvera system together with the SUMOstar system can be used to purify dimeric protein complexes that are expressed in *S. cerevisiae*. As proof of principle, we selected the high affinity hetero-dimeric complex composed of the anti-GFP nanobody (Nb) (Kirchhofer et al. 2010) and the GFP-like protein named citrine (Heikal et al. 2000). Nb was cloned as an H14-bdSUMO$^{Mut1}$-fusion protein, whereas citrine was fused to an N-terminal ZZ-SUMOstar tag (FIG. 10-A).

Figure 10:
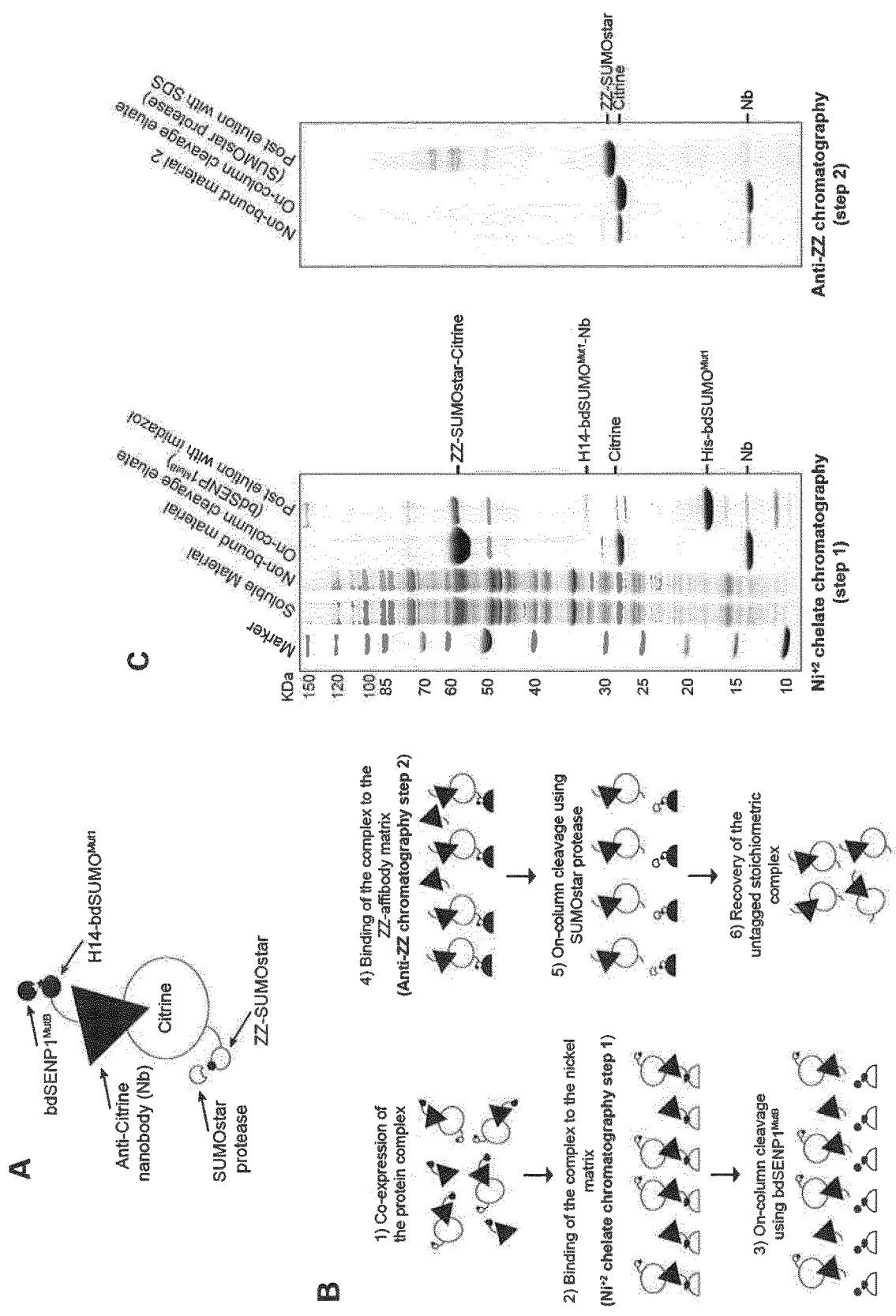
FIG. 10 Purification of a stoichiometric protein complex in yeast. (A) As a model for a hetero-dimeric complex, an anti-citrine nanobody (Nb) tagged with bdSUMO$^{Mut1}$ and SUMOstar-tagged citrine were used. (B) Scheme of the purification processes composed of two consecutive chromatographic steps. The dimeric complex was co-expressed in S. cerevisiae as a soluble form for 6 h at 30° C. (soluble material). First, the complex was isolated through a polyhistidine tag (H14) fused to bdSUMO$^{Mut1}$ using a Ni$^{2+}$ chelate matrix (first chromatographic step). The complex was then eluated by in-column cleavage using bdSENP1$^{MutB}$ (On-column cleavage eluate 1). For the second purification step, the eluate 1 was loaded onto an anti-Z domain matrix to bind to the ZZ-tag fused to SUMOstar. The stoichiometric and highly pure complex was then finally eluted by on-column cleavage using the SUMOstar protease (On-column cleavage eluate 2). (C) Protein samples corresponding to 35mOD units of cells or 1/1000 of the total purified protein were analyzed by SDS-PAGE and further stained by coomassie blue. Labels on the middle of both images side define the protein identity of each band in both gels.

After the co-expression of both proteins, we used two consecutive capture-and-realize chromatographic steps as described in (Frey & Görlich 2014b) for the purification of the Nb·Citrine complex (FIG. 10-B). For the first chromatographic step, the cellular lysate containing the complex (soluble material) was loaded onto a column containing a $Ni^{2+}$ chelate matrix to immobilize the dimeric complex via the H14-bdSUMO$^{Mut1}$-Nb fusion protein. The non-bound material is then removed from the column after washing the matrix (non-bound material). The elution of the protein complex was then achieved by on-column protein cleavage using bdSENP1$^{MutB}$ protease. Notably, untagged citrine was present in the eluted complex due to the partial cleavage ZZ-SUMOstar tag by endogenous Ulp1 as observed in (FIG. 8). After a second affinity chromatographic step, the stoichiometric protein complex was obtained since the surplus of untagged Nb from elute 1 as well as the untagged Citrine were removed from the protein preparation (non-bound material 2). The stoichiometric complex is obtained by a second on-column protein cleavage using SUMOstar protease. Finally, the use of bdSENP1$^{MutB}$ and the SUMOstar proteases allowed obtaining an untagged and a purer complex as both affinity tags and all contaminants remained bound to both affinity matrices (Post elution with imidazole and SDS).

Materials and Methods

The transformation of the Nb·Citrine complex was performed in *S. cerevisiae* strain SFY123 (MATa, ADE2, his3-11, 15 leu2-3, 112 LYS2, trp1-1, ura3, can1-100). One plasmid codified for the fusion protein H14-bdSUMO$^{Mut1}$-Nb and the second for the ZZ-SUMOstar-Citrine protein. Expression was performed as described in Example 3. After expression, the yeast pellet was resuspended in resuspension buffer (50 mM Tris/HCl PH 7.5, 150 mM NaCl, 20 mM imidazole, 5 mM DTT) to a final $OD_{600}$ of 20-50/ml. A cocktail of different protease inhibitors was added to the resuspended cells to a final concentration of 1×. The stock (500×) of protease inhibitors contained the following compounds: 5 mg/ml aprotinin, 5 mg/ml leupeptin, 2.5 mg/ml elastatinal, 2.5 mg/ml chymostatin and 0.5 mg/ml pepstatin A. Cells were snap-frozen in liquid nitrogen and immediately thawn in a hot water bath for 10-15 min. The cellular membrane was disrupted using glass beads and constant vortexing to generate a cell lysate. Cell debris and insoluble material was removed from the lysed cells by ultracentrifugation at 38,000 rpm and 4° C. for 1.5h.

The purification of binary protein complexes was performed as described in (Frey & Görlich 2014b). Briefly, the cleared yeast lysate was incubated with $Ni^{2+}$ chelate beads for 1 h at 4° C. Subsequently, beads were place in a column and contaminant proteins were removed by adding 2 column volume (CV) of resuspension buffer. The protein complex was then eluted by adding 1CV elution buffer containing 200 nM of bdSENP1$^{MutB}$ protease for 1 h at 4° C. For the second purification step, the complex was immobilized via the ZZ-tag (tandem repeat of the Z domain from staphylococcal protein A) using silica beads coupled to an anti ZZ-domain affibody. The sample was incubated with 2 ml of anti Z-domain beads for 1 h at 4° C. After incubation, beads were washed with 2CV of resuspension buffer. For protein elution, silica beads were incubated with resuspension buffer supplemented with 100 nM of SUMOstar protease for 1 h at 4° C. After elution, samples were pooled and frozen in liquid nitrogen for storage at −80°. Protein samples were taken at different steps of the expression and purification of the complex and analyzed by SDS-PAGE.

Example 6. Over-Expression of bdSENP1$^{MutB}$ Protease in *S. cerevisiae*

Figure 11:
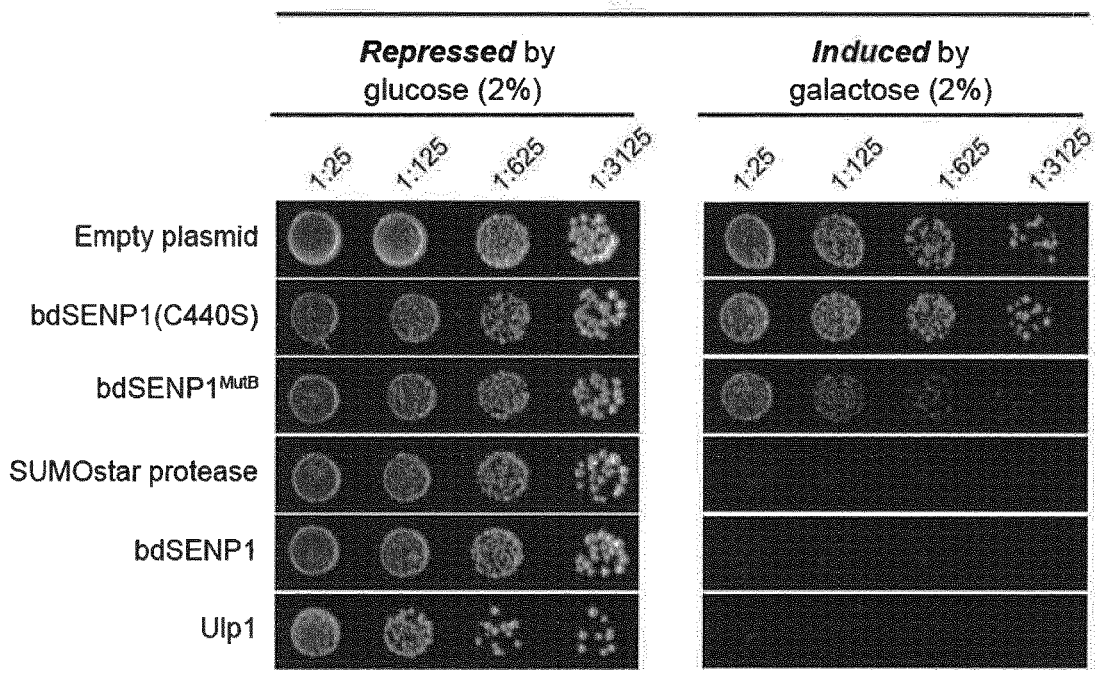
FIG. 11 bdSENP1$^{MutB}$ protease can be ectopically overexpressed in S. cerevisiae. The viability of the yeast cells over-expressing a SUMO-specific protease was tested. Cells were subjected to different 10-fold dilutions (from 1:25 to 1:3125 v/v) and further spotted on plates containing glucose or galactose to repress and induce protein expression, respectively. Cells transformed with an empty vector or encoding a catalytically dead protease (C440S) were used as negative controls.
Figure 12:
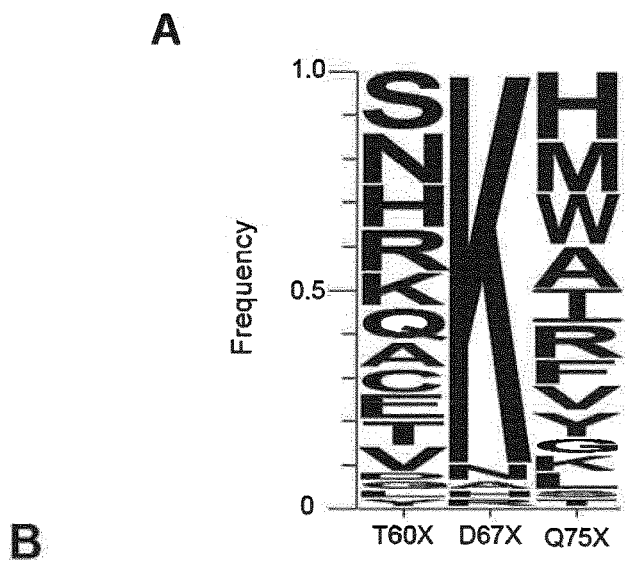
FIG. 12 (A) Analysis of the amino acid frequency in the three mutagenized resides (T60X, D67X and Q75X) for the all the bdSUMO mutants selected by phage display. (B) Sequence alignment of amino acids 56-79 of wild-type bdSUMO (bdSUMO$^{wt}$) and five different bdSUMO mutants that contain the most frequent mutations after selection by phage display (SEQ ID NOs: 9 and 20-24). Identical residues are highlighted in black boxes and the numbering of the sequence is according to the full-length wild type (wt) bdSUMO protein.
Figure 13:
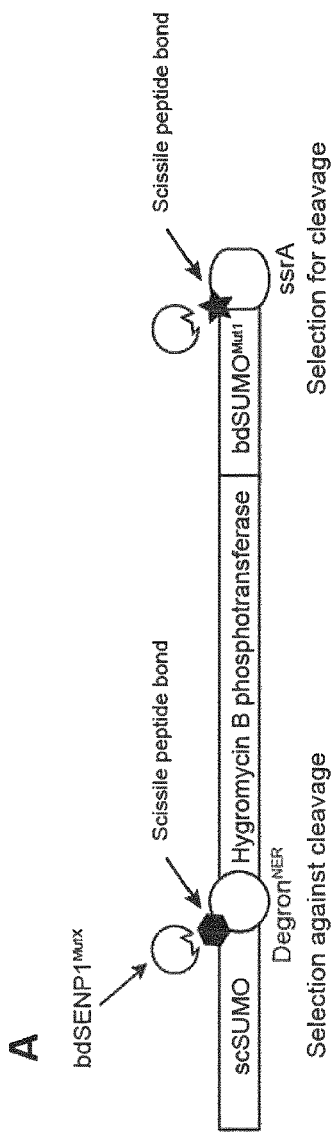
FIG. 13 (A) Selection construct used in E. coli for the selection of bdSENP1 mutants (bdSENP1$^{MutX}$) that cleavage preferentially bdSUMO$^{Mut\ 1}$ and not wild type scSUMO. (B) Sequence alignment of amino acids 265-354 of wild-type bdSENP1 (bdSENP$^{wt}$), bdSENP1$^{Mut\ B}$ and the six most abundant bdSENP1 mutants (SEQ ID NOs: 25, 27 and 32-40) after selection using the construct described in A. The numbering of the residues is according to the full-length protein (set forth in SEQ ID NO: 73) and the "-" denotes an amino acid deletion in the corresponding bdSENP1 mutant. Residues highlighted in black are strictly conserved within all mutants and the wild type (wt) bdSENP1 protease.
Figure 14:
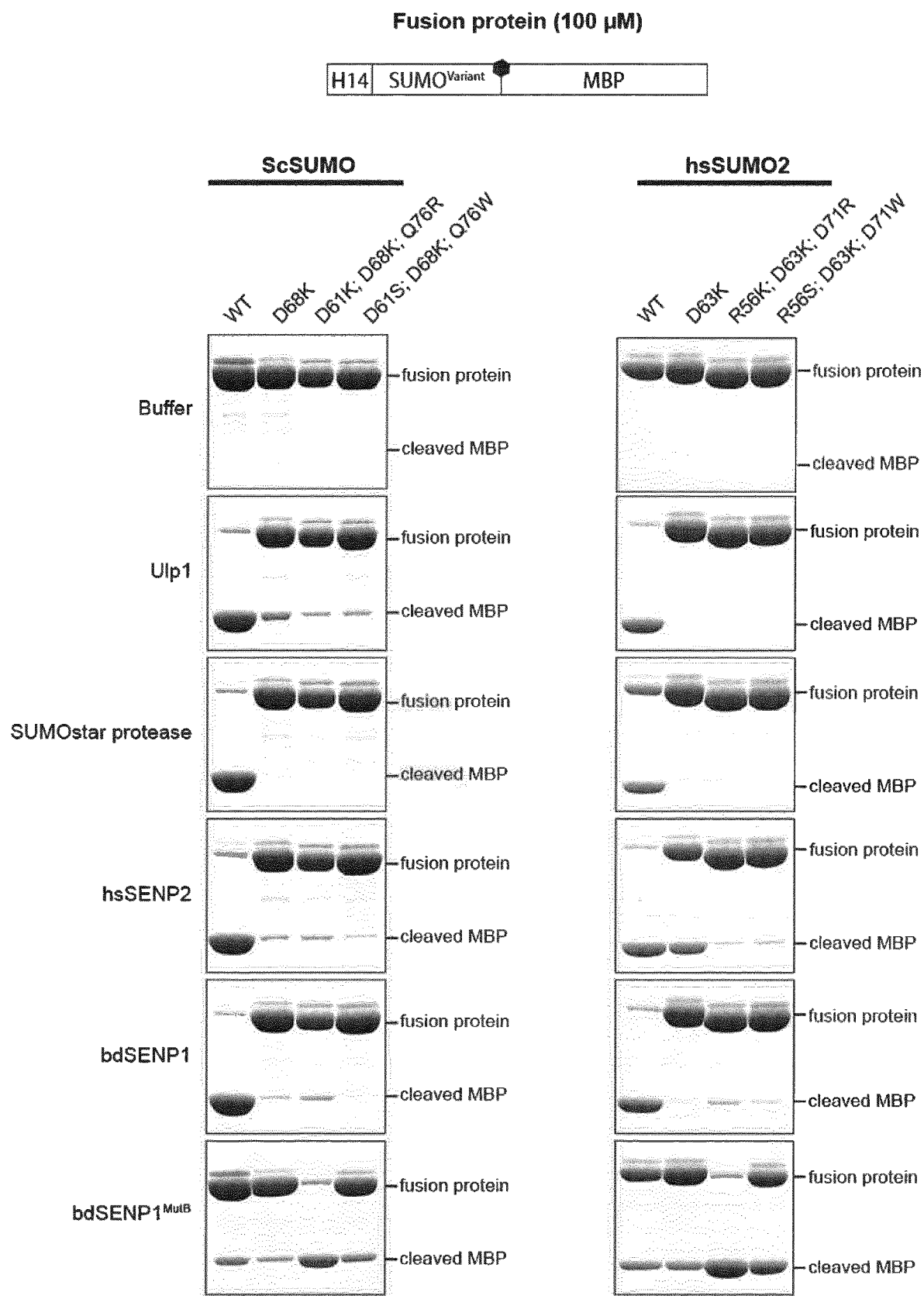
FIG. 14 Analogues mutations of the bdSUMO$^{Mut1}$ system can be used in wild type SUMO/SUMO proteases systems. scSUMO-MBP and hsSUMO2-MBP fusion proteins, containing mutations at the equivalent positions to the ones in the bdSUMO$^{Mut1}$ and bdSUMO$^{Mut11}$, were incubated for 1 h at 25° C. together with different SUMO-specific proteases. Numbering of the residues in scSUMO and hsSUMO2 is according to the full-length protein sequence. Samples were resolved by SDS-PAGE to separate the full-length fusion protein from the C-terminal cleaved MBP.

SUMO-specific proteases are the most efficient proteases for the removal of affinity tag from the protein of choice (Frey & Görlich 2014a; Malakhov et al. 2004). Unfortunately, this process can be only performed in vitro as the use of any exogenous SUMO-specific protease in vivo would compromise the viability of any eukaryotic cell. Since the site-specific proteolysis in vivo and specially using SUMO-specific proteases is of high relevance, we decided to test whether over-expression of bdSENP1$^{MutB}$ protease could be achieved without affecting the viability of yeast cells. Yeast cells were transformed with a high-copy vector encoding for Ulp1, bdSENP1, SUMOstar protease or bdSENP1$^{MutB}$ protease (FIG. 11). As a negative control, we transformed cells with a plasmid codifying for a bdSENP1 mutant (C440S) that is completely inactive, and therefore is not able to hydrolyze scSUMO. All transformed cells were able to grow when the expression of the proteases was repressed by the presence of glucose. After induction protease over-expression by the addition of galactose for 72 h at 30° C., only yeast cells expressing either bdSENP1$^{MutB}$ protease or bdSENP1 (C440S) grew to a very similar. In contrast, over-expression of Ulp1, bdSENP1 and SUMOstar protease led to complete cellular death in the presence of galactose. bdSENP1$^{MutB}$ protease is therefore the only SUMO-specific protease that could be use to perform site-directed proteolysis in living yeast cells.

Materials and Methods

*S. cerevisiae* cells strain SFY123 (MATa, ADE2, his3-11, 15 leu2-3, 112 LYS2, trp1-1, ura3, can1-100) were used to test their viability after over-expression of a SUMO-specific protease. First, cells were transformed with a galactose inducible expression plasmid using the protocol described in (Gietz & Schiestl 2007). Transformed cells were inoculated in SD-medium supplemented with 2% (w/v) of glucose and further inoculated for 16 h at 30° C. Cells were then pelleted and resuspended using fresh SD-medium supplemented with 2% (w/v) glucose and 2% (w/v) raffinose. Resuspended cells were incubated in of SD-medium containing 2% (w/v) of raffinose until exponential growth phase was reached ($OD_{600}$≈1.0). Next, cells were sequentially diluted in 10-fold steps and 5 μl of each dilution were spotted in plates containing either galactose (0.02% and 0.2%) or glucose (2%). Plates were incubated for 72 h at 30° C. and further scanned.

TABLE 1

Cleavage efficiency of different bdSUMO mutants by SUMO-specific proteases.

| Protease [A,B] | scSUMO wt | hsSUMO2 wt | bdSUMO mutants [C] | | | | | | | | | | |
|---|---|---|---|---|---|---|---|---|---|---|---|---|---|
| | | | wt | D67K | Mut1 | Mut8 | Mut10 | Mut11 | Mut12 | Mut13 | Mut14 | Mut15 |
| Ulp1 | ++++ | + | ++++ | resistant | resistant | resistant | resistant | resistant | resistant | resistant | resistant | resistant |
| SUMOstar protease | ++++ | + | ++++ | resistant | resistant | resistant | resistant | resistant | resistant | resistant | resistant | resistant |
| hsSENP2 | ++++ | ++++ | ++ | resistant | resistant | resistant | resistant | resistant | resistant | resistant | resistant | resistant |
| bdSENP1 | ++ | ++ | ++++ | + | + | + | + | + | + | ++ | + | + |
| bdSENP1$^{MutB}$ | resistant | resistant | + | +++ | ++++ | ++ | ++++ | ++++ | ++++ | ++++ | ++++ | ++++ |
| bdSENP1$^{MutG}$ | + | ++++ | ++ | +++ | ++++ | + | ++++ | +++ | ++ | +++ | ++ | +++ |
| bdSENP1$^{MutH}$ | resistant | resistant | + | +++ | ++++ | +++ | ++++ | ++++ | ++++ | ++++ | ++++ | ++++ |
| bdSENP1$^{Muti}$ | resistant | resistant | + | + | ++++ | + | ++ | ++ | ++ | +++ | ++ | ++ |
| bdSENP1$^{MutJ}$ | + | ++ | ++ | ++++ | ++++ | ++ | ++++ | ++++ | ++ | ++++ | ++ | ++++ |
| bdSENP1$^{MutK}$ | resistant | resistant | ++ | ++++ | ++++ | +++ | ++++ | ++++ | ++++ | ++++ | ++++ | ++++ |

Figure 15:
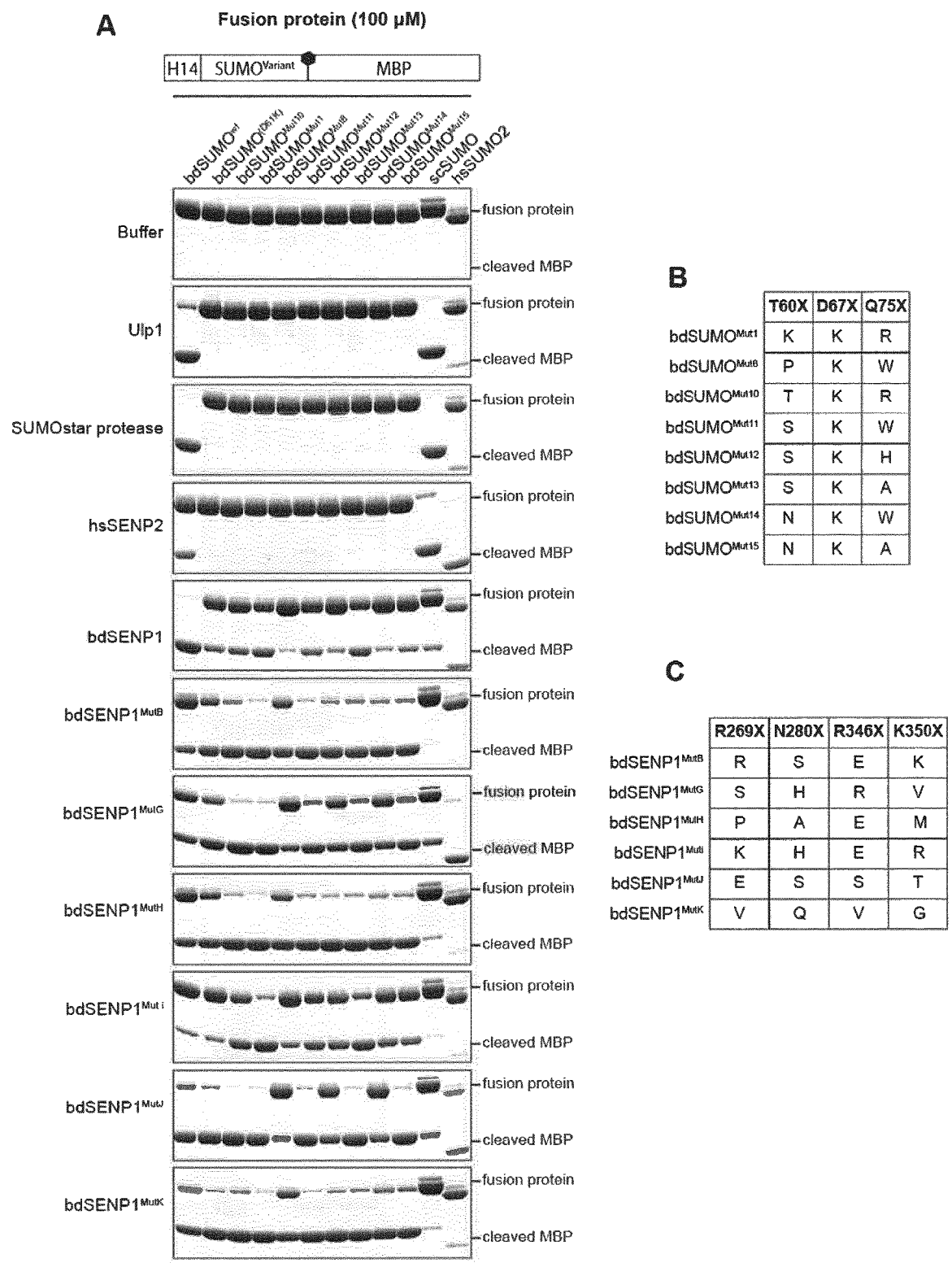
FIG. 15 Substrate specificity of different wild type and mutant SUMO-specific proteases. (A) Samples with 100 µM of MBP fused to a SUMO variant (wild type SUMO or different bdSUMO mutants) were incubated for 1 h at 25° C. with different SUMO-specific proteases. The protease concentration used in each assay is sufficient to completely cleave the cognate SUMO protein at the conditions mentioned above. Samples corresponding to around 2 µg of the SUMO fusion were analyzed by SDS-PAGE to separate the full-length fusion protein from the cleaved MBP. (B, C) List of the mutations in the bdSUMO and SENP1 variants tested in A, respectively

[A:] The protease concentration used for the reaction is sufficient to completely cleave 100 μM of the cognate SUMO protein within 1h at 25° C.
[B:] Mutations of the tested bdSENP1 variants are shown in FIG. 15
[C:] Mutations of the tested bdSUMO variants are shown in FIG. 15
+: ≤25% cleavage of the SUMO fusion protein
++: ≤50% cleavage of the SUMO fusion protein
+++: ≤75% cleavage of the SUMO fusion protein
++++: ~100% cleavage of the SUMO fusion protein

LIST OF REFERENCES

Amor-Mahjoub, M. et al., 2006. The effect of the hexahistidine-tag in the oligomerization of HSC70 constructs. *Journal of Chromatography B: Analytical Technologies in the Biomedical and Life Sciences*, 844 (2), pp. 328-334.

Bachmair, a, Finley, D. & Varshavsky, a, 1986. In vivo half-life of a protein is a function of its amino-terminal residue. *Science* (New York, N.Y.), 234 (4773), pp. 179-186.

BOHNSACK, M. T., 2004. Exportin 5 is a RanGTP-dependent dsRNA-binding protein that mediates nuclear export of pre-miRNAs. *RNA*, 10 (2), pp. 185-191.

Butt, T., Malakhova, O. & Malakhov, M., 2010. Methods and compositions for enhanced protein expression and purification. U.S. Pat. No. 7,655,413.

Butt, T. R. et al., 2005. SUMO fusion technology for difficult-to-express proteins. *Protein Expression and Purification*, 43 (1), pp. 1-9.

Chan, P. et al., 2011. Purification of Heterotrimeric G Protein Subunits by GST-Ric-8 Association: PRIMARY CHARACTERIZATION OF PURIFIED Golf. *Journal of Biological Chemistry*, 286 (4), pp. 2625-2635.

Chant, A. et al., 2005. Attachment of a histidine tag to the minimal zinc finger protein of the *Aspergillus nidulans* gene regulatory protein AreA causes a conformational change at the DNA-binding site. *Protein Expression and Purification*, 39 (2), pp. 152-159.

Chen, X., Pham, E. & Truong, K., 2010. TEV protease-facilitated stoichiometric delivery of multiple genes using a single expression vector. *Protein Science*, 19 (12), pp. 2379-2388.

Frey, S. & Görlich, D., 2014a. A new set of highly efficient, tag-cleaving proteases for purifying recombinant proteins. *Journal of Chromatography A*, 1337, pp. 95-105.

Frey, S. & Görlich, D., 2014b. Purification of protein complexes of defined subunit stoichiometry using a set of orthogonal, tag-cleaving proteases. *Journal of Chromatography A*, 1337, pp. 106-115.

Harder, B. et al., 2008. TEV protease-mediated cleavage in *Drosophila* as a tool to analyze protein functions in living organisms. *BioTechniques*, 44 (6), pp. 765-772.

Harper, S. & Speicher, D. W., 2011. Purification of Proteins Fused to Glutathione S-Transferase. In *Methods in molecular biology* (Clifton, N.J.). pp. 259-280.

Hendriks, I. A. & Vertegaal, A. C. O., 2016. A comprehensive compilation of SUMO proteomics. *Nature reviews. Molecular cell biology*, 17 (9), pp. 581-95.

Herrmann, J., Lerman, L. O. & Lerman, A., 2007. Ubiquitin and ubiquitin-like proteins in protein regulation. *Circulation Research*, 100 (9), pp. 1276-1291.

Himeno, H., Kurita, D. & Muto, A., 2014. TmRNA-mediated trans-translation as the major ribosome rescue system in a bacterial cell. *Frontiers in Genetics*, 5 (APR), pp. 1-13.

Katzmann, D. J., Babst, M. & Emr, S. D., 2001. Ubiquitin-dependent sorting into the multivesicular body pathway requires the function of a conserved endosomal protein sorting complex, ESCRT-I. *Cell*, 106 (2), pp. 145-155.

Keiler, K. C., 2008. Biology of trans-Translation. *Annual Review of Microbiology*, 62 (1), pp. 133-151.

Kerscher, O., Felberbaum, R. & Hochstrasser, M., 2006. Modification of proteins by ubiquitin and ubiquitin-like proteins. *Annual review of cell and developmental biology*, 22, pp. 159-80.

Khorasanizadeh, S., Peters, I. D. & Roder, H., 1996. Evidence for a three-state model of protein folding from kinetic analysis of ubiquitin variants with altered core residues. *Nature structural biology*, 3 (2), pp. 193-205.

Kimple, M. E., Brill, A. L. & Pasker, R. L., 2013. Overview of affinity tags for protein purification. *Current Protocols in Protein Science*, (SUPPL.73), pp. 608-616.

Kosobokova, E. N., Skrypnik, K. A. & Kosorukov, V. S., 2016. Overview of fusion tags for recombinant proteins. *Biochemistry* (Moscow), 81 (3), pp. 187-200.

Kostelansky, M. S. et al., 2007. Molecular Architecture and Functional Model of the Complete Yeast ESCRT-I Heterotetramer. *Cell*, 129 (3), pp. 485-498.

Kuwata, T. & Nakamura, T., 2008. BCL11A is a SUMOylated protein and recruits SUMO-conjugation enzymes in its nuclear body. *Genes to Cells*, 13 (9), pp. 931-940.

Malakhov, M. P. et al., 2004. SUMO fusions and SUMO-specific protease for efficient expression and purification of proteins. *Journal of Structural and Functional Genomics*, 5 (1-2), pp. 75-86.

Marblestone, J. G. et al., 2006. Comparison of SUMO fusion technology with traditional gene fusion systems: enhanced expression and solubility with SUMO. *Protein science: a publication of the Protein Society*, 15 (1), pp. 182-9.

McCoy, J. & La Ville, E., 1997. Expression and Purification of Thioredoxin Fusion Proteins. In *Current Protocols in Protein Science*. Hoboken, NJ, USA: John Wiley & Sons, Inc., p. 6.7.1-6.7.14.

Pattenden, L. K. & Thomas, W. G., 2008. Amylose Affinity Chromatography of Maltose-Binding Protein. In *Affinity Chromatography*. Totowa, NJ: Humana Press, pp. 169-190.

Rao, R. N., Allen, N. E. & Hobbs, J. N., 1983. Genetic and enzymatic basis of hygromycin B resistance in *Escherichia coli*. Genetic and Enzymatic Basis of Hygromycin B Resistance in *Escherichia coli*. *Antimicrobial Agents and Chemotherapy*, 24 (5), pp. 689-695.

Reverter, D. & Lima, C. D., 2004. A basis for SUMO protease specificity provided by analysis of human Senp2 and a Senp2-SUMO complex. *Structure*, 12 (8), pp. 1519-1531.

Reverter, D. & Lima, C. D., 2006. Structural basis for SENP2 protease interactions with SUMO precursors and conjugated substrates. *Nature Structural & Molecular Biology*, 13 (12), pp. 1060-1068.

Sato, M. & Toda, T., 2007. Alp7/TACC is a crucial target in Ran-GTPase-dependent spindle formation in fission yeast. *Nature*, 447 (7142), pp. 334-337.

Shen, L. et al., 2006. SUMO protease SENP1 induces isomerization of the scissile peptide bond. *Nature Structural & Molecular Biology*, 13 (12), pp. 1069-1077.

Suh-Lailam, B. B. & Hevel, J. M., 2009. Efficient cleavage of problematic tobacco etch virus (TEV)-protein arginine methyltransferase constructs. *Analytical Biochemistry*, 387 (1), pp. 130-132.

Taxis, C. & Knop, M., 2012. TIPI: TEV Protease-Mediated Induction of Protein Instability. In *Methods in Molecular Biology*. pp. 611-626.

Vertegaal, A. C. O. et al., 2004. A proteomic study of SUMO-2 target proteins. *Journal of Biological Chemistry*, 279 (32), pp. 33791-33798.

Wang, K. H. et al., 2008. Tuning the strength of a bacterial N-end rule degradation signal. *Journal of Biological Chemistry,* 283 (36), pp. 24600-24607.

Woestenenk, E. A. et al., 2004. His tag effect on solubility of human proteins produced in *Escherichia coli*: A comparison between four expression vectors. *Journal of Structural and Functional Genomics,* 5 (3), pp. 217-229.

Xu, Z. et al., 2006. Crystal structure of the SENP1 mutant C603S-SUMO complex reveals the hydrolytic mechanism of SUMO-specific protease. *The Biochemical journal,* 398 (3), pp. 345-352.

YAN, Y., ORCUTT, S. J. & STRICKLER, J. E., 2009. The use of SUMO as a fusion system for protein expression and purification. *Chimica oggi,* 27 (6).

Zuo, X., Li, S., et al., 2005. Enhanced expression and purification of membrane proteins by SUMO fusion in *Escherichia coli*. Journal of Structural and Functional Genomics, 6 (2-3), pp. 103-111.

Zuo, X., Mattern, M. R., et al., 2005. Expression and purification of SARS coronavirus proteins using SUMO-fusions. *Protein Expression and Purification,* 42 (1), pp. 100-110.

The invention claimed is:

1. A variant protease,
wherein said variant protease has at least 96% sequence identity over the full-length of the polypeptide of SEQ ID NO:6,
wherein said variant protease comprises an amino acid substitution at the position corresponding to position 33 of the protein of SEQ ID NO: 6, wherein the amino acid at said position is substituted by an amino acid selected from the group consisting of S, H, Q, A, G, and C, and
wherein said variant protease cleaves a first protease cleavage site (PCS) in a first fusion protein that comprises a maltose-binding protein (MBP) and said first PCS, wherein said first PCS is fused to the N-terminus of the MBP (first PCS-MBP fusion protein), wherein said first PCS has the amino acid sequence of SEQ ID NO: 41 and the MBP has the amino acid sequence of SEQ ID NO: 71, more efficiently after the C-terminal Gly-Gly motif of the first PCS of SEQ ID NO: 41 than said variant protease cleaves
(i) a second PCS in a second fusion protein that comprises a MBP and said second PCS, wherein said second PCS is fused to the N-terminus of the MBP (second PCS-MBP fusion protein), wherein said second PCS has the amino acid sequence of SEQ ID NO: 4 and the MBP has the amino acid sequence of SEQ ID NO: 71, wherein the cleavage occurs after the C-terminal Gly-Gly motif of the second PCS of SEQ ID NO: 4, or
(ii) a third PCS in a third fusion protein that comprises a MBP and said third PCS, wherein said third PCS is fused to the N-terminus of the MBP (third PCS-MBP fusion protein), wherein said third PCS has the amino acid sequence of SEQ ID NO: 3 and the MBP has the amino acid sequence of SEQ ID NO: 71, wherein the cleavage occurs after the C-terminal Gly-Gly motif of the third PCS of SEQ ID NO: 3,
when tested in a buffer under standard conditions of 1 hour incubation at 21° C., wherein said buffer comprises an initial concentration of the first, second and third PCS-MBP fusion proteins of 100 µM, and wherein the buffer comprises a pH of 7.5, Tris/HCl at a concentration of 45 mM, NaCl at a concentration of 250 mM, MgCl$_2$ at a concentration of 2 mM, sucrose at a concentration of 250 mM, and DTT at a concentration of 10 mM.

2. The variant protease of claim 1, wherein said variant protease cleaves the first PCS-MBP fusion protein at said standard conditions and at an at least 500-fold molar excess of said PCS-MBP fusion protein compared to the amount of said protease.

3. The variant protease of claim 1, wherein the amino acid at the position corresponding to position 33 of the protein of SEQ ID NO: 6 is selected from the group consisting of S, H, Q, and A.

4. The variant protease of claim 1, wherein said variant protease further comprises an amino acid substitution at the position corresponding to position 99 of the protein of SEQ ID NO: 6, wherein the amino acid at said position is substituted by another amino acid selected from the group consisting of E, S, V, Y, and L.

5. The variant protease of claim 4, wherein the amino acid at the position corresponding to position 99 of the protein of SEQ ID NO: 6 is substituted by an amino acid selected from the group consisting of E, S, and V.

6. The variant protease of claim 4, wherein said variant protease further comprises an amino acid substitution at the position corresponding to position 22 of the protein of SEQ ID NO: 6, wherein the amino acid at said position is substituted by another amino acid selected from the group consisting of E, S, P, K, and V.

7. The variant protease of claim 4, wherein said variant protease further comprises an amino acid substitution at the position corresponding to position 103 of the protein of SEQ ID NO: 6, wherein the amino acid at said position is substituted by another amino acid selected from the group consisting of M, E, V, G, T, and R.

8. The variant protease of claim 7 wherein the amino acid at the position corresponding to position 103 of the protein of SEQ ID NO: 6 is substituted by an amino acid selected from the group consisting of M, E, V, G and T.

9. The variant protease of claim 1, wherein said variant protease further comprises two or three amino acid substitutions at positions corresponding to positions of the protein of SEQ ID NO: 6 selected from the group consisting of positions 99, 22, and 103, wherein
the amino acid substitution at the position corresponding to position 99 of the protein of SEQ ID NO: 6 is a substitution by an amino acid selected from the group consisting of E, S, V, Y, and L,
the amino acid substitution at the position corresponding to position 22 of the protein of SEQ ID NO: 6 is a substitution by an amino acid selected from the group consisting of E, S, P, K, and V, and
the amino acid substitution at the position corresponding to position 103 of the protein of SEQ ID NO: 6 is a substitution by an amino acid selected from the group consisting of M, E, V, G, T, and R.

10. The variant protease of claim 1, wherein said variant protease comprises a combination of amino acid substitutions selected from the group consisting of
   (i) amino acid substitutions at the positions corresponding to positions 33 and 99 of the protein of SEQ ID NO: 6, wherein the amino acid at the position corresponding to position 33 of the protein of SEQ ID NO: 6 is S, and the amino acid at the position corresponding to position 99 of the protein of SEQ ID NO: 6 is E;
   (ii) amino acid substitutions at the positions corresponding to positions 22, 33 and 103 of the protein of SEQ ID NO: 6, wherein the amino acid at the position corresponding to position 33 of the protein of SEQ ID NO: 6 is H, the amino acid at the position corresponding to position 22 of the protein of SEQ ID NO: 6 is S, and the amino acid at the position corresponding to position 103 of the protein of SEQ ID NO: 6 is V;
   (iii) amino acid substitutions at the positions corresponding to positions 22, 33, 99 and 103 of the protein of SEQ ID NO: 6, wherein the amino acid at the position corresponding to position 22 of the protein of SEQ ID NO: 6 is P, the amino acid at the position corresponding to position 33 of the protein of SEQ ID NO: 6 is A, the amino acid at the position corresponding to position 99 of the protein of SEQ ID NO: 6 is E, and the amino acid at the position corresponding to position 103 of the protein of SEQ ID NO: 6 is M;
   (iv) amino acid substitutions at the positions corresponding to positions 22, 33, 99 and 103 of the protein of SEQ ID NO: 6, wherein the amino acid at the position corresponding to position 22 of the protein of SEQ ID NO: 6 is K, the amino acid at the position corresponding to position 33 of the protein of SEQ ID NO: 6 is H, the amino acid at the position corresponding to position 99 of the protein of SEQ ID NO: 6 is E, and the amino acid at the position corresponding to position 103 of the protein of SEQ ID NO: 6 is E;
   (v) amino acid substitutions at the positions corresponding to positions 22, 33, 99 and 103 of the protein of SEQ ID NO: 6, wherein the amino acid at the position corresponding to position 22 of the protein of SEQ ID NO: 6 is E, the amino acid at the position corresponding to position 33 of the protein of SEQ ID NO: 6 is S, the amino acid at the position corresponding to position 99 of the protein of SEQ ID NO: 6 is S, and the amino acid at the position corresponding to position 103 of the protein of SEQ ID NO: 6 is T; and
   (vi) amino acid substitutions at the positions corresponding to positions 22, 33, 99 and 103 of the protein of SEQ ID NO: 6, wherein the amino acid at the position corresponding to position 22 of the protein of SEQ ID NO: 6 is V, the amino acid at the position corresponding to position 33 of the protein of SEQ ID NO: 6 is Q, the amino acid at the position corresponding to position 99 of the protein of SEQ ID NO: 6 is V, and the amino acid at the position corresponding to position 103 of the protein of SEQ ID NO: 6 is G.

11. The variant protease of claim 1, wherein said variant protease comprises all of SEQ ID NO: 6, except for:
   (a) the amino acid substitution at the position corresponding to position 33 of the protein of SEQ ID NO: 6, or
   (b) the amino acid substitution at the position corresponding to position 33 of the protein of SEQ ID NO: 6 and one or more amino acid substitutions at positions corresponding to positions of the protein of SEQ ID NO: 6 selected from 22, 99, and 103.

12. The variant protease of claim 1 having the amino acid sequence of any one of SEQ ID NO: 56, 57, 58, 60, 61, 62, 63, 64, 65 or 66.

13. A process of purifying a protein of interest, comprising the steps of
   (i) providing a protein of interest to be purified, wherein said protein comprises an affinity tag fused to said protein via a protease cleavage site (PCS);
   (ii) binding the protein of step (i) to an affinity matrix via said affinity tag; and
   (iii) eluting the protein from the affinity matrix using the variant protein of claim 1, thereby purifying the protein.

14. The process of claim 13, wherein said PCS has at least 96% sequence identity over the full-length of the polypeptide of SEQ ID NO: 3,
   wherein said PCS comprises an amino acid substitution at the position corresponding to position 67 of the protein of SEQ ID NO: 3, wherein the amino acid at said position is substituted by another amino acid selected from the group consisting of K, R, N, A and H, and
   wherein said PCS comprises a C-terminal Gly-Gly motif.

15. The process of claim 14, wherein said PCS further comprises:
   (a) an amino acid substitution at the position corresponding to position 75 of the protein of SEQ ID NO: 3, wherein the amino acid at said position is substituted by another amino acid selected from the group consisting of R, W, A, H, M, I, P, and F; and/or
   (b) an amino acid substitution at the position corresponding to position 60 of the protein of SEQ ID NO: 3, wherein the amino acid at said position is substituted by another amino acid selected from the group consisting of S, N, K, P, HR, and Q.

16. The process of claim 14, wherein said PCS comprises a combination of amino acid substitutions selected from the group consisting of
   (i) amino acid substitutions at the positions corresponding to positions 67, 60 and 75 of the protein of SEQ ID NO: 3, wherein the amino acid at the position corresponding to position 67 of the protein of SEQ ID NO: 3 is K, the amino acid at the position corresponding to position 60 of the protein of SEQ ID NO: 3 is K, and the amino acid at the position corresponding to position 75 of the protein of SEQ ID NO: 3 is R;
   (ii) amino acid substitutions at the positions corresponding to positions 67, 60 and 75 of the protein of SEQ ID NO: 3, wherein the amino acid at the position corresponding to position 67 of the protein of SEQ ID NO: 3 is K, the amino acid at the position corresponding to position 60 of the protein of SEQ ID NO: 3 is P, and the amino acid at the position corresponding to position 75 of the protein of SEQ ID NO: 3 is W;
   (iii) amino acid substitutions at the positions corresponding to positions 67 and 75 of the protein of SEQ ID NO: 3, wherein the amino acid at the position corresponding to position 67 of the protein of SEQ ID NO: 3 is K, and the amino acid at the position corresponding to position 75 of the protein of SEQ ID NO: 3 is R;
   (iv) amino acid substitutions at the positions corresponding to positions 67, 60 and 75 of the protein of SEQ ID NO: 3, wherein the amino acid at the position corresponding to position 67 of the protein of SEQ ID NO: 3 is K, the amino acid at the position corresponding to position 60 of the protein of SEQ ID NO: 3 is S, and the amino acid at the position corresponding to position 75 of the protein of SEQ ID NO: 3 is H;

(v) amino acid substitutions at the positions corresponding to positions 67, 60 and 75 of the protein of SEQ ID NO: 3, wherein the amino acid at the position corresponding to position 67 of the protein of SEQ ID NO: 3 is K, the amino acid at the position corresponding to position 60 of the protein of SEQ ID NO: 3 is S, and the amino acid at the position corresponding to position 75 of the protein of SEQ ID NO: 3 is W;

(vi) amino acid substitutions at the positions corresponding to positions 67, 60 and 75 of the protein of SEQ ID NO: 3, wherein the amino acid at the position corresponding to position 67 of the protein of SEQ ID NO: 3 is K, the amino acid at the position corresponding to position 60 of the protein of SEQ ID NO: 3 is S, and the amino acid at the position corresponding to position 75 of the protein of SEQ ID NO: 3 is A;

(vii) amino acid substitutions at the positions corresponding to positions 67, 60 and 75 of the protein of SEQ ID NO: 3, wherein the amino acid at the position corresponding to position 67 of the protein of SEQ ID NO: 3 is K, the amino acid at the position corresponding to position 60 of the protein of SEQ ID NO: 3 is N, and the amino acid at the position corresponding to position 75 of the protein of SEQ ID NO: 3 is W; and (viii) amino acid substitutions at the positions corresponding to positions 67, 60 and 75 of the protein of SEQ ID NO: 3, wherein the amino acid at the position corresponding to position 67 of the protein of SEQ ID NO: 3 is K, the amino acid at the position corresponding to position 60 of the protein of SEQ ID NO: 3 is N, and the amino acid at the position corresponding to position 75 of the protein of SEQ ID NO: 3 is A.

17. The process of claim 13, wherein said PCS has the amino acid sequence of SEQ ID NO: 3 except for an amino acid substitution at the position corresponding to position 67 of the protein of SEQ ID NO: 3, wherein the amino acid at said position is K.

18. The process of claim 13, wherein said PCS has the amino acid sequence of SEQ ID NO: 3 except for
   (a) an amino acid substitution at the position corresponding to position 67 of the protein of SEQ ID NO: 3, wherein the amino acid at said position is K, and an amino acid substitution at the position corresponding to position 60 of the protein of SEQ ID NO: 3;
   (b) an amino acid substitution at the position corresponding to position 67 of the protein of SEQ ID NO: 3, wherein the amino acid at said position is K, and an amino acid substitution at the position corresponding to position 75 of the protein of SEQ ID NO: 3; or
   (c) an amino acid substitution at the position corresponding to position 67 of the protein of SEQ ID NO: 3, wherein the amino acid at said position is K, and additional amino acid substitutions at positions corresponding to positions 60 and 75 of the protein of SEQ ID NO: 3.

19. The process of claim 13, wherein said PCS has an amino acid sequence selected from the group consisting of SEQ ID NO: 41, 42, 43, 44, 45, 46, 47, 48, 49, 50, 51, 52, 53, 54 and 55.

* * * * *

SEQUENCE LISTING

```
<160> NUMBER OF SEQ ID NOS: 73

<210> SEQ ID NO 1
<211> LENGTH: 5
<212> TYPE: PRT
<213> ORGANISM: Artificial
<220> FEATURE:
<223> OTHER INFORMATION: DegronNER

<400> SEQUENCE: 1

Phe Leu Phe Val Gln
1               5

<210> SEQ ID NO 2
<211> LENGTH: 10
<212> TYPE: PRT
<213> ORGANISM: Artificial
<220> FEATURE:
<223> OTHER INFORMATION: ssrA

<400> SEQUENCE: 2

Ala Ala Asp Glu Asn Tyr Ala Leu Ala Ala
1               5                   10

<210> SEQ ID NO 3
<211> LENGTH: 97
<212> TYPE: PRT
<213> ORGANISM: Artificial
<220> FEATURE:
<223> OTHER INFORMATION: Wt bdSUMO

<400> SEQUENCE: 3

Met Ser Ala Ala Gly Gly Glu Glu Asp Lys Lys Pro Ala Gly Gly Glu
1               5                   10                  15

Gly Gly Gly Ala His Ile Asn Leu Lys Val Lys Gly Gln Asp Gly Asn
            20                  25                  30

Glu Val Phe Phe Arg Ile Lys Arg Ser Thr Gln Leu Lys Lys Leu Met
        35                  40                  45

Asn Ala Tyr Cys Asp Arg Gln Ser Val Asp Met Thr Ala Ile Ala Phe
    50                  55                  60

Leu Phe Asp Gly Arg Arg Leu Arg Ala Glu Gln Thr Pro Asp Glu Leu
65                  70                  75                  80

Glu Met Glu Asp Gly Asp Glu Ile Asp Ala Met Leu His Gln Thr Gly
                85                  90                  95

Gly

<210> SEQ ID NO 4
<211> LENGTH: 98
<212> TYPE: PRT
<213> ORGANISM: Artificial
<220> FEATURE:
```

<223> OTHER INFORMATION: scSUMO/Smt3p

<400> SEQUENCE: 4

```
Met Ser Asp Ser Glu Val Asn Gln Glu Ala Lys Pro Glu Val Lys Pro
1               5                   10                  15

Glu Val Lys Pro Glu Thr His Ile Asn Leu Lys Val Ser Asp Gly Ser
            20                  25                  30

Ser Glu Ile Phe Phe Lys Ile Lys Thr Thr Pro Leu Arg Arg Leu
        35                  40                  45

Met Glu Ala Phe Ala Lys Arg Gln Gly Lys Glu Met Asp Ser Leu Arg
    50                  55                  60

Phe Leu Tyr Asp Gly Ile Arg Ile Gln Ala Asp Gln Thr Pro Glu Asp
65                  70                  75                  80

Leu Asp Met Glu Asp Asn Asp Ile Ile Glu Ala His Arg Glu Gln Ile
                85                  90                  95

Gly Gly
```

<210> SEQ ID NO 5
<211> LENGTH: 93
<212> TYPE: PRT
<213> ORGANISM: Artificial
<220> FEATURE:
<223> OTHER INFORMATION: hsSUMO2

<400> SEQUENCE: 5

```
Met Ala Asp Glu Lys Pro Lys Glu Gly Val Lys Thr Glu Asn Asn Asp
1               5                   10                  15

His Ile Asn Leu Lys Val Ala Gly Gln Asp Gly Ser Val Val Gln Phe
            20                  25                  30

Lys Ile Lys Arg His Thr Pro Leu Ser Lys Leu Met Lys Ala Tyr Cys
        35                  40                  45

Glu Arg Gln Gly Leu Ser Met Arg Gln Ile Arg Phe Arg Phe Asp Gly
    50                  55                  60

Gln Pro Ile Asn Glu Thr Asp Thr Pro Ala Gln Leu Glu Met Glu Asp
65                  70                  75                  80

Glu Asp Thr Ile Asp Val Phe Gln Gln Gln Thr Gly Gly
                85                  90
```

<210> SEQ ID NO 6
<211> LENGTH: 234
<212> TYPE: PRT
<213> ORGANISM: Artificial
<220> FEATURE:
<223> OTHER INFORMATION: bdSENP1

<400> SEQUENCE: 6

```
Pro Phe Val Pro Leu Thr Asp Glu Asp Glu Asp Asn Val Arg His Ala
1               5                   10                  15

Leu Gly Gly Arg Lys Arg Ser Glu Thr Leu Ser Val His Glu Ala Ser
            20                  25                  30

Asn Ile Val Ile Thr Arg Glu Ile Leu Gln Cys Leu Asn Asp Lys Glu
        35                  40                  45

Trp Leu Asn Asp Glu Val Ile Asn Leu Tyr Leu Glu Leu Leu Lys Glu
    50                  55                  60

Arg Glu Leu Arg Glu Pro Asn Lys Phe Leu Lys Cys His Phe Phe Asn
65                  70                  75                  80

Thr Phe Phe Tyr Lys Lys Leu Ile Asn Gly Gly Tyr Asp Tyr Lys Ser
                85                  90                  95
```

```
Val Arg Arg Trp Thr Thr Lys Arg Lys Leu Gly Tyr Asn Leu Ile Asp
            100                 105                 110

Cys Asp Lys Ile Phe Val Pro Ile His Lys Asp Val His Trp Cys Leu
            115                 120                 125

Ala Val Ile Asn Ile Lys Glu Lys Lys Phe Gln Tyr Leu Asp Ser Leu
            130                 135                 140

Gly Tyr Met Asp Met Lys Ala Leu Arg Ile Leu Ala Lys Tyr Leu Val
145                 150                 155                 160

Asp Glu Val Lys Asp Lys Ser Gly Lys Gln Ile Asp Val His Ala Trp
                165                 170                 175

Lys Gln Glu Gly Val Gln Asn Leu Pro Leu Gln Glu Asn Gly Trp Asp
            180                 185                 190

Cys Gly Met Phe Met Leu Lys Tyr Ile Asp Phe Tyr Ser Arg Asp Met
            195                 200                 205

Glu Leu Val Phe Gly Gln Lys His Met Ser Tyr Phe Arg Arg Arg Thr
210                 215                 220

Ala Lys Glu Ile Leu Asp Leu Lys Ala Gly
225                 230

<210> SEQ ID NO 7
<211> LENGTH: 219
<212> TYPE: PRT
<213> ORGANISM: Artificial
<220> FEATURE:
<223> OTHER INFORMATION: scUlp1

<400> SEQUENCE: 7

Leu Val Pro Glu Leu Asn Glu Lys Asp Asp Gln Val Gln Lys Ala
1               5                   10                  15

Leu Ala Ser Arg Glu Asn Thr Gln Leu Met Asn Arg Asp Asn Ile Glu
            20                  25                  30

Ile Thr Val Arg Asp Phe Lys Thr Leu Ala Pro Arg Arg Trp Leu Asn
            35                  40                  45

Asp Thr Ile Ile Glu Phe Phe Met Lys Tyr Ile Glu Lys Ser Thr Pro
50                  55                  60

Asn Thr Val Ala Phe Asn Ser Phe Phe Tyr Thr Asn Leu Ser Glu Arg
65                  70                  75                  80

Gly Tyr Gln Gly Val Arg Arg Trp Met Lys Arg Lys Lys Thr Gln Ile
                85                  90                  95

Asp Lys Leu Asp Lys Ile Phe Thr Pro Ile Asn Leu Asn Gln Ser His
            100                 105                 110

Trp Ala Leu Gly Ile Ile Asp Leu Lys Lys Lys Thr Ile Gly Tyr Val
            115                 120                 125

Asp Ser Leu Ser Asn Gly Pro Asn Ala Met Ser Phe Ala Ile Leu Thr
            130                 135                 140

Asp Leu Gln Lys Tyr Val Met Glu Glu Ser Lys His Thr Ile Gly Glu
145                 150                 155                 160

Asp Phe Asp Leu Ile His Leu Asp Cys Pro Gln Gln Pro Asn Gly Tyr
                165                 170                 175

Asp Cys Gly Ile Tyr Val Cys Met Asn Thr Leu Tyr Gly Ser Ala Asp
            180                 185                 190

Ala Pro Leu Asp Phe Asp Tyr Lys Asp Ala Ile Arg Met Arg Arg Phe
            195                 200                 205

Ile Ala His Leu Ile Leu Thr Asp Ala Leu Lys
            210                 215
```

<210> SEQ ID NO 8
<211> LENGTH: 226
<212> TYPE: PRT
<213> ORGANISM: Artificial
<220> FEATURE:
<223> OTHER INFORMATION: hsSENP2

<400> SEQUENCE: 8

```
Glu Phe Pro Glu Ile Thr Glu Met Glu Lys Glu Ile Lys Asn Val
1               5                   10                  15

Phe Arg Asn Gly Asn Gln Asp Glu Val Leu Ser Glu Ala Phe Arg Leu
            20                  25                  30

Thr Ile Thr Arg Lys Asp Ile Gln Thr Leu Asn His Leu Asn Trp Leu
        35                  40                  45

Asn Asp Glu Ile Ile Asn Phe Tyr Met Asn Met Leu Met Glu Arg Ser
    50                  55                  60

Lys Glu Lys Gly Leu Pro Ser Val His Ala Phe Asn Thr Phe Phe
65                  70                  75                  80

Thr Lys Leu Lys Thr Ala Gly Tyr Gln Ala Val Lys Arg Trp Thr Lys
                85                  90                  95

Lys Val Asp Val Phe Ser Val Asp Ile Leu Leu Val Pro Ile His Leu
            100                 105                 110

Gly Val His Trp Cys Leu Ala Val Val Asp Phe Arg Lys Lys Asn Ile
        115                 120                 125

Thr Tyr Tyr Asp Ser Met Gly Gly Ile Asn Asn Glu Ala Cys Arg Ile
    130                 135                 140

Leu Leu Gln Tyr Leu Lys Gln Glu Ser Ile Asp Lys Lys Arg Lys Glu
145                 150                 155                 160

Phe Asp Thr Asn Gly Trp Gln Leu Phe Ser Lys Lys Ser Gln Glu Ile
                165                 170                 175

Pro Gln Gln Met Asn Gly Ser Asp Cys Gly Met Phe Ala Cys Lys Tyr
            180                 185                 190

Ala Asp Cys Ile Thr Lys Asp Arg Pro Ile Asn Phe Thr Gln Gln His
        195                 200                 205

Met Pro Tyr Phe Arg Lys Arg Met Val Trp Glu Ile Leu His Arg Lys
    210                 215                 220

Leu Leu
225
```

<210> SEQ ID NO 9
<211> LENGTH: 24
<212> TYPE: PRT
<213> ORGANISM: Artificial
<220> FEATURE:
<223> OTHER INFORMATION: Wt bdSUMO; amino acids 56-79

<400> SEQUENCE: 9

```
Ser Val Asp Met Thr Ala Ile Ala Phe Leu Phe Asp Gly Arg Arg Leu
1               5                   10                  15

Arg Ala Glu Gln Thr Pro Asp Glu
            20
```

<210> SEQ ID NO 10
<211> LENGTH: 24
<212> TYPE: PRT
<213> ORGANISM: Artificial
<220> FEATURE:
<223> OTHER INFORMATION: Mut1 bdSUMO

```
<400> SEQUENCE: 10

Ser Val Asp Met Lys Ala Ile Ala Phe Leu Phe Lys Gly Arg Arg Leu
1               5                   10                  15

Arg Ala Glu Arg Thr Pro Asp Glu
            20

<210> SEQ ID NO 11
<211> LENGTH: 24
<212> TYPE: PRT
<213> ORGANISM: Artificial
<220> FEATURE:
<223> OTHER INFORMATION: Mut2 bdSUMO

<400> SEQUENCE: 11

Ser Val Asp Met Thr Ala Ile Ala Phe Leu Phe Lys Gly Arg Arg Leu
1               5                   10                  15

Arg Ala Glu Cys Thr Pro Asp Glu
            20

<210> SEQ ID NO 12
<211> LENGTH: 24
<212> TYPE: PRT
<213> ORGANISM: Artificial
<220> FEATURE:
<223> OTHER INFORMATION: Mut3 bdSUMO

<400> SEQUENCE: 12

Ser Val Asp Met His Ala Ile Ala Phe Leu Phe Lys Gly Arg Arg Leu
1               5                   10                  15

Arg Ala Glu Lys Thr Pro Asp Glu
            20

<210> SEQ ID NO 13
<211> LENGTH: 24
<212> TYPE: PRT
<213> ORGANISM: Artificial
<220> FEATURE:
<223> OTHER INFORMATION: Mut4 bdSUMO

<400> SEQUENCE: 13

Ser Val Asp Met Arg Ala Ile Ala Phe Leu Phe Arg Gly Arg Arg Leu
1               5                   10                  15

Arg Ala Glu Val Thr Pro Asp Glu
            20

<210> SEQ ID NO 14
<211> LENGTH: 24
<212> TYPE: PRT
<213> ORGANISM: Artificial
<220> FEATURE:
<223> OTHER INFORMATION: Mut5 bdSUMO

<400> SEQUENCE: 14

Ser Val Asp Met Thr Ala Ile Ala Phe Leu Phe Lys Gly Arg Arg Leu
1               5                   10                  15

Arg Ala Glu Phe Thr Pro Asp Glu
            20

<210> SEQ ID NO 15
<211> LENGTH: 24
<212> TYPE: PRT
<213> ORGANISM: Artificial
<220> FEATURE:
```

```
<223> OTHER INFORMATION: Mut6 bdSUMO

<400> SEQUENCE: 15

Ser Val Asp Met His Ala Ile Ala Phe Leu Phe Lys Gly Arg Arg Leu
1               5                   10                  15

Arg Ala Glu Gln Thr Pro Asp Glu
            20

<210> SEQ ID NO 16
<211> LENGTH: 24
<212> TYPE: PRT
<213> ORGANISM: Artificial
<220> FEATURE:
<223> OTHER INFORMATION: Mut7 bdSUMO

<400> SEQUENCE: 16

Ser Val Asp Met Asp Ala Ile Ala Phe Leu Phe Arg Gly Arg Arg Leu
1               5                   10                  15

Arg Ala Glu Cys Thr Pro Asp Glu
            20

<210> SEQ ID NO 17
<211> LENGTH: 24
<212> TYPE: PRT
<213> ORGANISM: Artificial
<220> FEATURE:
<223> OTHER INFORMATION: Mut8 bdSUMO

<400> SEQUENCE: 17

Ser Val Asp Met Pro Ala Ile Ala Phe Leu Phe Lys Gly Arg Arg Leu
1               5                   10                  15

Arg Ala Glu Trp Thr Pro Asp Glu
            20

<210> SEQ ID NO 18
<211> LENGTH: 24
<212> TYPE: PRT
<213> ORGANISM: Artificial
<220> FEATURE:
<223> OTHER INFORMATION: Mut9 bdSUMO

<400> SEQUENCE: 18

Ser Val Asp Met Ala Ala Ile Ala Phe Leu Phe Lys Gly Arg Arg Leu
1               5                   10                  15

Arg Ala Glu Tyr Thr Pro Asp Glu
            20

<210> SEQ ID NO 19
<211> LENGTH: 24
<212> TYPE: PRT
<213> ORGANISM: Artificial
<220> FEATURE:
<223> OTHER INFORMATION: Mut10 bdSUMO

<400> SEQUENCE: 19

Ser Val Asp Met Thr Ala Ile Ala Phe Leu Phe Lys Gly Arg Arg Leu
1               5                   10                  15

Arg Ala Glu Arg Thr Pro Asp Glu
            20

<210> SEQ ID NO 20
<211> LENGTH: 24
<212> TYPE: PRT
<213> ORGANISM: Artificial
```

<220> FEATURE:
<223> OTHER INFORMATION: Mut11 bdSUMO

<400> SEQUENCE: 20

Ser Val Asp Met Ser Ala Ile Ala Phe Leu Phe Lys Gly Arg Arg Leu
1               5                   10                  15

Arg Ala Glu Trp Thr Pro Asp Glu
            20

<210> SEQ ID NO 21
<211> LENGTH: 24
<212> TYPE: PRT
<213> ORGANISM: Artificial
<220> FEATURE:
<223> OTHER INFORMATION: Mut12 bdSUMO

<400> SEQUENCE: 21

Ser Val Asp Met Ser Ala Ile Ala Phe Leu Phe Lys Gly Arg Arg Leu
1               5                   10                  15

Arg Ala Glu His Thr Pro Asp Glu
            20

<210> SEQ ID NO 22
<211> LENGTH: 24
<212> TYPE: PRT
<213> ORGANISM: Artificial
<220> FEATURE:
<223> OTHER INFORMATION: Mut13 bdSUMO

<400> SEQUENCE: 22

Ser Val Asp Met Ser Ala Ile Ala Phe Leu Phe Lys Gly Arg Arg Leu
1               5                   10                  15

Arg Ala Glu Ala Thr Pro Asp Glu
            20

<210> SEQ ID NO 23
<211> LENGTH: 24
<212> TYPE: PRT
<213> ORGANISM: Artificial
<220> FEATURE:
<223> OTHER INFORMATION: Mut14 bdSUMO

<400> SEQUENCE: 23

Ser Val Asp Met Asn Ala Ile Ala Phe Leu Phe Lys Gly Arg Arg Leu
1               5                   10                  15

Arg Ala Glu Trp Thr Pro Asp Glu
            20

<210> SEQ ID NO 24
<211> LENGTH: 24
<212> TYPE: PRT
<213> ORGANISM: Artificial
<220> FEATURE:
<223> OTHER INFORMATION: Mut15 bdSUMO

<400> SEQUENCE: 24

Ser Val Asp Met Asn Ala Ile Ala Phe Leu Phe Lys Gly Arg Arg Leu
1               5                   10                  15

Arg Ala Glu Ala Thr Pro Asp Glu
            20

<210> SEQ ID NO 25
<211> LENGTH: 90
<212> TYPE: PRT

<213> ORGANISM: Artificial
<220> FEATURE:
<223> OTHER INFORMATION: Wt bdSENP1

<400> SEQUENCE: 25

```
Gly Gly Arg Lys Arg Ser Glu Thr Leu Ser Val His Glu Ala Ser Asn
1               5                   10                  15

Ile Val Ile Thr Arg Glu Ile Leu Gln Cys Leu Asn Asp Lys Glu Trp
                20                  25                  30

Leu Asn Asp Glu Val Ile Asn Leu Tyr Leu Glu Leu Leu Lys Glu Arg
            35                  40                  45

Glu Leu Arg Glu Pro Asn Lys Phe Leu Lys Cys His Phe Phe Asn Thr
    50                  55                  60

Phe Phe Tyr Lys Lys Leu Ile Asn Gly Gly Tyr Asp Tyr Lys Ser Val
65                  70                  75                  80

Arg Arg Trp Thr Thr Lys Arg Lys Leu Gly
                85                  90
```

<210> SEQ ID NO 26
<211> LENGTH: 90
<212> TYPE: PRT
<213> ORGANISM: Artificial
<220> FEATURE:
<223> OTHER INFORMATION: MutA bdSENP1

<400> SEQUENCE: 26

```
Gly Gly Arg Lys Pro Ser Glu Thr Leu Ser Val His Glu Ala Ser Gly
1               5                   10                  15

Ile Val Ile Thr Arg Glu Ile Leu Gln Cys Leu Asn Asp Lys Glu Trp
                20                  25                  30

Leu Asn Asp Glu Val Ile Asn Leu Tyr Leu Glu Leu Leu Lys Glu Arg
            35                  40                  45

Glu Leu Arg Glu Pro Asn Lys Phe Leu Lys Cys His Phe Phe Asn Thr
    50                  55                  60

Phe Phe Tyr Lys Lys Leu Ile Asn Gly Gly Tyr Asp Tyr Lys Ser Val
65                  70                  75                  80

Arg Glu Trp Thr Thr Pro Arg Lys Leu Gly
                85                  90
```

<210> SEQ ID NO 27
<211> LENGTH: 90
<212> TYPE: PRT
<213> ORGANISM: Artificial
<220> FEATURE:
<223> OTHER INFORMATION: MutB bdSENP1

<400> SEQUENCE: 27

```
Gly Gly Arg Lys Arg Ser Glu Thr Leu Ser Val His Glu Ala Ser Ser
1               5                   10                  15

Ile Val Ile Thr Arg Glu Ile Leu Gln Cys Leu Asn Asp Lys Glu Trp
                20                  25                  30

Leu Asn Asp Glu Val Ile Asn Leu Tyr Leu Glu Leu Leu Lys Glu Arg
            35                  40                  45

Glu Leu Arg Glu Pro Asn Lys Phe Leu Lys Cys His Phe Phe Asn Thr
    50                  55                  60

Phe Phe Tyr Lys Lys Leu Ile Asn Gly Gly Tyr Asp Tyr Lys Ser Val
65                  70                  75                  80

Arg Glu Trp Thr Thr Lys Arg Lys Leu Gly
                85                  90
```

<210> SEQ ID NO 28
<211> LENGTH: 90
<212> TYPE: PRT
<213> ORGANISM: Artificial
<220> FEATURE:
<223> OTHER INFORMATION: MutC bdSENP1

<400> SEQUENCE: 28

Gly Gly Arg Lys Ser Ser Glu Thr Leu Ser Val His Glu Ala Ser Ala
1               5                   10                  15

Ile Val Ile Thr Arg Glu Ile Leu Gln Cys Leu Asn Asp Lys Glu Trp
            20                  25                  30

Leu Asn Asp Glu Val Ile Asn Leu Tyr Leu Glu Leu Leu Lys Glu Arg
        35                  40                  45

Glu Leu Arg Glu Pro Asn Lys Phe Leu Lys Cys His Phe Phe Asn Thr
    50                  55                  60

Phe Phe Tyr Lys Lys Leu Ile Asn Gly Gly Tyr Asp Tyr Lys Ser Val
65                  70                  75                  80

Arg Gly Trp Thr Thr Val Arg Lys Leu Gly
                85                  90

<210> SEQ ID NO 29
<211> LENGTH: 90
<212> TYPE: PRT
<213> ORGANISM: Artificial
<220> FEATURE:
<223> OTHER INFORMATION: MutD bdSENP1

<400> SEQUENCE: 29

Gly Gly Arg Lys Pro Ser Glu Thr Leu Ser Val His Glu Ala Ser Glu
1               5                   10                  15

Ile Val Ile Thr Arg Glu Ile Leu Gln Cys Leu Asn Asp Lys Glu Trp
            20                  25                  30

Leu Asn Asp Glu Val Ile Asn Leu Tyr Leu Glu Leu Leu Lys Glu Arg
        35                  40                  45

Glu Leu Arg Glu Pro Asn Lys Phe Leu Lys Cys His Phe Phe Asn Thr
    50                  55                  60

Phe Phe Tyr Lys Lys Leu Ile Asn Gly Gly Tyr Asp Tyr Lys Ser Val
65                  70                  75                  80

Arg Glu Trp Thr Thr Gln Arg Lys Leu Gly
                85                  90

<210> SEQ ID NO 30
<211> LENGTH: 90
<212> TYPE: PRT
<213> ORGANISM: Artificial
<220> FEATURE:
<223> OTHER INFORMATION: MutE bdSENP1

<400> SEQUENCE: 30

Gly Gly Arg Lys Arg Ser Glu Thr Leu Ser Val His Glu Ala Ser Gly
1               5                   10                  15

Ile Val Ile Thr Arg Glu Ile Leu Gln Cys Leu Asn Asp Lys Glu Trp
            20                  25                  30

Leu Asn Asp Glu Val Ile Asn Leu Tyr Leu Glu Leu Leu Lys Glu Arg
        35                  40                  45

Glu Leu Arg Glu Pro Asn Lys Phe Leu Lys Cys His Phe Phe Asn Thr
    50                  55                  60

Phe Phe Tyr Lys Lys Leu Ile Asn Gly Gly Tyr Asp Tyr Lys Ser Val
65                  70                  75                  80

Arg Tyr Trp Thr Thr Ala Arg Lys Leu Gly
                85                  90

<210> SEQ ID NO 31
<211> LENGTH: 90
<212> TYPE: PRT
<213> ORGANISM: Artificial
<220> FEATURE:
<223> OTHER INFORMATION: MutF bdSENP1

<400> SEQUENCE: 31

Gly Gly Arg Lys Pro Ser Glu Thr Leu Ser Val His Glu Ala Ser Cys
1               5                   10                  15

Ile Val Ile Thr Arg Glu Ile Leu Gln Cys Leu Asn Asp Lys Glu Trp
                20                  25                  30

Leu Asn Asp Glu Val Ile Asn Leu Tyr Leu Glu Leu Leu Lys Glu Arg
            35                  40                  45

Glu Leu Arg Glu Pro Asn Lys Phe Leu Lys Cys His Phe Phe Asn Thr
        50                  55                  60

Phe Phe Tyr Lys Lys Leu Ile Asn Gly Gly Tyr Asp Tyr Lys Ser Val
65                  70                  75                  80

Arg Leu Trp Thr Thr Arg Arg Lys Leu Gly
                85                  90

<210> SEQ ID NO 32
<211> LENGTH: 89
<212> TYPE: PRT
<213> ORGANISM: Artificial
<220> FEATURE:
<223> OTHER INFORMATION: MutG bdSENP1

<400> SEQUENCE: 32

Gly Gly Arg Lys Ser Ser Glu Thr Leu Ser Val His Glu Ala Ser His
1               5                   10                  15

Ile Val Ile Thr Arg Glu Ile Leu Gln Cys Leu Asn Asp Lys Glu Trp
                20                  25                  30

Leu Asn Asp Glu Val Ile Asn Leu Tyr Leu Glu Leu Leu Lys Glu Arg
            35                  40                  45

Glu Leu Arg Glu Pro Asn Lys Phe Leu Lys Cys His Phe Phe Asn Thr
        50                  55                  60

Phe Phe Tyr Lys Lys Leu Ile Asn Gly Gly Tyr Asp Tyr Lys Ser Val
65                  70                  75                  80

Arg Arg Trp Thr Thr Val Lys Leu Gly
                85

<210> SEQ ID NO 33
<211> LENGTH: 89
<212> TYPE: PRT
<213> ORGANISM: Artificial
<220> FEATURE:
<223> OTHER INFORMATION: MutH bdSENP1

<400> SEQUENCE: 33

Gly Gly Arg Lys Pro Ser Glu Thr Leu Ser Val His Glu Ala Ser Ala
1               5                   10                  15

Ile Val Ile Thr Arg Glu Ile Leu Gln Cys Leu Asn Asp Lys Glu Trp
                20                  25                  30

Leu Asn Asp Glu Val Ile Asn Leu Tyr Leu Glu Leu Leu Lys Glu Arg

```
                35                  40                  45
Glu Leu Arg Glu Pro Asn Lys Phe Leu Lys Cys His Phe Phe Asn Thr
         50                  55                  60
Phe Phe Tyr Lys Lys Leu Ile Asn Gly Tyr Asp Tyr Lys Ser Val Arg
 65                  70                  75                  80
Glu Trp Thr Thr Met Arg Lys Leu Gly
                 85
```

<210> SEQ ID NO 34
<211> LENGTH: 90
<212> TYPE: PRT
<213> ORGANISM: Artificial
<220> FEATURE:
<223> OTHER INFORMATION: MutI bdSENP1

<400> SEQUENCE: 34

```
Gly Gly Arg Lys Lys Ser Glu Thr Leu Ser Val His Glu Ala Ser His
 1               5                  10                  15
Ile Val Ile Thr Arg Glu Ile Leu Gln Cys Leu Asn Asp Lys Glu Trp
                20                  25                  30
Leu Asn Asp Glu Val Ile Asn Leu Tyr Leu Glu Leu Leu Lys Glu Arg
         35                  40                  45
Glu Leu Arg Glu Pro Asn Lys Phe Leu Lys Cys His Phe Phe Asn Thr
     50                  55                  60
Phe Phe Tyr Lys Lys Leu Ile Asn Gly Gly Tyr Asp Tyr Lys Ser Val
 65                  70                  75                  80
Arg Glu Trp Thr Thr Arg Arg Lys Leu Gly
                 85                  90
```

<210> SEQ ID NO 35
<211> LENGTH: 90
<212> TYPE: PRT
<213> ORGANISM: Artificial
<220> FEATURE:
<223> OTHER INFORMATION: MutJ bdSENP1

<400> SEQUENCE: 35

```
Gly Gly Arg Lys Glu Ser Glu Thr Leu Ser Val His Glu Ala Ser Ser
 1               5                  10                  15
Ile Val Ile Thr Arg Glu Ile Leu Gln Cys Leu Asn Asp Lys Glu Trp
                20                  25                  30
Leu Asn Asp Glu Val Ile Asn Leu Tyr Leu Glu Leu Leu Lys Glu Arg
         35                  40                  45
Glu Leu Arg Glu Pro Asn Lys Phe Leu Lys Cys His Phe Phe Asn Thr
     50                  55                  60
Phe Phe Tyr Lys Lys Leu Ile Asn Gly Gly Tyr Asp Tyr Lys Ser Val
 65                  70                  75                  80
Arg Ser Trp Thr Thr Thr Arg Lys Leu Gly
                 85                  90
```

<210> SEQ ID NO 36
<211> LENGTH: 90
<212> TYPE: PRT
<213> ORGANISM: Artificial
<220> FEATURE:
<223> OTHER INFORMATION: MutK bdSENP1

<400> SEQUENCE: 36

```
Gly Gly Arg Lys Val Ser Glu Thr Leu Ser Val His Glu Ala Ser Gln
 1               5                  10                  15
```

Ile Val Ile Thr Arg Glu Ile Leu Gln Cys Leu Asn Asp Lys Glu Trp
            20                  25                  30

Leu Asn Asp Glu Val Ile Asn Leu Tyr Leu Glu Leu Leu Lys Glu Arg
        35                  40                  45

Glu Leu Arg Glu Pro Asn Lys Phe Leu Lys Cys His Phe Phe Asn Thr
    50                  55                  60

Phe Phe Tyr Lys Lys Leu Ile Asn Gly Gly Tyr Asp Tyr Lys Ser Val
65                  70                  75                  80

Arg Val Trp Thr Thr Gly Arg Lys Leu Gly
                85                  90

<210> SEQ ID NO 37
<211> LENGTH: 90
<212> TYPE: PRT
<213> ORGANISM: Artificial
<220> FEATURE:
<223> OTHER INFORMATION: MutL bdSENP1

<400> SEQUENCE: 37

Gly Gly Arg Lys Leu Ser Glu Thr Leu Ser Val His Glu Ala Ser Val
1               5                   10                  15

Ile Val Ile Thr Arg Glu Ile Leu Gln Cys Leu Asn Asp Lys Glu Trp
            20                  25                  30

Leu Asn Asp Glu Val Ile Asn Leu Tyr Leu Glu Leu Leu Lys Glu Arg
        35                  40                  45

Glu Leu Arg Glu Pro Asn Lys Phe Leu Lys Cys His Phe Phe Asn Thr
    50                  55                  60

Phe Phe Tyr Lys Lys Leu Ile Asn Gly Gly Tyr Asp Tyr Lys Ser Val
65                  70                  75                  80

Arg Pro Trp Thr Thr Ala Arg Lys Leu Gly
                85                  90

<210> SEQ ID NO 38
<211> LENGTH: 90
<212> TYPE: PRT
<213> ORGANISM: Artificial
<220> FEATURE:
<223> OTHER INFORMATION: MutM bdSENP1

<400> SEQUENCE: 38

Gly Gly Arg Lys Ala Ser Glu Thr Leu Ser Val His Glu Ala Ser Trp
1               5                   10                  15

Ile Val Ile Thr Arg Glu Ile Leu Gln Cys Leu Asn Asp Lys Glu Trp
            20                  25                  30

Leu Asn Asp Glu Val Ile Asn Leu Tyr Leu Glu Leu Leu Lys Glu Arg
        35                  40                  45

Glu Leu Arg Glu Pro Asn Lys Phe Leu Lys Cys His Phe Phe Asn Thr
    50                  55                  60

Phe Phe Tyr Lys Lys Leu Ile Asn Gly Gly Tyr Asp Tyr Lys Ser Val
65                  70                  75                  80

Arg Arg Trp Thr Thr Glu Arg Lys Leu Gly
                85                  90

<210> SEQ ID NO 39
<211> LENGTH: 90
<212> TYPE: PRT
<213> ORGANISM: Artificial
<220> FEATURE:
<223> OTHER INFORMATION: MutN bdSENP1

<400> SEQUENCE: 39

```
Gly Gly Arg Lys Ser Ser Glu Thr Leu Ser Val His Glu Ala Ser Pro
1               5                   10                  15

Ile Val Ile Thr Arg Glu Ile Leu Gln Cys Leu Asn Asp Lys Glu Trp
            20                  25                  30

Leu Asn Asp Glu Val Ile Asn Leu Tyr Leu Glu Leu Leu Lys Glu Arg
        35                  40                  45

Glu Leu Arg Glu Pro Asn Lys Phe Leu Lys Cys His Phe Phe Asn Thr
    50                  55                  60

Phe Phe Tyr Lys Lys Leu Ile Asn Gly Gly Tyr Asp Tyr Lys Ser Val
65                  70                  75                  80

Arg Arg Trp Thr Thr Arg Arg Lys Leu Gly
                85                  90
```

<210> SEQ ID NO 40
<211> LENGTH: 90
<212> TYPE: PRT
<213> ORGANISM: Artificial
<220> FEATURE:
<223> OTHER INFORMATION: Mut0 bdSENP1

<400> SEQUENCE: 40

```
Gly Gly Arg Lys Arg Ser Glu Thr Leu Ser Val His Glu Ala Ser Arg
1               5                   10                  15

Ile Val Ile Thr Arg Glu Ile Leu Gln Cys Leu Asn Asp Lys Glu Trp
            20                  25                  30

Leu Asn Asp Glu Val Ile Asn Leu Tyr Leu Glu Leu Leu Lys Glu Arg
        35                  40                  45

Glu Leu Arg Glu Pro Asn Lys Phe Leu Lys Cys His Phe Phe Asn Thr
    50                  55                  60

Phe Phe Tyr Lys Lys Leu Ile Asn Gly Gly Tyr Asp Tyr Lys Ser Val
65                  70                  75                  80

Arg Gly Trp Thr Thr Leu Arg Lys Leu Gly
                85                  90
```

<210> SEQ ID NO 41
<211> LENGTH: 97
<212> TYPE: PRT
<213> ORGANISM: Artificial
<220> FEATURE:
<223> OTHER INFORMATION: Mut1 bdSUMO residues 1-97

<400> SEQUENCE: 41

```
Met Ser Ala Ala Gly Gly Glu Glu Asp Lys Lys Pro Ala Gly Gly Glu
1               5                   10                  15

Gly Gly Gly Ala His Ile Asn Leu Lys Val Lys Gly Gln Asp Gly Asn
            20                  25                  30

Glu Val Phe Phe Arg Ile Lys Arg Ser Thr Gln Leu Lys Lys Leu Met
        35                  40                  45

Asn Ala Tyr Cys Asp Arg Gln Ser Val Asp Met Lys Ala Ile Ala Phe
    50                  55                  60

Leu Phe Lys Gly Arg Arg Leu Arg Ala Glu Arg Thr Pro Asp Glu Leu
65                  70                  75                  80

Glu Met Glu Asp Gly Asp Glu Ile Asp Ala Met Leu His Gln Thr Gly
                85                  90                  95

Gly
```

<210> SEQ ID NO 42
<211> LENGTH: 97
<212> TYPE: PRT
<213> ORGANISM: Artificial
<220> FEATURE:
<223> OTHER INFORMATION: Mut2 bdSUMO residues 1-97

<400> SEQUENCE: 42

Met Ser Ala Ala Gly Gly Glu Glu Asp Lys Lys Pro Ala Gly Gly Glu
1               5                   10                  15

Gly Gly Gly Ala His Ile Asn Leu Lys Val Lys Gly Gln Asp Gly Asn
                20                  25                  30

Glu Val Phe Phe Arg Ile Lys Arg Ser Thr Gln Leu Lys Lys Leu Met
            35                  40                  45

Asn Ala Tyr Cys Asp Arg Gln Ser Val Asp Met Thr Ala Ile Ala Phe
        50                  55                  60

Leu Phe Lys Gly Arg Arg Leu Arg Ala Glu Cys Thr Pro Asp Glu Leu
65                  70                  75                  80

Glu Met Glu Asp Gly Asp Glu Ile Asp Ala Met Leu His Gln Thr Gly
                85                  90                  95

Gly

<210> SEQ ID NO 43
<211> LENGTH: 97
<212> TYPE: PRT
<213> ORGANISM: Artificial
<220> FEATURE:
<223> OTHER INFORMATION: Mut3 bdSUMO residues 1-97

<400> SEQUENCE: 43

Met Ser Ala Ala Gly Gly Glu Glu Asp Lys Lys Pro Ala Gly Gly Glu
1               5                   10                  15

Gly Gly Gly Ala His Ile Asn Leu Lys Val Lys Gly Gln Asp Gly Asn
                20                  25                  30

Glu Val Phe Phe Arg Ile Lys Arg Ser Thr Gln Leu Lys Lys Leu Met
            35                  40                  45

Asn Ala Tyr Cys Asp Arg Gln Ser Val Asp Met His Ala Ile Ala Phe
        50                  55                  60

Leu Phe Lys Gly Arg Arg Leu Arg Ala Glu Lys Thr Pro Asp Glu Leu
65                  70                  75                  80

Glu Met Glu Asp Gly Asp Glu Ile Asp Ala Met Leu His Gln Thr Gly
                85                  90                  95

Gly

<210> SEQ ID NO 44
<211> LENGTH: 97
<212> TYPE: PRT
<213> ORGANISM: Artificial
<220> FEATURE:
<223> OTHER INFORMATION: Mut4 bdSUMO residues 1-97

<400> SEQUENCE: 44

Met Ser Ala Ala Gly Gly Glu Glu Asp Lys Lys Pro Ala Gly Gly Glu
1               5                   10                  15

Gly Gly Gly Ala His Ile Asn Leu Lys Val Lys Gly Gln Asp Gly Asn
                20                  25                  30

Glu Val Phe Phe Arg Ile Lys Arg Ser Thr Gln Leu Lys Lys Leu Met
            35                  40                  45

```
Asn Ala Tyr Cys Asp Arg Gln Ser Val Asp Met Arg Ala Ile Ala Phe
            50                  55                  60

Leu Phe Arg Gly Arg Arg Leu Arg Ala Glu Val Thr Pro Asp Glu Leu
 65                  70                  75                  80

Glu Met Glu Asp Gly Asp Glu Ile Asp Ala Met Leu His Gln Thr Gly
                    85                  90                  95

Gly

<210> SEQ ID NO 45
<211> LENGTH: 97
<212> TYPE: PRT
<213> ORGANISM: Artificial
<220> FEATURE:
<223> OTHER INFORMATION: Mut5 bdSUMO residues 1-97

<400> SEQUENCE: 45

Met Ser Ala Ala Gly Gly Glu Glu Asp Lys Lys Pro Ala Gly Gly Glu
  1               5                  10                  15

Gly Gly Gly Ala His Ile Asn Leu Lys Val Lys Gly Gln Asp Gly Asn
                20                  25                  30

Glu Val Phe Phe Arg Ile Lys Arg Ser Thr Gln Leu Lys Lys Leu Met
            35                  40                  45

Asn Ala Tyr Cys Asp Arg Gln Ser Val Asp Met Thr Ala Ile Ala Phe
            50                  55                  60

Leu Phe Lys Gly Arg Arg Leu Arg Ala Glu Phe Thr Pro Asp Glu Leu
 65                  70                  75                  80

Glu Met Glu Asp Gly Asp Glu Ile Asp Ala Met Leu His Gln Thr Gly
                    85                  90                  95

Gly

<210> SEQ ID NO 46
<211> LENGTH: 97
<212> TYPE: PRT
<213> ORGANISM: Artificial
<220> FEATURE:
<223> OTHER INFORMATION: Mut6 bdSUMO residues 1-97

<400> SEQUENCE: 46

Met Ser Ala Ala Gly Gly Glu Glu Asp Lys Lys Pro Ala Gly Gly Glu
  1               5                  10                  15

Gly Gly Gly Ala His Ile Asn Leu Lys Val Lys Gly Gln Asp Gly Asn
                20                  25                  30

Glu Val Phe Phe Arg Ile Lys Arg Ser Thr Gln Leu Lys Lys Leu Met
            35                  40                  45

Asn Ala Tyr Cys Asp Arg Gln Ser Val Asp Met His Ala Ile Ala Phe
            50                  55                  60

Leu Phe Lys Gly Arg Arg Leu Arg Ala Glu Gln Thr Pro Asp Glu Leu
 65                  70                  75                  80

Glu Met Glu Asp Gly Asp Glu Ile Asp Ala Met Leu His Gln Thr Gly
                    85                  90                  95

Gly

<210> SEQ ID NO 47
<211> LENGTH: 97
<212> TYPE: PRT
<213> ORGANISM: Artificial
<220> FEATURE:
<223> OTHER INFORMATION: Mut7 bdSUMO residues 1-97
```

```
<400> SEQUENCE: 47

Met Ser Ala Ala Gly Gly Glu Glu Asp Lys Lys Pro Ala Gly Gly Glu
1               5                   10                  15

Gly Gly Gly Ala His Ile Asn Leu Lys Val Lys Gly Gln Asp Gly Asn
            20                  25                  30

Glu Val Phe Phe Arg Ile Lys Arg Ser Thr Gln Leu Lys Lys Leu Met
        35                  40                  45

Asn Ala Tyr Cys Asp Arg Gln Ser Val Asp Met Asp Ala Ile Ala Phe
    50                  55                  60

Leu Phe Arg Gly Arg Arg Leu Arg Ala Glu Cys Thr Pro Asp Glu Leu
65                  70                  75                  80

Glu Met Glu Asp Gly Asp Glu Ile Asp Ala Met Leu His Gln Thr Gly
                85                  90                  95

Gly

<210> SEQ ID NO 48
<211> LENGTH: 97
<212> TYPE: PRT
<213> ORGANISM: Artificial
<220> FEATURE:
<223> OTHER INFORMATION: Mut8 bdSUMO residues 1-97

<400> SEQUENCE: 48

Met Ser Ala Ala Gly Gly Glu Glu Asp Lys Lys Pro Ala Gly Gly Glu
1               5                   10                  15

Gly Gly Gly Ala His Ile Asn Leu Lys Val Lys Gly Gln Asp Gly Asn
            20                  25                  30

Glu Val Phe Phe Arg Ile Lys Arg Ser Thr Gln Leu Lys Lys Leu Met
        35                  40                  45

Asn Ala Tyr Cys Asp Arg Gln Ser Val Asp Met Pro Ala Ile Ala Phe
    50                  55                  60

Leu Phe Lys Gly Arg Arg Leu Arg Ala Glu Gln Thr Pro Asp Glu Leu
65                  70                  75                  80

Glu Met Glu Asp Gly Asp Glu Ile Asp Ala Met Leu His Gln Thr Gly
                85                  90                  95

Gly

<210> SEQ ID NO 49
<211> LENGTH: 97
<212> TYPE: PRT
<213> ORGANISM: Artificial
<220> FEATURE:
<223> OTHER INFORMATION: Mut9 bdSUMO residues 1-97

<400> SEQUENCE: 49

Met Ser Ala Ala Gly Gly Glu Glu Asp Lys Lys Pro Ala Gly Gly Glu
1               5                   10                  15

Gly Gly Gly Ala His Ile Asn Leu Lys Val Lys Gly Gln Asp Gly Asn
            20                  25                  30

Glu Val Phe Phe Arg Ile Lys Arg Ser Thr Gln Leu Lys Lys Leu Met
        35                  40                  45

Asn Ala Tyr Cys Asp Arg Gln Ser Val Asp Met Ala Ala Ile Ala Phe
    50                  55                  60

Leu Phe Lys Gly Arg Arg Leu Arg Ala Glu Tyr Thr Pro Asp Glu Leu
65                  70                  75                  80

Glu Met Glu Asp Gly Asp Glu Ile Asp Ala Met Leu His Gln Thr Gly
                85                  90                  95
```

<210> SEQ ID NO 50
<211> LENGTH: 97
<212> TYPE: PRT
<213> ORGANISM: Artificial
<220> FEATURE:
<223> OTHER INFORMATION: Mut10 bdSUMO residues 1-97

<400> SEQUENCE: 50

Met Ser Ala Ala Gly Gly Glu Glu Asp Lys Lys Pro Ala Gly Gly Glu
1               5                   10                  15

Gly Gly Gly Ala His Ile Asn Leu Lys Val Lys Gly Gln Asp Gly Asn
            20                  25                  30

Glu Val Phe Phe Arg Ile Lys Arg Ser Thr Gln Leu Lys Lys Leu Met
        35                  40                  45

Asn Ala Tyr Cys Asp Arg Gln Ser Val Asp Met Thr Ala Ile Ala Phe
    50                  55                  60

Leu Phe Lys Gly Arg Arg Leu Arg Ala Glu Arg Thr Pro Asp Glu Leu
65                  70                  75                  80

Glu Met Glu Asp Gly Asp Glu Ile Asp Ala Met Leu His Gln Thr Gly
                85                  90                  95

Gly

<210> SEQ ID NO 51
<211> LENGTH: 97
<212> TYPE: PRT
<213> ORGANISM: Artificial
<220> FEATURE:
<223> OTHER INFORMATION: Mut11 bdSUMO residues 1-97

<400> SEQUENCE: 51

Met Ser Ala Ala Gly Gly Glu Glu Asp Lys Lys Pro Ala Gly Gly Glu
1               5                   10                  15

Gly Gly Gly Ala His Ile Asn Leu Lys Val Lys Gly Gln Asp Gly Asn
            20                  25                  30

Glu Val Phe Phe Arg Ile Lys Arg Ser Thr Gln Leu Lys Lys Leu Met
        35                  40                  45

Asn Ala Tyr Cys Asp Arg Gln Ser Val Asp Met Ser Ala Ile Ala Phe
    50                  55                  60

Leu Phe Lys Gly Arg Arg Leu Arg Ala Glu Trp Thr Pro Asp Glu Leu
65                  70                  75                  80

Glu Met Glu Asp Gly Asp Glu Ile Asp Ala Met Leu His Gln Thr Gly
                85                  90                  95

Gly

<210> SEQ ID NO 52
<211> LENGTH: 97
<212> TYPE: PRT
<213> ORGANISM: Artificial
<220> FEATURE:
<223> OTHER INFORMATION: Mut12 bdSUMO residues 1-97

<400> SEQUENCE: 52

Met Ser Ala Ala Gly Gly Glu Glu Asp Lys Lys Pro Ala Gly Gly Glu
1               5                   10                  15

Gly Gly Gly Ala His Ile Asn Leu Lys Val Lys Gly Gln Asp Gly Asn
            20                  25                  30

```
Glu Val Phe Phe Arg Ile Lys Arg Ser Thr Gln Leu Lys Lys Leu Met
            35                  40                  45

Asn Ala Tyr Cys Asp Arg Gln Ser Val Asp Met Ser Ala Ile Ala Phe
 50                  55                  60

Leu Phe Lys Gly Arg Arg Leu Arg Ala Glu His Thr Pro Asp Glu Leu
 65                  70                  75                  80

Glu Met Glu Asp Gly Asp Glu Ile Asp Ala Met Leu His Gln Thr Gly
                 85                  90                  95

Gly

<210> SEQ ID NO 53
<211> LENGTH: 97
<212> TYPE: PRT
<213> ORGANISM: Artificial
<220> FEATURE:
<223> OTHER INFORMATION: Mut13 bdSUMO residues 1-97

<400> SEQUENCE: 53

Met Ser Ala Ala Gly Gly Glu Glu Asp Lys Lys Pro Ala Gly Gly Glu
 1               5                  10                  15

Gly Gly Gly Ala His Ile Asn Leu Lys Val Lys Gly Gln Asp Gly Asn
                20                  25                  30

Glu Val Phe Phe Arg Ile Lys Arg Ser Thr Gln Leu Lys Lys Leu Met
            35                  40                  45

Asn Ala Tyr Cys Asp Arg Gln Ser Val Asp Met Ser Ala Ile Ala Phe
 50                  55                  60

Leu Phe Lys Gly Arg Arg Leu Arg Ala Glu Ala Thr Pro Asp Glu Leu
 65                  70                  75                  80

Glu Met Glu Asp Gly Asp Glu Ile Asp Ala Met Leu His Gln Thr Gly
                 85                  90                  95

Gly

<210> SEQ ID NO 54
<211> LENGTH: 97
<212> TYPE: PRT
<213> ORGANISM: Artificial
<220> FEATURE:
<223> OTHER INFORMATION: Mut14 bdSUMO residues 1-97

<400> SEQUENCE: 54

Met Ser Ala Ala Gly Gly Glu Glu Asp Lys Lys Pro Ala Gly Gly Glu
 1               5                  10                  15

Gly Gly Gly Ala His Ile Asn Leu Lys Val Lys Gly Gln Asp Gly Asn
                20                  25                  30

Glu Val Phe Phe Arg Ile Lys Arg Ser Thr Gln Leu Lys Lys Leu Met
            35                  40                  45

Asn Ala Tyr Cys Asp Arg Gln Ser Val Asp Met Asn Ala Ile Ala Phe
 50                  55                  60

Leu Phe Lys Gly Arg Arg Leu Arg Ala Glu Trp Thr Pro Asp Glu Leu
 65                  70                  75                  80

Glu Met Glu Asp Gly Asp Glu Ile Asp Ala Met Leu His Gln Thr Gly
                 85                  90                  95

Gly

<210> SEQ ID NO 55
<211> LENGTH: 97
<212> TYPE: PRT
<213> ORGANISM: Artificial
```

<220> FEATURE:
<223> OTHER INFORMATION: Mut15 bdSUMO residues 1-97

<400> SEQUENCE: 55

```
Met Ser Ala Ala Gly Gly Glu Glu Asp Lys Lys Pro Ala Gly Gly Glu
1               5                   10                  15

Gly Gly Gly Ala His Ile Asn Leu Lys Val Lys Gly Gln Asp Gly Asn
            20                  25                  30

Glu Val Phe Phe Arg Ile Lys Arg Ser Thr Gln Leu Lys Lys Leu Met
        35                  40                  45

Asn Ala Tyr Cys Asp Arg Gln Ser Val Asp Met Asn Ala Ile Ala Phe
    50                  55                  60

Leu Phe Lys Gly Arg Arg Leu Arg Ala Glu Ala Thr Pro Asp Glu Leu
65                  70                  75                  80

Glu Met Glu Asp Gly Asp Glu Ile Asp Ala Met Leu His Gln Thr Gly
                85                  90                  95

Gly
```

<210> SEQ ID NO 56
<211> LENGTH: 234
<212> TYPE: PRT
<213> ORGANISM: Artificial
<220> FEATURE:
<223> OTHER INFORMATION: MutA bdSENP1 residues 248-481

<400> SEQUENCE: 56

```
Pro Phe Val Pro Leu Thr Asp Glu Asp Glu Asp Asn Val Arg His Ala
1               5                   10                  15

Leu Gly Gly Arg Lys Pro Ser Glu Thr Leu Ser Val His Glu Ala Ser
            20                  25                  30

Gly Ile Val Ile Thr Arg Glu Ile Leu Gln Cys Leu Asn Asp Lys Glu
        35                  40                  45

Trp Leu Asn Asp Glu Val Ile Asn Leu Tyr Leu Glu Leu Leu Lys Glu
    50                  55                  60

Arg Glu Leu Arg Glu Pro Asn Lys Phe Leu Lys Cys His Phe Phe Asn
65                  70                  75                  80

Thr Phe Phe Tyr Lys Lys Leu Ile Asn Gly Gly Tyr Asp Tyr Lys Ser
                85                  90                  95

Val Arg Glu Trp Thr Thr Pro Arg Lys Leu Gly Tyr Asn Leu Ile Asp
                100                 105                 110

Cys Asp Lys Ile Phe Val Pro Ile His Lys Asp Val His Trp Cys Leu
            115                 120                 125

Ala Val Ile Asn Ile Lys Glu Lys Lys Phe Gln Tyr Leu Asp Ser Leu
    130                 135                 140

Gly Tyr Met Asp Met Lys Ala Leu Arg Ile Leu Ala Lys Tyr Leu Val
145                 150                 155                 160

Asp Glu Val Lys Asp Lys Ser Gly Lys Gln Ile Asp Val His Ala Trp
                165                 170                 175

Lys Gln Glu Gly Val Gln Asn Leu Pro Leu Gln Glu Asn Gly Trp Asp
            180                 185                 190

Cys Gly Met Phe Met Leu Lys Tyr Ile Asp Phe Tyr Ser Arg Asp Met
        195                 200                 205

Glu Leu Val Phe Gly Gln Lys His Met Ser Tyr Phe Arg Arg Arg Thr
    210                 215                 220

Ala Lys Glu Ile Leu Asp Leu Lys Ala Gly
225                 230
```

<210> SEQ ID NO 57
<211> LENGTH: 234
<212> TYPE: PRT
<213> ORGANISM: Artificial
<220> FEATURE:
<223> OTHER INFORMATION: MutB bdSENP1 residues 248-481

<400> SEQUENCE: 57

Pro Phe Val Pro Leu Thr Asp Glu Asp Glu Asp Asn Val Arg His Ala
1               5                   10                  15

Leu Gly Gly Arg Lys Arg Ser Glu Thr Leu Ser Val His Glu Ala Ser
            20                  25                  30

Ser Ile Val Ile Thr Arg Glu Ile Leu Gln Cys Leu Asn Asp Lys Glu
        35                  40                  45

Trp Leu Asn Asp Glu Val Ile Asn Leu Tyr Leu Glu Leu Leu Lys Glu
    50                  55                  60

Arg Glu Leu Arg Glu Pro Asn Lys Phe Leu Lys Cys His Phe Phe Asn
65                  70                  75                  80

Thr Phe Phe Tyr Lys Lys Leu Ile Asn Gly Gly Tyr Asp Tyr Lys Ser
                85                  90                  95

Val Arg Glu Trp Thr Thr Lys Arg Lys Leu Gly Tyr Asn Leu Ile Asp
            100                 105                 110

Cys Asp Lys Ile Phe Val Pro Ile His Lys Asp Val His Trp Cys Leu
        115                 120                 125

Ala Val Ile Asn Ile Lys Glu Lys Lys Phe Gln Tyr Leu Asp Ser Leu
    130                 135                 140

Gly Tyr Met Asp Met Lys Ala Leu Arg Ile Leu Ala Lys Tyr Leu Val
145                 150                 155                 160

Asp Glu Val Lys Asp Lys Ser Gly Lys Gln Ile Asp Val His Ala Trp
                165                 170                 175

Lys Gln Glu Gly Val Gln Asn Leu Pro Leu Gln Glu Asn Gly Trp Asp
            180                 185                 190

Cys Gly Met Phe Met Leu Lys Tyr Ile Asp Phe Tyr Ser Arg Asp Met
        195                 200                 205

Glu Leu Val Phe Gly Gln Lys His Met Ser Tyr Phe Arg Arg Arg Thr
    210                 215                 220

Ala Lys Glu Ile Leu Asp Leu Lys Ala Gly
225                 230

<210> SEQ ID NO 58
<211> LENGTH: 234
<212> TYPE: PRT
<213> ORGANISM: Artificial
<220> FEATURE:
<223> OTHER INFORMATION: MutC bdSENP1 residues 248-481

<400> SEQUENCE: 58

Pro Phe Val Pro Leu Thr Asp Glu Asp Glu Asp Asn Val Arg His Ala
1               5                   10                  15

Leu Gly Gly Arg Lys Ser Ser Glu Thr Leu Ser Val His Glu Ala Ser
            20                  25                  30

Ala Ile Val Ile Thr Arg Glu Ile Leu Gln Cys Leu Asn Asp Lys Glu
        35                  40                  45

Trp Leu Asn Asp Glu Val Ile Asn Leu Tyr Leu Glu Leu Leu Lys Glu
    50                  55                  60

Arg Glu Leu Arg Glu Pro Asn Lys Phe Leu Lys Cys His Phe Phe Asn

Thr Phe Phe Tyr Lys Lys Leu Ile Asn Gly Gly Tyr Asp Tyr Lys Ser
65                  70                  75                  80

Val Arg Gly Trp Thr Thr Val Arg Lys Leu Gly Tyr Asn Leu Ile Asp
            85                  90                  95

Cys Asp Lys Ile Phe Val Pro Ile His Lys Asp Val His Trp Cys Leu
        100                 105                 110

Ala Val Ile Asn Ile Lys Glu Lys Lys Phe Gln Tyr Leu Asp Ser Leu
    115                 120                 125

Gly Tyr Met Asp Met Lys Ala Leu Arg Ile Leu Ala Lys Tyr Leu Val
130                 135                 140

Asp Glu Val Lys Asp Lys Ser Gly Lys Gln Ile Asp Val His Ala Trp
145                 150                 155                 160

Lys Gln Glu Gly Val Gln Asn Leu Pro Leu Gln Glu Asn Gly Trp Asp
            165                 170                 175

Cys Gly Met Phe Met Leu Lys Tyr Ile Asp Phe Tyr Ser Arg Asp Met
        180                 185                 190

Glu Leu Val Phe Gly Gln Lys His Met Ser Tyr Phe Arg Arg Arg Thr
    195                 200                 205

Ala Lys Glu Ile Leu Asp Leu Lys Ala Gly
210                 215                 220

<210> SEQ ID NO 59
<211> LENGTH: 234
<212> TYPE: PRT
<213> ORGANISM: Artificial
<220> FEATURE:
<223> OTHER INFORMATION: MutD bdSENP1 residues 248-481

<400> SEQUENCE: 59

Pro Phe Val Pro Leu Thr Asp Glu Asp Glu Asp Asn Val Arg His Ala
1               5                   10                  15

Leu Gly Gly Arg Lys Pro Ser Glu Thr Leu Ser Val His Glu Ala Ser
            20                  25                  30

Glu Ile Val Ile Thr Arg Glu Ile Leu Gln Cys Leu Asn Asp Lys Glu
        35                  40                  45

Trp Leu Asn Asp Glu Val Ile Asn Leu Tyr Leu Glu Leu Leu Lys Glu
    50                  55                  60

Arg Glu Leu Arg Glu Pro Asn Lys Phe Leu Lys Cys His Phe Phe Asn
65                  70                  75                  80

Thr Phe Pro Tyr Lys Lys Leu Ile Asn Gly Gly Tyr Asp Tyr Lys Ser
            85                  90                  95

Val Arg Glu Trp Thr Thr Gln Arg Lys Leu Gly Tyr Asn Leu Ile Asp
        100                 105                 110

Cys Asp Lys Ile Phe Val Pro Ile His Lys Asp Val His Trp Cys Leu
    115                 120                 125

Ala Val Ile Asn Ile Lys Glu Lys Lys Phe Gln Tyr Leu Asp Ser Leu
130                 135                 140

Gly Tyr Met Asp Met Lys Ala Leu Arg Ile Leu Ala Lys Tyr Leu Val
145                 150                 155                 160

Asp Glu Val Lys Asp Lys Ser Gly Lys Gln Ile Asp Val His Ala Trp
            165                 170                 175

Lys Gln Glu Gly Val Gln Asn Leu Pro Leu Gln Glu Asn Gly Trp Asp
        180                 185                 190

Cys Gly Met Phe Met Leu Lys Tyr Ile Asp Phe Tyr Ser Arg Asp Met

```
                195                 200                 205
Glu Leu Val Phe Gly Gln Lys His Met Ser Tyr Phe Arg Arg Arg Thr
    210                 215                 220

Ala Lys Glu Ile Leu Asp Leu Lys Ala Gly
225                 230
```

<210> SEQ ID NO 60
<211> LENGTH: 234
<212> TYPE: PRT
<213> ORGANISM: Artificial
<220> FEATURE:
<223> OTHER INFORMATION: MutE bdSENP1 residues 248-481

<400> SEQUENCE: 60

```
Pro Phe Val Pro Leu Thr Asp Glu Asp Glu Asp Asn Val Arg His Ala
1               5                   10                  15

Leu Gly Gly Arg Lys Arg Ser Glu Thr Leu Ser Val His Glu Ala Ser
            20                  25                  30

Gly Ile Val Ile Thr Arg Glu Ile Leu Gln Cys Leu Asn Asp Lys Glu
        35                  40                  45

Trp Leu Asn Asp Glu Val Ile Asn Leu Tyr Leu Glu Leu Leu Lys Glu
    50                  55                  60

Arg Glu Leu Arg Glu Pro Asn Lys Phe Leu Lys Cys His Phe Phe Asn
65                  70                  75                  80

Thr Phe Phe Tyr Lys Lys Leu Ile Asn Gly Gly Tyr Asp Tyr Lys Ser
                85                  90                  95

Val Arg Tyr Trp Thr Thr Ala Arg Lys Leu Gly Tyr Asn Leu Ile Asp
            100                 105                 110

Cys Asp Lys Ile Phe Val Pro Ile His Lys Asp Val His Trp Cys Leu
        115                 120                 125

Ala Val Ile Asn Ile Lys Glu Lys Lys Phe Gln Tyr Leu Asp Ser Leu
    130                 135                 140

Gly Tyr Met Asp Met Lys Ala Leu Arg Ile Leu Ala Lys Tyr Leu Val
145                 150                 155                 160

Asp Glu Val Lys Asp Lys Ser Gly Lys Gln Ile Asp Val His Ala Trp
                165                 170                 175

Lys Gln Glu Gly Val Gln Asn Leu Pro Leu Gln Glu Asn Gly Trp Asp
            180                 185                 190

Cys Gly Met Phe Met Leu Lys Tyr Ile Asp Phe Tyr Ser Arg Asp Met
        195                 200                 205

Glu Leu Val Phe Gly Gln Lys His Met Ser Tyr Phe Arg Arg Arg Thr
    210                 215                 220

Ala Lys Glu Ile Leu Asp Leu Lys Ala Gly
225                 230
```

<210> SEQ ID NO 61
<211> LENGTH: 234
<212> TYPE: PRT
<213> ORGANISM: Artificial
<220> FEATURE:
<223> OTHER INFORMATION: MutF bdSENP1 residues 248-481

<400> SEQUENCE: 61

```
Pro Phe Val Pro Leu Thr Asp Glu Asp Glu Asp Asn Val Arg His Ala
1               5                   10                  15

Leu Gly Gly Arg Lys Pro Ser Glu Thr Leu Ser Val His Glu Ala Ser
            20                  25                  30
```

Cys Ile Val Ile Thr Arg Glu Ile Leu Gln Cys Leu Asn Asp Lys Glu
            35                  40                  45

Trp Leu Asn Asp Glu Val Ile Asn Leu Tyr Leu Glu Leu Leu Lys Glu
50                      55                  60

Arg Glu Leu Arg Glu Pro Asn Lys Phe Leu Lys Cys His Phe Phe Asn
65                      70                  75                  80

Thr Phe Phe Tyr Lys Lys Leu Ile Asn Gly Gly Tyr Asp Tyr Lys Ser
                85                  90                  95

Val Arg Leu Trp Thr Thr Arg Arg Lys Leu Gly Tyr Asn Leu Ile Asp
            100                 105                 110

Cys Asp Lys Ile Phe Val Pro Ile His Lys Asp Val His Trp Cys Leu
            115                 120                 125

Ala Val Ile Asn Ile Lys Glu Lys Lys Phe Gln Tyr Leu Asp Ser Leu
130                 135                 140

Gly Tyr Met Asp Met Lys Ala Leu Arg Ile Leu Ala Lys Tyr Leu Val
145                 150                 155                 160

Asp Glu Val Lys Asp Lys Ser Gly Lys Gln Ile Asp Val His Ala Trp
                165                 170                 175

Lys Gln Glu Gly Val Gln Asn Leu Pro Leu Gln Glu Asn Gly Trp Asp
            180                 185                 190

Cys Gly Met Phe Met Leu Lys Tyr Ile Asp Phe Tyr Ser Arg Asp Met
            195                 200                 205

Glu Leu Val Phe Gly Gln Lys His Met Ser Tyr Phe Arg Arg Arg Thr
210                 215                 220

Ala Lys Glu Ile Leu Asp Leu Lys Ala Gly
225                 230

<210> SEQ ID NO 62
<211> LENGTH: 233
<212> TYPE: PRT
<213> ORGANISM: Artificial
<220> FEATURE:
<223> OTHER INFORMATION: MutG bdSENP1 residues 248-481

<400> SEQUENCE: 62

Pro Phe Val Pro Leu Thr Asp Glu Asp Glu Asn Val Arg His Ala
1               5                   10                  15

Leu Gly Gly Arg Lys Ser Ser Glu Thr Leu Ser Val His Glu Ala Ser
            20                  25                  30

His Ile Val Ile Thr Arg Glu Ile Leu Gln Cys Leu Asn Asp Lys Glu
            35                  40                  45

Trp Leu Asn Asp Glu Val Ile Asn Leu Tyr Leu Glu Leu Leu Lys Glu
50                      55                  60

Arg Glu Leu Arg Glu Pro Asn Lys Phe Leu Lys Cys His Phe Phe Asn
65                      70                  75                  80

Thr Phe Phe Tyr Lys Lys Leu Ile Asn Gly Gly Tyr Asp Tyr Lys Ser
                85                  90                  95

Val Arg Arg Trp Thr Thr Val Lys Leu Gly Tyr Asn Leu Ile Asp Cys
            100                 105                 110

Asp Lys Ile Phe Val Pro Ile His Lys Asp Val His Trp Cys Leu Ala
            115                 120                 125

Val Ile Asn Ile Lys Glu Lys Lys Phe Gln Tyr Leu Asp Ser Leu Gly
130                 135                 140

Tyr Met Asp Met Lys Ala Leu Arg Ile Leu Ala Lys Tyr Leu Val Asp
145                 150                 155                 160

```
Glu Val Lys Asp Lys Ser Gly Lys Gln Ile Asp Val His Ala Trp Lys
            165                 170                 175

Gln Glu Gly Val Gln Asn Leu Pro Leu Gln Glu Asn Gly Trp Asp Cys
        180                 185                 190

Gly Met Phe Met Leu Lys Tyr Ile Asp Phe Tyr Ser Arg Asp Met Glu
        195                 200                 205

Leu Val Phe Gly Gln Lys His Met Ser Tyr Phe Arg Arg Arg Thr Ala
210                 215                 220

Lys Glu Ile Leu Asp Leu Lys Ala Gly
225                 230
```

<210> SEQ ID NO 63
<211> LENGTH: 233
<212> TYPE: PRT
<213> ORGANISM: Artificial
<220> FEATURE:
<223> OTHER INFORMATION: MutH bdSENP1 residues 248-481

<400> SEQUENCE: 63

```
Pro Phe Val Pro Leu Thr Asp Glu Asp Glu Asp Asn Val Arg His Ala
1               5                   10                  15

Leu Gly Gly Arg Lys Pro Ser Glu Thr Leu Ser Val His Glu Ala Ser
            20                  25                  30

Ala Ile Val Ile Thr Arg Glu Ile Leu Gln Cys Leu Asn Asp Lys Glu
        35                  40                  45

Trp Leu Asn Asp Glu Val Ile Asn Leu Tyr Leu Glu Leu Leu Lys Glu
    50                  55                  60

Arg Glu Leu Arg Glu Pro Asn Lys Phe Leu Lys Cys His Phe Phe Asn
65                  70                  75                  80

Thr Phe Phe Tyr Lys Lys Leu Ile Asn Gly Tyr Asp Tyr Lys Ser Val
                85                  90                  95

Arg Glu Trp Thr Thr Met Arg Lys Leu Gly Tyr Asn Leu Ile Asp Cys
            100                 105                 110

Asp Lys Ile Phe Val Pro Ile His Lys Asp Val His Trp Cys Leu Ala
        115                 120                 125

Val Ile Asn Ile Lys Glu Lys Lys Phe Gln Tyr Leu Asp Ser Leu Gly
    130                 135                 140

Tyr Met Asp Met Lys Ala Leu Arg Ile Leu Ala Lys Tyr Leu Val Asp
145                 150                 155                 160

Glu Val Lys Asp Lys Ser Gly Lys Gln Ile Asp Val His Ala Trp Lys
                165                 170                 175

Gln Glu Gly Val Gln Asn Leu Pro Leu Gln Glu Asn Gly Trp Asp Cys
            180                 185                 190

Gly Met Phe Met Leu Lys Tyr Ile Asp Phe Tyr Ser Arg Asp Met Glu
        195                 200                 205

Leu Val Phe Gly Gln Lys His Met Ser Tyr Phe Arg Arg Arg Thr Ala
    210                 215                 220

Lys Glu Ile Leu Asp Leu Lys Ala Gly
225                 230
```

<210> SEQ ID NO 64
<211> LENGTH: 234
<212> TYPE: PRT
<213> ORGANISM: Artificial
<220> FEATURE:
<223> OTHER INFORMATION: MutI bdSENP1 residues 248-481

<400> SEQUENCE: 64

```
Pro Phe Val Pro Leu Thr Asp Glu Asp Glu Asp Asn Val Arg His Ala
1               5                   10                  15

Leu Gly Gly Arg Lys Lys Ser Glu Thr Leu Ser Val His Glu Ala Ser
                20                  25                  30

His Ile Val Ile Thr Arg Glu Ile Leu Gln Cys Leu Asn Asp Lys Glu
            35                  40                  45

Trp Leu Asn Asp Glu Val Ile Asn Leu Tyr Leu Glu Leu Leu Lys Glu
        50                  55                  60

Arg Glu Leu Arg Glu Pro Asn Lys Phe Leu Lys Cys His Phe Phe Asn
65                  70                  75                  80

Thr Phe Phe Tyr Lys Lys Leu Ile Asn Gly Gly Tyr Asp Tyr Lys Ser
                85                  90                  95

Val Arg Glu Trp Thr Thr Arg Arg Lys Leu Gly Tyr Asn Leu Ile Asp
                100                 105                 110

Cys Asp Lys Ile Phe Val Pro Ile His Lys Asp Val His Trp Cys Leu
            115                 120                 125

Ala Val Ile Asn Ile Lys Glu Lys Lys Phe Gln Tyr Leu Asp Ser Leu
130                 135                 140

Gly Tyr Met Asp Met Lys Ala Leu Arg Ile Leu Ala Lys Tyr Leu Val
145                 150                 155                 160

Asp Glu Val Lys Asp Lys Ser Gly Lys Gln Ile Asp Val His Ala Trp
                165                 170                 175

Lys Gln Glu Gly Val Gln Asn Leu Pro Leu Gln Glu Asn Gly Trp Asp
                180                 185                 190

Cys Gly Met Phe Met Leu Lys Tyr Ile Asp Phe Tyr Ser Arg Asp Met
                195                 200                 205

Glu Leu Val Phe Gly Lys His Met Ser Tyr Phe Arg Arg Arg Thr
                210                 215                 220

Ala Lys Glu Ile Leu Asp Leu Lys Ala Gly
225                 230
```

<210> SEQ ID NO 65
<211> LENGTH: 234
<212> TYPE: PRT
<213> ORGANISM: Artificial
<220> FEATURE:
<223> OTHER INFORMATION: MutJ bdSENP1 residues 248-481

<400> SEQUENCE: 65

```
Pro Phe Val Pro Leu Thr Asp Glu Asp Glu Asp Asn Val Arg His Ala
1               5                   10                  15

Leu Gly Gly Arg Lys Glu Ser Glu Thr Leu Ser Val His Glu Ala Ser
                20                  25                  30

Ser Ile Val Ile Thr Arg Glu Ile Leu Gln Cys Leu Asn Asp Lys Glu
            35                  40                  45

Trp Leu Asn Asp Glu Val Ile Asn Leu Tyr Leu Glu Leu Leu Lys Glu
        50                  55                  60

Arg Glu Leu Arg Glu Pro Asn Lys Phe Leu Lys Cys His Phe Phe Asn
65                  70                  75                  80

Thr Phe Phe Tyr Lys Lys Leu Ile Asn Gly Gly Tyr Asp Tyr Lys Ser
                85                  90                  95

Val Arg Ser Trp Thr Thr Thr Arg Lys Leu Gly Tyr Asn Leu Ile Asp
                100                 105                 110

Cys Asp Lys Ile Phe Val Pro Ile His Lys Asp Val His Trp Cys Leu
            115                 120                 125
```

Ala Val Ile Asn Ile Lys Glu Lys Lys Phe Gln Tyr Leu Asp Ser Leu
130                 135                 140

Gly Tyr Met Asp Met Lys Ala Leu Arg Ile Leu Ala Lys Tyr Leu Val
145                 150                 155                 160

Asp Glu Val Lys Asp Lys Ser Gly Lys Gln Ile Asp Val His Ala Trp
                165                 170                 175

Lys Gln Glu Gly Val Gln Asn Leu Pro Leu Gln Glu Asn Gly Trp Asp
            180                 185                 190

Cys Gly Met Phe Met Leu Lys Tyr Ile Asp Phe Tyr Ser Arg Asp Met
        195                 200                 205

Glu Leu Val Phe Gly Gln Lys His Met Ser Tyr Phe Arg Arg Arg Thr
    210                 215                 220

Ala Lys Glu Ile Leu Asp Leu Lys Ala Gly
225                 230

<210> SEQ ID NO 66
<211> LENGTH: 234
<212> TYPE: PRT
<213> ORGANISM: Artificial
<220> FEATURE:
<223> OTHER INFORMATION: MutK bdSENP1 residues 248-481

<400> SEQUENCE: 66

Pro Phe Val Pro Leu Thr Asp Glu Asp Glu Asp Asn Val Arg His Ala
1               5                   10                  15

Leu Gly Gly Arg Lys Val Ser Glu Thr Leu Ser Val His Glu Ala Ser
            20                  25                  30

Gln Ile Val Ile Thr Arg Glu Ile Leu Gln Cys Leu Asn Asp Lys Glu
        35                  40                  45

Trp Leu Asn Asp Glu Val Ile Asn Leu Tyr Leu Glu Leu Leu Lys Glu
    50                  55                  60

Arg Glu Leu Arg Glu Pro Asn Lys Phe Leu Lys Cys His Phe Phe Asn
65                  70                  75                  80

Thr Phe Phe Tyr Lys Lys Leu Ile Asn Gly Gly Tyr Asp Tyr Lys Ser
                85                  90                  95

Val Arg Val Trp Thr Thr Gly Arg Lys Leu Gly Tyr Asn Leu Ile Asp
            100                 105                 110

Cys Asp Lys Ile Phe Val Pro Ile His Lys Asp Val His Trp Cys Leu
        115                 120                 125

Ala Val Ile Asn Ile Lys Glu Lys Lys Phe Gln Tyr Leu Asp Ser Leu
130                 135                 140

Gly Tyr Met Asp Met Lys Ala Leu Arg Ile Leu Ala Lys Tyr Leu Val
145                 150                 155                 160

Asp Glu Val Lys Asp Lys Ser Gly Lys Gln Ile Asp Val His Ala Trp
                165                 170                 175

Lys Gln Glu Gly Val Gln Asn Leu Pro Leu Gln Glu Asn Gly Trp Asp
            180                 185                 190

Cys Gly Met Phe Met Leu Lys Tyr Ile Asp Phe Tyr Ser Arg Asp Met
        195                 200                 205

Glu Leu Val Phe Gly Gln Lys His Met Ser Tyr Phe Arg Arg Arg Thr
    210                 215                 220

Ala Lys Glu Ile Leu Asp Leu Lys Ala Gly
225                 230

<210> SEQ ID NO 67

```
<211> LENGTH: 234
<212> TYPE: PRT
<213> ORGANISM: Artificial
<220> FEATURE:
<223> OTHER INFORMATION: MutL bdSENP1 residues 248-481

<400> SEQUENCE: 67

Pro Phe Val Pro Leu Thr Asp Glu Asp Glu Asp Asn Val Arg His Ala
1               5                   10                  15

Leu Gly Gly Arg Lys Leu Ser Glu Thr Leu Ser Val His Glu Ala Ser
            20                  25                  30

Val Ile Val Ile Thr Arg Glu Ile Leu Gln Cys Leu Asn Asp Lys Glu
        35                  40                  45

Trp Leu Asn Asp Glu Val Ile Asn Leu Tyr Leu Glu Leu Leu Lys Glu
    50                  55                  60

Arg Glu Leu Arg Glu Pro Asn Lys Phe Leu Lys Cys His Phe Phe Asn
65                  70                  75                  80

Thr Phe Phe Tyr Lys Lys Leu Ile Asn Gly Gly Tyr Asp Tyr Lys Ser
                85                  90                  95

Val Arg Pro Trp Thr Thr Ala Arg Lys Leu Gly Tyr Asn Leu Ile Asp
            100                 105                 110

Cys Asp Lys Ile Phe Val Pro Ile His Lys Asp Val His Trp Cys Leu
        115                 120                 125

Ala Val Ile Asn Ile Lys Glu Lys Lys Phe Gln Tyr Leu Asp Ser Leu
    130                 135                 140

Gly Tyr Met Asp Met Lys Ala Leu Arg Ile Leu Ala Lys Tyr Leu Val
145                 150                 155                 160

Asp Glu Val Lys Asp Lys Ser Gly Lys Gln Ile Asp Val His Ala Trp
                165                 170                 175

Lys Gln Glu Gly Val Gln Asn Leu Pro Leu Gln Glu Asn Gly Trp Asp
            180                 185                 190

Cys Gly Met Phe Met Leu Lys Tyr Ile Asp Phe Tyr Ser Arg Asp Met
        195                 200                 205

Glu Leu Val Phe Gly Gln Lys His Met Ser Tyr Phe Arg Arg Arg Thr
    210                 215                 220

Ala Lys Glu Ile Leu Asp Leu Lys Ala Gly
225                 230

<210> SEQ ID NO 68
<211> LENGTH: 234
<212> TYPE: PRT
<213> ORGANISM: Artificial
<220> FEATURE:
<223> OTHER INFORMATION: MutM bdSENP1 residues 248-481

<400> SEQUENCE: 68

Pro Phe Val Pro Leu Thr Asp Glu Asp Glu Asp Asn Val Arg His Ala
1               5                   10                  15

Leu Gly Gly Arg Lys Ala Ser Glu Thr Leu Ser Val His Glu Ala Ser
            20                  25                  30

Trp Ile Val Ile Thr Arg Glu Ile Leu Gln Cys Leu Asn Asp Lys Glu
        35                  40                  45

Trp Leu Asn Asp Glu Val Ile Asn Leu Tyr Leu Glu Leu Leu Lys Glu
    50                  55                  60

Arg Glu Leu Arg Glu Pro Asn Lys Phe Leu Lys Cys His Phe Phe Asn
65                  70                  75                  80

Thr Phe Phe Tyr Lys Lys Leu Ile Asn Gly Gly Tyr Asp Tyr Lys Ser
```

|   |   |   |   | 85 |   |   |   | 90 |   |   |   | 95 |   |   |
|---|---|---|---|---|---|---|---|---|---|---|---|---|---|---|

Val Arg Arg Trp Thr Thr Glu Arg Lys Leu Gly Tyr Asn Leu Ile Asp
                     100                    105                110

Cys Asp Lys Ile Phe Val Pro Ile His Lys Asp Val His Trp Cys Leu
       115                   120                  125

Ala Val Ile Asn Ile Lys Glu Lys Lys Phe Gln Tyr Leu Asp Ser Leu
       130                   135                  140

Gly Tyr Met Asp Met Lys Ala Leu Arg Ile Leu Ala Lys Tyr Leu Val
145                    150                    155                  160

Asp Glu Val Lys Asp Lys Ser Gly Lys Gln Ile Asp Val His Ala Trp
                 165                   170                 175

Lys Gln Glu Gly Val Gln Asn Leu Pro Leu Gln Glu Asn Gly Trp Asp
             180                   185                  190

Cys Gly Met Phe Met Leu Lys Tyr Ile Asp Phe Tyr Ser Arg Asp Met
       195                   200                  205

Glu Leu Val Phe Gly Gln Lys His Met Ser Tyr Phe Arg Arg Arg Thr
       210                   215                  220

Ala Lys Glu Ile Leu Asp Leu Lys Ala Gly
225                    230

<210> SEQ ID NO 69
<211> LENGTH: 234
<212> TYPE: PRT
<213> ORGANISM: Artificial
<220> FEATURE:
<223> OTHER INFORMATION: MutN bdSENP1 residues 248-481

<400> SEQUENCE: 69

Pro Phe Val Pro Leu Thr Asp Glu Asp Glu Asp Asn Val Arg His Ala
1               5                  10                 15

Leu Gly Gly Arg Lys Ser Ser Glu Thr Leu Ser Val His Glu Ala Ser
            20                   25                   30

Pro Ile Val Ile Thr Arg Glu Ile Leu Gln Cys Leu Asn Asp Lys Glu
           35                   40                 45

Trp Leu Asn Asp Glu Val Ile Asn Leu Tyr Leu Glu Leu Leu Lys Glu
50                   55                    60

Arg Glu Leu Arg Glu Pro Asn Lys Phe Leu Lys Cys His Phe Phe Asn
65                   70                  75               80

Thr Phe Phe Tyr Lys Lys Leu Ile Asn Gly Tyr Asp Tyr Lys Ser
               85                   90                  95

Val Arg Arg Trp Thr Thr Arg Arg Lys Leu Gly Tyr Asn Leu Ile Asp
                     100                    105                110

Cys Asp Lys Ile Phe Val Pro Ile His Lys Asp Val His Trp Cys Leu
       115                   120                  125

Ala Val Ile Asn Ile Lys Glu Lys Lys Phe Gln Tyr Leu Asp Ser Leu
       130                   135                  140

Gly Tyr Met Asp Met Lys Ala Leu Arg Ile Leu Ala Lys Tyr Leu Val
145                    150                    155                  160

Asp Glu Val Lys Asp Lys Ser Gly Lys Gln Ile Asp Val His Ala Trp
                 165                   170                 175

Lys Gln Glu Gly Val Gln Asn Leu Pro Leu Gln Glu Asn Gly Trp Asp
             180                   185                  190

Cys Gly Met Phe Met Leu Lys Tyr Ile Asp Phe Tyr Ser Arg Asp Met
       195                   200                  205

Glu Leu Val Phe Gly Gln Lys His Met Ser Tyr Phe Arg Arg Arg Thr

```
                210                 215                 220

Ala Lys Glu Ile Leu Asp Leu Lys Ala Gly
225                 230

<210> SEQ ID NO 70
<211> LENGTH: 234
<212> TYPE: PRT
<213> ORGANISM: Artificial
<220> FEATURE:
<223> OTHER INFORMATION: MutO bdSENP1 residues 248-481

<400> SEQUENCE: 70

Pro Phe Val Pro Leu Thr Asp Glu Asp Glu Asp Asn Val Arg His Ala
1               5                   10                  15

Leu Gly Gly Arg Lys Arg Ser Glu Thr Leu Ser Val His Glu Ala Ser
            20                  25                  30

Arg Ile Val Ile Thr Arg Glu Ile Leu Gln Cys Leu Asn Asp Lys Glu
        35                  40                  45

Trp Leu Asn Asp Glu Val Ile Asn Leu Tyr Leu Glu Leu Leu Lys Glu
    50                  55                  60

Arg Glu Leu Arg Glu Pro Asn Lys Phe Leu Lys Cys His Phe Phe Asn
65                  70                  75                  80

Thr Phe Phe Tyr Lys Lys Leu Ile Asn Gly Gly Tyr Asp Tyr Lys Ser
                85                  90                  95

Val Arg Gly Trp Thr Thr Leu Arg Lys Leu Gly Tyr Asn Leu Ile Asp
            100                 105                 110

Cys Asp Lys Ile Phe Val Pro Ile His Lys Asp Val His Trp Cys Leu
        115                 120                 125

Ala Val Ile Asn Ile Lys Glu Lys Phe Gln Tyr Leu Asp Ser Leu
    130                 135                 140

Gly Tyr Met Asp Met Lys Ala Leu Arg Ile Leu Ala Lys Tyr Leu Val
145                 150                 155                 160

Asp Glu Val Lys Asp Lys Ser Gly Lys Gln Ile Asp Val His Ala Trp
                165                 170                 175

Lys Gln Glu Gly Val Gln Asn Leu Pro Leu Gln Glu Asn Gly Trp Asp
            180                 185                 190

Cys Gly Met Phe Met Leu Lys Tyr Ile Asp Phe Tyr Ser Arg Asp Met
        195                 200                 205

Glu Leu Val Phe Gly Gln Lys His Met Ser Tyr Phe Arg Arg Arg Thr
    210                 215                 220

Ala Lys Glu Ile Leu Asp Leu Lys Ala Gly
225                 230

<210> SEQ ID NO 71
<211> LENGTH: 373
<212> TYPE: PRT
<213> ORGANISM: Artificial
<220> FEATURE:
<223> OTHER INFORMATION: MBP fusion

<400> SEQUENCE: 71

Ala Gly Thr Gly Thr Ser Lys Thr Glu Glu Gly Lys Leu Val Ile Trp
1               5                   10                  15

Ile Asn Gly Asp Lys Gly Tyr Asn Gly Leu Ala Glu Val Gly Lys Lys
            20                  25                  30

Phe Glu Lys Asp Thr Gly Ile Lys Val Thr Val Glu His Pro Asp Lys
        35                  40                  45
```

```
Leu Glu Glu Lys Phe Pro Gln Val Ala Ala Thr Gly Asp Gly Pro Asp
 50                  55                  60

Ile Ile Phe Trp Ala His Asp Arg Phe Gly Gly Tyr Ala Gln Ser Gly
 65                  70                  75                  80

Leu Leu Ala Glu Ile Thr Pro Asp Lys Ala Phe Gln Asp Lys Leu Tyr
                 85                  90                  95

Pro Phe Thr Trp Asp Ala Val Arg Tyr Asn Gly Lys Leu Ile Ala Tyr
                100                 105                 110

Pro Ile Ala Val Glu Ala Leu Ser Leu Ile Tyr Asn Lys Asp Leu Leu
            115                 120                 125

Pro Asn Pro Pro Lys Thr Trp Glu Glu Ile Pro Ala Leu Asp Lys Glu
    130                 135                 140

Leu Lys Ala Lys Gly Lys Ser Ala Leu Met Phe Asn Leu Gln Glu Pro
145                 150                 155                 160

Tyr Phe Thr Trp Pro Leu Ile Ala Ala Asp Gly Gly Tyr Ala Phe Lys
                165                 170                 175

Tyr Glu Asn Gly Lys Tyr Asp Ile Lys Asp Val Gly Val Asp Asn Ala
            180                 185                 190

Gly Ala Lys Ala Gly Leu Thr Phe Leu Val Asp Leu Ile Lys Asn Lys
    195                 200                 205

His Met Asn Ala Asp Thr Asp Tyr Ser Ile Ala Glu Ala Ala Phe Asn
    210                 215                 220

Lys Gly Glu Thr Ala Met Thr Ile Asn Gly Pro Trp Ala Trp Ser Asn
225                 230                 235                 240

Ile Asp Thr Ser Lys Val Asn Tyr Gly Val Thr Val Leu Pro Thr Phe
                245                 250                 255

Lys Gly Gln Pro Ser Lys Pro Phe Val Gly Val Leu Ser Ala Gly Ile
            260                 265                 270

Asn Ala Ala Ser Pro Asn Lys Glu Leu Ala Lys Glu Phe Leu Glu Asn
    275                 280                 285

Tyr Leu Leu Thr Asp Glu Gly Leu Glu Ala Val Asn Lys Asp Lys Pro
    290                 295                 300

Leu Gly Ala Val Ala Leu Lys Ser Tyr Glu Glu Glu Leu Ala Lys Asp
305                 310                 315                 320

Pro Arg Ile Ala Ala Thr Met Glu Asn Ala Gln Lys Gly Glu Ile Met
                325                 330                 335

Pro Asn Ile Pro Gln Met Ser Ala Phe Trp Tyr Ala Val Arg Thr Ala
            340                 345                 350

Val Ile Asn Ala Ala Ser Gly Arg Gln Thr Val Asp Glu Ala Leu Lys
    355                 360                 365

Asp Ala Gln Thr Asn
    370

<210> SEQ ID NO 72
<211> LENGTH: 17
<212> TYPE: RNA
<213> ORGANISM: Artificial
<220> FEATURE:
<223> OTHER INFORMATION: RBS

<400> SEQUENCE: 72
aaaacaaguu auccaug                                                  17

<210> SEQ ID NO 73
<211> LENGTH: 481
<212> TYPE: PRT
```

<213> ORGANISM: Artificial Sequence
<220> FEATURE:
<223> OTHER INFORMATION: bdSENP1 amino acids 1-481

<400> SEQUENCE: 73

```
Met Gly Ala Leu Thr Asp Ser Arg Lys Arg Val Ser Ala Asp His Arg
1               5                   10                  15

Leu His Pro Ser Phe Pro Pro Ser Pro Pro Pro Ser Lys Arg Thr
                20                  25                  30

Lys Leu Ala Pro Leu Leu Pro Val Ser Ser Pro Pro Leu His Tyr
                35                  40                  45

Ala Ser Pro Ser Ser Ala Ala Pro Gly Pro Ser Ser Ala Ala Ala
            50                  55                  60

Ala Ala Ala Thr Ala Ser Thr Ser Ser His Ser Ser Leu Pro His Pro
65                  70                  75                  80

Arg Arg Arg Leu Pro Pro Ala Pro Pro Ile Ser Arg Pro Ile His Gly
                85                  90                  95

Pro Gln Arg Val Arg Arg Ser Phe Arg Gly Gly Asn Ser Arg Pro Asn
                100                 105                 110

Ser Asn Pro Pro Trp Tyr Ser Pro Ser Pro Pro Lys Pro Leu Gly
            115                 120                 125

Leu Asp Gln Tyr Ala Asp Leu Val Tyr Ser Val Thr His Pro Pro Arg
            130                 135                 140

Pro Thr Pro Ala Val His Val Pro Arg Gly Thr Glu Ala Ile Pro Glu
145                 150                 155                 160

Val Val Met Val Asp Asp Asn Glu Asp Ile Arg Gln Asp Lys Glu Asp
                165                 170                 175

Glu Gln Asp Val Glu Glu Ala Lys Ala Lys Val Val Gly Arg Lys
            180                 185                 190

Val Pro Leu Tyr Lys Glu Leu Tyr Glu Lys Ser Ser Arg Gln Arg Asp
            195                 200                 205

Ala Arg Leu Arg Thr Leu Glu Phe Glu Val Gln Leu Ala Glu Lys Gly
            210                 215                 220

Arg Leu Gly Leu Glu Arg Leu Ala Glu Val Leu Pro Arg Ile Thr Pro
225                 230                 235                 240

Asn Lys Glu Glu Val Pro Glu Pro Phe Val Pro Leu Thr Asp Glu Asp
                245                 250                 255

Glu Asp Asn Val Arg His Ala Leu Gly Gly Arg Lys Arg Ser Glu Thr
                260                 265                 270

Leu Ser Val His Glu Ala Ser Asn Ile Val Ile Thr Arg Glu Ile Leu
            275                 280                 285

Gln Cys Leu Asn Asp Lys Glu Trp Leu Asn Asp Glu Val Ile Asn Leu
            290                 295                 300

Tyr Leu Glu Leu Leu Lys Glu Arg Glu Leu Arg Glu Pro Asn Lys Phe
305                 310                 315                 320

Leu Lys Cys His Phe Phe Asn Thr Phe Tyr Lys Lys Leu Ile Asn
                325                 330                 335

Gly Gly Tyr Asp Tyr Lys Ser Val Arg Arg Trp Thr Thr Lys Arg Lys
                340                 345                 350

Leu Gly Tyr Asn Leu Ile Asp Cys Asp Lys Ile Phe Val Pro Ile His
            355                 360                 365

Lys Asp Val His Trp Cys Leu Ala Val Ile Asn Ile Lys Glu Lys Lys
370                 375                 380

Phe Gln Tyr Leu Asp Ser Leu Gly Tyr Met Asp Met Lys Ala Leu Arg
```

```
385                 390                 395                 400
Ile Leu Ala Lys Tyr Leu Val Asp Glu Val Lys Asp Lys Ser Gly Lys
            405                 410                 415

Gln Ile Asp Val His Ala Trp Lys Gln Glu Gly Val Gln Asn Leu Pro
            420                 425                 430

Leu Gln Glu Asn Gly Trp Asp Cys Gly Met Phe Met Leu Lys Tyr Ile
        435                 440                 445

Asp Phe Tyr Ser Arg Asp Met Glu Leu Val Phe Gly Gln Lys His Met
    450                 455                 460

Ser Tyr Phe Arg Arg Arg Thr Ala Lys Glu Ile Leu Asp Leu Lys Ala
465                 470                 475                 480

Gly
```